United States Patent
Ke et al.

(10) Patent No.: US 12,370,187 B2
(45) Date of Patent: Jul. 29, 2025

(54) COMPOSITION CONTAINING ANTITUMOR DRUG, AND PREPARATION METHOD THEREOF AND USE THEREOF

(71) Applicant: KUNSHAN XINYUNDA BIOTECH CO., LTD., Jiangsu (CN)

(72) Inventors: Tianyi Ke, Jiangsu (CN); Lin Tan, Jiangsu (CN); Baigang Wen, Jiangsu (CN); Fang Lao, Jiangsu (CN); Yan Liu, Jiangsu (CN); Ningxia Wang, Jiangsu (CN); Shang Ju, Jiangsu (CN); Dongxue Cui, Jiangsu (CN); Xuzhao Du, Jiangsu (CN); Fangxing Ouyang, Jiangsu (CN)

(73) Assignee: KUNSHAN XINYUNDA BIOTECH CO., LTD., Jiangsu (CN)

( * ) Notice: Subject to any disclaimer, the term of this patent is extended or adjusted under 35 U.S.C. 154(b) by 0 days.

(21) Appl. No.: 18/436,704

(22) Filed: Feb. 8, 2024

(65) Prior Publication Data
US 2024/0252482 A1 Aug. 1, 2024

Related U.S. Application Data

(63) Continuation-in-part of application No. PCT/CN2022/124787, filed on Oct. 12, 2022.

(30) Foreign Application Priority Data

Oct. 15, 2021 (CN) .......................... 202111202739.7

(51) Int. Cl.
*A61K 31/4745* (2006.01)
*A61K 9/51* (2006.01)
*A61P 35/00* (2006.01)

(52) U.S. Cl.
CPC ........ *A61K 31/4745* (2013.01); *A61K 9/5123* (2013.01); *A61K 9/5169* (2013.01); *A61K 9/5192* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 2008/0069868 A1 | 3/2008 | Yoshino et al. | |
| 2019/0110993 A1* | 4/2019 | Selvaraj | A61K 9/5192 |
| 2020/0197314 A1 | 6/2020 | Li et al. | |

FOREIGN PATENT DOCUMENTS

| | | |
|---|---|---|
| CN | 101670112 A | 3/2010 |
| CN | 104622810 A | 5/2015 |

(Continued)

OTHER PUBLICATIONS

J. Allen Zhang, Tong Xuan, Manjeet Parmar, Lan Ma, Sydney Ugwu, Shahid Ali, Imran Ahmad. "Development and characterization of a novel liposome-based formulation of SN-38." International Journal of Pharmaceutics, vol. 270, 2004, pp. 93-107. (Year: 2004).*

(Continued)

*Primary Examiner* — Isaac Shomer
(74) *Attorney, Agent, or Firm* — Rothwell, Figg, Ernst & Manbeck, P.C.

(57) ABSTRACT

Disclosed are a composition containing 7-ethyl-10-hydroxy-camptothecin, and a preparation method therefor and the use thereof. The composition contains SN-38, a lipid, albumin and Span 20.

22 Claims, 15 Drawing Sheets

Specification includes a Sequence Listing.

(56) References Cited

FOREIGN PATENT DOCUMENTS

| CN | 107412783 A | 12/2017 |
|---|---|---|
| JP | 2019-510085 A | 4/2019 |
| WO | 02/058622 A2 | 8/2002 |

OTHER PUBLICATIONS

J.N. Israelachvili, S. Marcelja, and R.G Horn. "Physical principles of membrane organization." Quarterly Reviews of Biophysics, vol. 13(2), 1980, pp. 121-200. (Year: 1980).*

Min Wu et al. "Disruption of YPS1 and PEP4 genes reduces proteolytic degradation of secreted HSA/PTH in Pichia pastoris GS115. " Journal of Indian Microbiology and Biotechnology, vol. 40, 2013, pp. 589-599 and 8 pages of supplementary material. (Year: 2013).*

GenBank: AER13700.1. "HSA-GGGGS-PTH(1-34), partial [synthetic construct]." Entered GenBank May 28, 2013. https://www.ncbi.nlm.nih.gov/protein/AER13700.1?report=genbank&log$=protalign&blast_rank=9&RID=JWJGAZWY013&from=1&to=585 accessed Nov. 8, 2024, pp. 1-2. (Year: 2013).*

Written Opinion mailed Nov. 29, 2022 in corresponding International Application No. PCT/CN2022/124787 (8 pages).

International Search Report mailed Nov. 29, 2022 in corresponding International Application No. PCT/CN2022/124787 (10 pages).

Taneja et al., "Rational design of polysorbate 80 stabilized human serum albumin nanoparticles tailored for high drug loading and entrapment of irinotecan." International Journal of Pharmaceutics, vol. 536, Nov. 13, 2017 (Nov. 13, 2017), pp. 82-94 (13 pages).

Shirazi, et al., "SN38 loaded nanostructured lipid carriers (NLCs); preparation and in vitro evaluations against glioblastoma", Journal of Materials Science: Materials in Medicine vol. 32, Jun. 30, 2021, 78 (12 pages).

Stetefeld et al., "Dynamic light scattering: a practical guide and applications in biomedical sciences" Biophys Rev, 2016, vol. 8, pp. 409-427.

Official Action mailed Nov. 13, 2024 in corresponding Eurasian Patent Convention Application No. 202490973 (with English translation)(12 pages).

Masoudipour et al., "Surfactant effects on the particle size, zeta potential, and stability of starch nanoparticles and their use in a pH-responsive manner", Springer, Cellulose DOI 10.1007/s10570-017-1426-3, Aug. 5, 2017 (18 pages).

Dong, et al., "Effects of surfactants on size and structure of amylose nanoparticles prepared by precipitation", Bull. Mater. Sci., vol. 39, No. 1, Feb. 2016, pp. 35-39 (5 pages).

Bouchemal, et al., "Nano-emulsion formulation using spontaneous emulsification: solvent, oil and surfactant optimisation", International Journal of Pharmaceutics 280 (2004) 241-251 (11 pages).

Le-Vinh, et al., "Effects of polymeric surfactants with low HLB values on drug and excipient release from self-emulsifying drug delivery systems", Journal of Drug Delivery Science and Technology 91 (2024) 105199 (13 pages).

Examination report No. 1 for standard patent application mailed Nov. 26, 2024 in corresponding Australian Patent Application No. 2022367142 (3 pages).

Notice of Reasons for Refusal mailed Mar. 11, 2025 in corresponding Japanese Patent Application No. 2024-502452 (with English machine translation) (4 pages).

Hsin-Che Lin, et al.; "High Potency of SN-38-Loaded Bovine Serum Albumin Nanoparticles Against Triple-Negative Breast Cancer"; Pharmaceutics 2019, vol. 11, No. 569; pp. 1-21.

R. Nazari-Vanani, et al.; "Capecitabine-loaded Nanonosomes and Evaluation of Anticancer Efficacy"; Artificial Cells Nanomedicine and Biotechnology; Jan. 23, 2019; vol. 47, No. 1; pp. 420-426.

* cited by examiner

SEQUENCE LISTING

```
Sequence total quantity: 1
SEQ ID NO: 1              moltype = AA  length = 585
FEATURE                   Location/Qualifiers
source                    1..585
                          mol_type = protein
                          organism = Homo sapiens
SEQUENCE: 1
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV 120
DVMCTAFHDN EETFLKKYLY EIARRHPYFY APELLFFAKR YKAAFTECCQ AADKAACLLP 180
KLDELRDEGK ASSAKQRLKC ASLQKFGERA FKAWAVARLS QRFPKAEFAE VSKLVTDLTK 240
VHTECCHGDL LECADDRADL AKYICENQDS ISSKLKECCE KPLLEKSHCI AEVENDEMPA 300
DLPSLAADFV ESKDVCKNYA EAKDVFLGMF LYEYARRHPD YSVVLLLRLA KTYETTLEKC 360
CAAADPHECY AKVFDEFKPL VEEPQNLIKQ NCELFKQLGE YKFQNALLVR YTKKVPQVST 420
PTLVEVSRNL GKVGSKCCKH PEAKRMPCAE DYLSVVLNQL CVLHEKTPVS DRVTKCCTES 480
LVNRRPCFSA LEVDETYVPK EFNAETFTFH ADICTLSEKE RQIKKQTALV ELVKHKPKAT 540
KEQLKAVMDD FAAFVEKCCK ADDKETCFAE EGKKLVAASQ AALGL             585
```

COMPOSITION CONTAINING ANTITUMOR DRUG, AND PREPARATION METHOD THEREOF AND USE THEREOF

CROSS-REFERENCE TO RELATED APPLICATIONS

This application is a continuation-in-part of and claims priority to International Application No. PCT/CN2022/124787, filed Oct. 12, 2022, which claims priority to Chinese Patent Application No. 202111202739.7, filed Oct. 15, 2021. The benefit of priority is claimed to each of the foregoing, and the entire contents of each of the foregoing are incorporated herein by reference.

SEQUENCE LISTING

The instant application contains a Sequence Listing, which has been submitted in XML format and is hereby incorporated by reference in its entirety. Said Sequence Listing was created on Feb. 8, 2024 and is named 2398-154.xml and is 4,096 bytes in size.

FIELD OF THE INVENTION

The present application relates to a composition of 7-ethyl-10-hydroxycamptothecin (SN-38) that comprises SN-38, a lipid, an albumin, and Span 20, and also to a preparation method and use thereof.

BACKGROUND OF THE INVENTION

SN-38 is an active metabolite of the marketed drug irinotecan hydrochloride (CPT-11) in the body, and has an efficacy on some tumor cells is about 100-1000 times that of CPT-11 (Zhang J A, Xuan T, Parmar M, et al., Development and characterization of a novel liposome-based formulation of SN-38, [J]. *International journal of pharmaceutics*, 2004, 270(1):93-107). SN-38 has an inhibitory effect on a variety of tumor cells, such as colorectal cancer, small cell lung cancer, lymph cancer, breast cancer, esophageal cancer, uterine cancer, and ovarian cancer. However, the efficiency of transformation of CPT-11 into SN-38 in the body is very low and is merely 2-8% (Rowinsky E K, Grochow L B, Ettinger D S, et al., Phase I and pharmacological study of the novel topoisomerase I inhibitor CPT-11 administered as a ninety-minute infusion every 3 weeks, [J]. *Cancer research*, 1994, 54(2): 427-436).

Studies have shown that the closed-ring lactonic structure of SN-38 is the effective component for exerting the anticancer activity of SN-38. However, SN-38 with this closed ring structure is insoluble in most biocompatible and pharmaceutically acceptable solvents and is low in druggability. These factors greatly restrict the development and clinical use of SN-38. So far, there is no pharmaceutical formulation comprising SN-38 as an active ingredient being approved for marketing.

Therefore, there is now still an urgent need for solving the problems of solubility and druggability of SN-38. To solve the solubility problem of SN-38, some studies have devoted to the structural modification of SN-38. The modification may be classified into water solubility modification and liposolubility modification, the former may be found in, for example, WO1995022549A1, and the latter may be found in, for example, US20060229359A. The liposolubility modification typically involves preparing SN-38 into a liposome, and the preparation process typically includes modifying a camptothecin molecule with a hydrophobic molecule such as a long-chain fatty acid or cholesterol, vitamin E, and a lipophilic organic acid, and then preparing a camptothecin-liposome product with the modified camptothecin molecule and a certain proportion of an excipient such as phospholipid and cholesterol. CN108567742A is directed to obtaining a camptothecin-liposome product by improving an excipient rather than hydrophobically modifying SN-38. Those products reported above contain no albumin, but enable camptothecin to maintain a larger proportion of the active closed-ring structure by modification with lipids and to be entrapped by the albumin after entering the body, thereby prolonging the efficacy.

In addition, the stability and scale-up of the preparation process of SN-38 formulations are always challenges for drugability of SN-38 due to the more special physical and chemical properties of SN-38, such as easier crystallization in water and positive-charged surface, as compared to paclitaxel drugs.

Nanoliposomes, nanosuspensions and the like obtained by either water solubility or liposolubility modification/liposome preparation have the shortcomings of unsatisfactory loading of drug of SN-38, complex preparation process, or poor repeatability after process scale-up, and unstable formulations. It is still an urgent problem to be solved to obtain cost-effectively a SN-38 nanoformulation with a high loading of drug of SN-38 by a process that is easy and stable for scale-up, by the way of optimizing the components of the formulation and the process.

The prior application (PCT/CN2021/102332) of the inventors describes a composition with high loading of drug comprising SN-38, a lipid and an albumin, which leads to an SN-38 formulation suitable for drug preparation. On the basis of the above work, the investors have surprisingly found that addition of Span 20 to the composition leads to the reduction of the number of high pressure homogenization during preparation, effectively reduced particle size of the formulation, increased filtration flux, and reduction of the raw material loss and the cost. Meanwhile, the obtained pharmaceutical formulation has better stability, better particle size control after disintegration, and more stable efficacy. The contents of PCT/CN2021/102332 is incorporated by reference herein in its entirety.

CONTENTS OF THE INVENTION

Summary of the Invention

International patent application PCT/CN2021/102332 describes a composition comprising SN-38, a lipid, and an albumin. The inventors have found that in larger-scale (e.g., 100 milligrams or more of SN-38 raw material) preparation, including a scaled-up process, e.g., a pilot-scale preparation, when Span 20 is added to the composition, the number of high pressure homogenization during preparation can be reduced, the particle size of nanoparticles in the composition is effective reduced, the filtration flux is increased, the raw material loss and the cost is reduced, and meanwhile, the particle size of the nanoparticles after disintegration can be controlled. By further controlling the content of the albumin in the composition, the particle size of the nanoparticles can be controlled such that it is closer to a size suitable for drug preparation. The composition of the invention also has the advantages of the composition in PCT/CN2021/102332, including: (1) increased loading of drug and encapsulation efficiency of SN-38; (2) inclusion of a low level of SN-38 with an open-ring structure; (3) no inclusion of albumin multimer, low immunogenicity, and high safety; (4) small particle size and narrow particle size distribution of nanoparticles; (5) excellent stability (including excellent dilution stability and storage stability); (6) SN-38 which exists in an amorphous form and/or in the form of nanocrystal, and has the advantages of high dissolution rate and high bioavailability; and (7) excellent in vivo antitumor efficacy.

In a first aspect, the present application provides a composition comprising SN-38, a lipid, an albumin, and Span 20, which is characterized in that the composition comprises nanoparticles, wherein in the nanoparticles, the albumin encapsulates at least part of the SN-38 and optionally at least part of the lipid, wherein the lipid is selected from cholesterol, cholesterol derivatives, cholesterol analogues, and fatty acid esters, and any combination of two or more of them.

In a second aspect, the present application provides a method for preparing the composition according to the first aspect.

In a third aspect, the present application provides a method for preparing a composition comprising SN-38, a lipid, an albumin, and Span 20.

In a fourth aspect, the present application provides a composition that can be prepared by the method according to the third aspect.

In a fifth aspect, the present application further provides a method for preparing a composition with improved properties.

Other aspects of the present application further provide a pharmaceutical composition comprising the compositions described above and use thereof.

DETAILED DESCRIPTION OF THE INVENTION

Definitions

Figure 1:
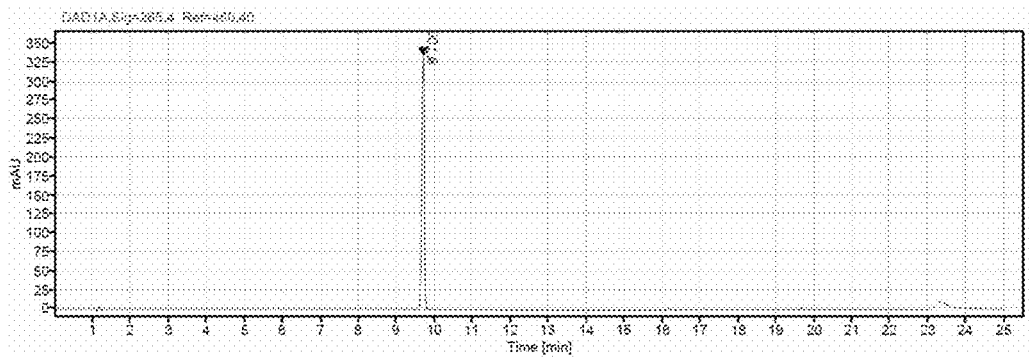
FIG. 1 is a typical HPLC chromatogram of a content measurement of SN-38 in the product prepared in Example 1.

Unless otherwise defined below, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The term "nanoparticle" represents a particle having a nanoscale size in at least one dimension (e.g., one, two, or three dimensions), e.g., a size of about 1 nm, about 10 nm, about 100 nm, or about 200-300 nm, preferably a size of not more than 200 nm.

The term "nanocrystal" refers to a crystal having a size of 1 to 1000 nm, especially a crystal of 50 to 300 nm, which may be a single crystal or a polycrystal.

The term "vesicle" refers to an organized molecular assembly having an outer layer structure that may be spontaneously formed when dispersed in an aqueous phase.

The term "Span 20", also referred to as sorbitan monolaurate or Span20, is a surfactant.

The term "aqueous composition" refers to a water-based composition, which is in a liquid or semisolid form, preferably in the liquid form. The liquid form includes but is not limited to a solution (e.g., a solution of protein nanoparticles), a colloid, an emulsion, and a suspension.

The terms "loading of drug (LD)" and "encapsulation efficiency (EE)" may be calculated according to formulas provided in Examples.

The term "organic acid" includes saturated or unsaturated fatty acids having 1 to 24 carbon atoms, especially short-chain fatty acids having 2 to 4 carbon atoms, medium-chain fatty acids having 6 to 12 carbon atoms, and long-chain fatty acids having 14 to 24 carbon atoms; and aromatic carboxylic acids. An example that may be particularly mentioned is octanoic acid. "Long-chain fatty acids" include but are not limited to palmitic acid (C16:0), stearic acid (C18:0), oleic acid (C18:1), linoleic acid (C18:2), α-linolenic acid (C18:3), arachidonic acid (C20:4), timnodonic acid (C20:5), and docosahexaenoic acid (C22:6). Examples that may be particularly mentioned are palmitic acid and stearic acid.

The terms "include", "comprise", "have", "contain" or "relate to", and other variations thereof herein are inclusive or open-ended, and do not exclude additional, unrecited elements or method steps, although said additional, unrecited elements or method steps do not necessarily exist (i.e., these terms also encompass the terms "essentially consist of" and "consist of").

The term "about" refers to a range within ±10%, preferably within +5%, and more preferably within ±2% of the specified value.

A numerical range recited herein should include any and all sub-ranges encompassed therein. For example, the range of "1 to 10" should be construed as including not only the clearly recited values of 1 to 10 but also any single value (such as 2, 3, 4, 5, 6, 7, 8, and 9) and any sub-range (such as 1 to 2, 1.5 to 2.5, 1 to 3, 1.5 to 3.5, 2.5 to 4, and 3 to 4.5) within the range of 1 to 10. The principle also applies to a range using only one value as a minimum value or a maximum value.

All documents mentioned throughout the description are incorporated herein by reference in their entirety.

In a first aspect, the present application provides a composition comprising SN-38, a lipid, an albumin, and Span 20, which is characterized in that the composition comprises nanoparticles, wherein in the nanoparticles, the albumin encapsulates at least part of the SN-38 and optionally at least part of the lipid;

lipid:SN-38 is about (0.1-10):1 (w:w);
albumin:SN-38 is about (1-100):1 (w:w); and
Span 20:SN-38 is about (3-60):100 (w:w); and
wherein the lipid is selected from cholesterol, cholesterol derivatives, cholesterol analogues, and fatty acid esters, and any combination of two or more of them.

In some embodiments, lipid:SN-38 is about (0.5-6):1 (w:w), such as about (0.5-5):1 (w:w), about (0.5-3):1 (w:w), about (1-4):1 (w:w), about (1.2-4):1 (w:w), about (1.4-2):1 (w:w), about (1.5-2.5):1 (w:w), or about 1:1 (w:w).

In some embodiments, albumin:SN-38 is about (1-50):1 (w:w), such as about (3-25):1 (w:w), about (5-25):1 (w:w), about (5-20):1 (w:w), or about (5-18):1 (w:w), about (6-15):1 (w:w), about (7-15):1 (w:w), about (6-12):1 (w:w), about (7-12):1 (w:w), about (9-11):1 (w:w), or about 10:1 (w:w).

In some embodiments, Span 20:SN-38 is about (4-60):100 (w:w), such as about (5-60):100 (w:w), about (6-60):100 (w:w), about (7-55):100 (w:w), about (8-50):100 (w:w), about (10-45):100 (w:w), about (12-40):100 (w:w), about (14-35):100 (w:w), about (15-30):100 (w:w), about (16-25):100 (w:w), or about (18-20):100 (w:w).

In some embodiments, albumin:lipid is about (1-100):1 (w:w), such as about (2-20):1 (w:w), about (3-15):1 (w:w), or about (5-10):1 (w:w), e.g., about 7:1 (w:w) or about 10:1 (w:w).

In some embodiments, based on the total amount of the SN-38, the lipid, and the albumin in the composition, the SN-38 has a content of about 1 w/w % to about 25 w/w %. In some embodiments, based on the total amount of the SN-38, the lipid, and the albumin in the composition, the lipid has a content of about 1 w/w % to about 35 w/w %. In some embodiments, based on the total amount of the SN-38, the lipid, and the albumin in the composition, the albumin has a content of about 50 w/w % to about 98 w/w %.

In some embodiments, based on the total amount of the SN-38, the lipid, and the albumin in the composition, the SN-38 has a content of about 3 w/w % to about 20 w/w %. In some embodiments, based on the total amount of the SN-38, the lipid, and the albumin in the composition, the lipid has a content of about 2 w/w % to about 30 w/w %. In some embodiments, based on the total amount of the SN-38, the lipid, and the albumin in the composition, the albumin has a content of about 55 w/w % to about 95 w/w %.

In some embodiments, based on the total amount of the SN-38, the lipid, and the albumin in the composition, the SN-38 has a content of about 3 w/w % to about 15 w/w %, such as about 4 w/w %, about 5 w/w %, about 6 w/w %, about 6.5 w/w %, about 7 w/w %, about 7.5 w/w %, about 8 w/w %, about 8.5 w/w %, about 9 w/w %, about 10 w/w %, about 11 w/w %, about 12 w/w %, about 13 w/w %, or about 14 w/w %.

In some embodiments, based on the total amount of the SN-38, the lipid, and the albumin in the composition, the lipid has a content of about 3 w/w % to about 30 w/w %, such as about 4 w/w %, about 5 w/w %, about 6 w/w %, about 7 w/w %, about 8 w/w %, about 8.5 w/w %, about 9 w/w %, about 9.5 w/w %, about 10 w/w %, about 10.5 w/w %, about 11 w/w %, about 11.5 w/w %, about 12 w/w %, about 12.5 w/w %, about 13 w/w %, about 13.5 w/w %, about 14 w/w %, about 15 w/w %, about 16 w/w %, about 17 w/w %, about 18 w/w %, about 19 w/w %, about 20 w/w %, about 21 w/w %, about 24 w/w %, about 26 w/w %, or about 28 w/w %.

In some embodiments, based on the total amount of the SN-38, the lipid, and the albumin in the composition, the albumin has a content of about 60 w/w % to about 94 w/w %, such as about 64 w/w % to about 93 w/w %, about 66 w/w % to about 92 w/w %, about 68 w/w % to about 91 w/w %, about 70 w/w % to about 90 w/w %, about 75 w/w % to about 90 w/w %, about 75 w/w %, about 76 w/w %, about 77 w/w %, about 78 w/w %, about 79 w/w %, about 80 w/w %, about 81 w/w %, about 82 w/w %, about 83 w/w %, about 84 w/w %, about 85 w/w %, about 86 w/w %, about 87 w/w %, about 88 w/w %, or about 89 w/w %.

Without any hope to be bound to any theory, the inventors have found that with increasing the lipid amount used, the composition tends to have a smaller average particle size, higher encapsulation efficiency, and higher availability of SN-38; an increase in the albumin amount used may result in a reduction in loading of drug; and an excessively high albumin content may also increase the particle size of nanoparticles, affecting drugability. In one embodiment, based on the total amount of the SN-38, the lipid, and the albumin in the composition, the content of the lipid is about 5 w/w % to about 24 w/w %. In one embodiment, based on the total amount of the SN-38, the lipid, and the albumin in the composition, the content of the albumin is about 60 w/w % to about 90 w/w %.

On the other hand, an excessively high content of the lipid component in the composition may have an adverse effect on individuals. From the perspective of reducing lipid intake caused by the administration of the composition, it is expected to be preferred that based on the total amount of the SN-38, the lipid, and the albumin in the composition, the content of the lipid in the composition is not more than about 18 w/w %, e.g., not more than about 16 w/w % or not more than about 14 w/w %. However, this does not mean that a composition having a higher lipid content is not desirable.

In some embodiments, based on the total amount of the SN-38, the lipid, the albumin, and Span 20 in the composition, the Span 20 has a content of about 0.03 w/w % to about 12 w/w %, such as about 0.06 w/w % to about 10 w/w %, 0.08 w/w % to about 9 w/w %, about 0.1 w/w % to about 8 w/w %, about 0.2 w/w % to about 7 w/w %, about 0.4 w/w % to about 6 w/w %, about 0.6 w/w % to about 5 w/w %, about 0.8 w/w % to about 4 w/w %, about 1 w/w % to about 2 w/w %.

In some embodiments, lipid:SN-38 is about (1-10):1 (w:w), such as about (1-8):1 (w:w), about (1-6):1 (w:w), about (1-5):1 (w:w), about (1-4.5):1 (w:w), about (1-4):1 (w:w), about (1.2-3.8):1 (w:w), about 1:1 (w:w), about (1.4-3.6):1 (w:w), about (1.6-3.4):1 (w:w), about (1.8-3.2):1 (w:w), about (2-3):1 (w:w), about (2.2-2.8):1 (w:w), about (2.4-2.6):1 (w:w), about 1:1 (w:w), or about 2.5:1 (w:w). In some other embodiments, lipid:SN-38 is about (0.8-1.8):1 (w:w), about (0.9-1.7):1 (w:w), or about (1-1.4):1.

In some embodiments, albumin:SN-38 is about (5-40):1 (w:w), such as about (5 to less than 40):1 (w:w), about (5-35):1 (w:w), about (5-30):1 (w:w), about (8-25):1 (w:w), about (10-22.5):1 (w:w), about (12.5-20):1 (w:w), about (15-17.5):1 (w:w), about (16-18):1 (w:w), or about 10:1 (w:w). In some other embodiments, albumin:SN-38 is about (9-21):1 (w:w), about (9-20):1 (w:w), about (11-18):1 (w:w), or about (11.1-17.3):1 (w:w).

In some embodiments, Span 20:SN-38 is about (5-60):100 (w:w), such as about (6-60):100 (w:w), about (7-55):100 (w:w), about (8-50):100 (w:w), about (10-45):100 (w:w), about (12-40):100 (w:w), about (14-35):100 (w:w), about (15-30):100 (w:w), about (16-25):100 (w:w), or about (18-20):100 (w:w). In some other embodiments, Span 20:SN-38 is about (5-10):100 (w:w), about (5-9):100 (w:w), about (6-8.6):100 (w:w), about (6-8):100 (w:w), or about (6.5-7):100 (w:w).

In some embodiments, albumin:lipid is about (1-40):1 (w:w), such as about (1 to less than 40):1 (w:w), about (2-35):1 (w:w), about (3-15):1 (w:w), about (5-10):1 (w:w), or about (6-8):1 (w:w), e.g., about 7:1 (w:w) or about 10:1 (w:w). In some embodiments, albumin:lipid is about (6-21):1 (w:w), about (6.7-13):1 (w:w), about (7-13):1 (w:w), or about (11-12.7):1 (w:w).

In some embodiments, based on the total amount of the SN-38, the lipid, and the albumin in the composition, the content of the SN-38 is about 2 w/w % to about 16 w/w %. In some embodiments, based on the total amount of the SN-38, the lipid, and the albumin in the composition, the content of the lipid is about 2 w/w % to about 35 w/w %. In some embodiments, based on the total amount of the SN-38, the lipid, and the albumin in the composition, the content of the albumin is about 75 w/w % to about 96 w/w %.

In some embodiments, based on the total amount of the SN-38, the lipid, and the albumin in the composition, the content of the SN-38 is about 2.5 w/w % to about 15 w/w %, such as about 4 w/w % to about 10 w/w %, about 4.5 w/w % to about 9.5 w/w %, about 5 w/w % to about 9 w/w %, or about 7.5 w/w % to about 8 w/w %. In some embodiments, based on the total amount of the SN-38, the lipid, and the albumin in the composition, the content of the lipid in the composition is about 2.5 w/w % to about 30 w/w %, such as about 4 w/w % to about 12.5 w/w %, about 4.5 w/w % to about 12 w/w %, about 7 w/w % to about 10 w/w %, or about 7.5 w/w % to about 8 w/w %. In some embodiments, based on the total amount of the SN-38, the lipid, and the albumin in the composition, the content of the albumin is about 76 w/w % to about 95 w/w %, such as about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %.

In some embodiments, based on the total amount of the SN-38, the lipid, and the albumin in the composition, the content of the SN-38 is about 3 w/w % to about 14 w/w %, such as about 3.5 w/w % to about 12 w/w %, about 4 w/w %, about 4.2 w/w %, about 4.5 w/w %, about 4.6 w/w %, about 4.8 w/w %, about 5 w/w %, about 5.5 w/w %, about 6 w/w %, about 6.5 w/w %, about 7 w/w %, about 7.5 w/w %, about 7.6 w/w %, about 7.8 w/w %, about 8 w/w %, about 8.5 w/w %, about 9 w/w %, about 9.2 w/w %, about 9.5 w/w %, about 9.6 w/w %, about 9.8 w/w %, about 10 w/w %, about 10.5 w/w %, about 11 w/w %, or about 11.5 w/w %.

In some embodiments, based on the total amount of the SN-38, the lipid, and the albumin in the composition, the content of the lipid is about 4 w/w % to about 25 w/w %, such as about 4.5 w/w % to about 20 w/w %, about 4.3 w/w %, about 4.5 w/w %, about 4.7 w/w %, about 5 w/w %, about 5.5 w/w %, about 6 w/w %, about 6.5 w/w %, about 7 w/w %, about 7.5 w/w %, about 7.6 w/w %, about 7.8 w/w %, about 8 w/w %, 8.5 w/w %, about 9 w/w %, about 9.5 w/w %, about 10 w/w %, about 10.5 w/w %, about 11 w/w %, about 11.5 w/w %, about 12 w/w %, about 12.1 w/w %, about 12.3 w/w %, about 12.5 w/w %, about 13 w/w %, about 13.5 w/w %, about 14 w/w %, about 14.5 w/w %, about 15 w/w %, about 15.5 w/w %, about 16 w/w %, about 16.5 w/w %, about 17 w/w %, about 17.5 w/w %, about 18 w/w %, about 18.5 w/w %, about 19 w/w %, or about 19.5 w/w %.

In some embodiments, based on the total amount of the SN-38, the lipid, and the albumin in the composition, the content of the albumin is about 78 w/w % to about 92 w/w %, such as about 79 w/w %, about 79.2 w/w %, about 79.4 w/w %, about 79.6 w/w %, about 79.8 w/w %, about 80 w/w %, about 81 w/w %, about 82 w/w %, about 83 w/w %, about 84 w/w %, about 84.3 w/w %, about 84.5 w/w %, about 84.7 w/w %, about 84.9 w/w %, about 85 w/w %, about 86 w/w %, about 87 w/w %, about 87.3 w/w %, about 87.5 w/w %, about 87.7 w/w %, about 87.9 w/w %, about 88 w/w %, about 89 w/w %, about 90 w/w %, about 91 w/w %, about 91.3 w/w %, or about 91.5 w/w %.

In some embodiments, based on the total amount of the SN-38, the lipid, the albumin, and the Span 20 in the composition, the content of the Span 20 is about 0.14 w/w % to about 5 w/w %, such as about 0.2 w/w % to about 2.5 w/w %, about 0.22 w/w % to about 2.0 w/w %, about 0.24 w/w % to about 2 w/w %, about 0.26 w/w % to about 1.5 w/w %, about 0.28 w/w % to about 1.0 w/w %, about 0.3 w/w % to about 0.9 w/w %, about 0.32 w/w % to about 0.8 w/w %, about 0.34 w/w % to about 0.7 w/w %, about 0.36 w/w % to about 0.6 w/w %, about 0.38 w/w % to about 0.58 w/w %, about 0.4 w/w % to about 0.56 w/w %, about 0.42 w/w % to about 0.54 w/w %, about 0.44 w/w % to about 0.52 w/w %, about 0.46 w/w %, about 0.48 w/w %, or about 0.5 w/w %. In some other embodiments, the content of the Span 20 is about 0.2 w/w % to about 0.8 w/w %, about 0.24 w/w % to about 0.7 w/w %, about 0.26 w/w % to about 0.7 w/w %, about 0.3 w/w % to about 0.65 w/w %, about 0.36 w/w % to about 0.6 w/w %, about 0.4 w/w % to about 0.58 w/w %, about 0.44 w/w % to about 0.56 w/w %, about 0.48 w/w % to about 0.54 w/w %, or about 0.5 w/w % to about 0.52 w/w %.

In some embodiments, the SN-38 existing in the nanoparticles accounts for at least about 1 w/w % or at least about 2 w/w %, such as at least about 3 w/w %, about 3 w/w % to about 13 w/w %, about 4 w/w % to about 12 w/w %, about 4 w/w %, about 5 w/w %, about 6 w/w %, about 7 w/w %, about 8 w/w %, about 9 w/w %, about 10 w/w %, or about 11 w/w %, of the total amount of the SN-38, the lipid, and the albumin in the composition.

In some embodiments, the SN-38 existing in the nanoparticles accounts for about 80 w/w % to about 99 w/w %, such as about 88 w/w % to about 98 w/w %, about 89 w/w %, about 90 w/w %, about 91 w/w %, about 92 w/w %, about 93 w/w %, about 94 w/w %, about 95 w/w %, about 96 w/w %, or about 97 w/w %, of the total amount of the SN-38 in the composition.

In some embodiments, the cholesterol derivatives are selected from esters formed by cholesterol and organic acids, preferably selected from cholesteryl palmitate, cholesteryl caprylate, and a combination thereof.

In some embodiments, the cholesterol analogues are selected from vitamin D2, vitamin D3, and a combination thereof.

In some embodiments, the fatty acid esters are selected from fatty acid glycerides, preferably long-chain fatty acid glycerides, preferably glyceryl stearate, and more preferably glyceryl monostearate.

In some preferred embodiments, the lipid is selected from cholesterol, cholesteryl palmitate, cholesteryl caprylate, vitamin D2, vitamin D3, glyceryl monostearate, and any combination of two or more of them.

In some preferred embodiments, the lipid is selected from cholesterol, cholesteryl palmitate, vitamin D3, glyceryl monostearate, and any combination of two or more of them.

In some preferred embodiments, the lipid is: cholesterol, cholesteryl palmitate, vitamin D3, or glyceryl monostearate; a mixture of cholesterol and cholesteryl palmitate; a mixture of cholesterol and vitamin D3; a mixture of cholesterol and glyceryl monostearate; or a mixture of cholesteryl palmitate and glyceryl monostearate.

In some more preferred embodiments, the lipid is cholesterol. Preferably, the cholesterol is used as the only lipid. In some of such embodiments, cholesterol:SN-38 is about (1-6):1 (w:w), such as about (1.2-5):1 (w:w), e.g., about (1.4-4):1 (w:w), about 3:1 (w:w), about 2:1 (w:w), or about 1:1 (w:w). In some other embodiments, cholesterol:SN-38 is about (0.8-1.8):1 (w:w), about (0.9-1.7):1 (w:w), about (1-1.4):1. In some of such embodiments, albumin:SN-38 is about (3-25):1 (w:w), such as about (4-20):1 (w:w), about (5-15):1 (w:w), about (6-12):1 (w:w), about (7-12):1 (w:w), about (9-11):1 (w:w), or about 10:1 (w:w). In some other embodiments, albumin:SN-38 is about (9-21):1 (w:w), about (9-20):1 (w:w), about (11-18):1 (w:w), or about (11.1-17.3):1 (w:w). In some such embodiments, albumin:cholesterol is about (2-20):1 (w:w), such as about (3-15):1 (w:w), about (5-10):1 (w:w), or about 7:1 (w:w). In some other embodiments, albumin:cholesterol is about (6-21):1 (w:w), about (6.7-13):1 (w:w), about (7-13):1 (w:w), or about (11-12.7):1 (w:w).

In some of such embodiments, based on the total amount of the SN-38, the cholesterol, and the albumin in the composition, the content of the SN-38 is about 3 w/w % to about 15 w/w %, such as about 4 w/w % to about 15 w/w %, about 6 w/w % to about 10 w/w %, or about 8 w/w % to about 12 w/w %. In some other embodiments, the content of the SN-38 is about 4 w/w % to about 10 w/w %, about 4.5 w/w % to about 9.5 w/w %, about 5 w/w % to about 9 w/w %, or about 7.5 w/w % to about 8 w/w %. In some of such embodiments, based on the total amount of the SN-38, the cholesterol, and the albumin in the composition, the content of the cholesterol is about 5 w/w % to about 25 w/w %, such as about 6 w/w % to about 22 w/w % or about 15 w/w % to about 20 w/w %. In some other embodiments, the content of the cholesterol is about 4 w/w % to about 12.5 w/w %, about 4.5 w/w % to about 12 w/w %, about 7 w/w % to about 10 w/w %, or about 7.5 w/w % to about 8 w/w %. In some of such embodiments, based on the total amount of the SN-38, the cholesterol, and the albumin in the composition, the content of the albumin is about 64 w/w % to about 90 w/w %, e.g., about 70 w/w % to about 90 w/w %. In some other embodiments, the content of the albumin is about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %. In some of such embodiments, the SN-38 existing in the nanoparticles accounts for at least about 3 w/w %, such as about 3 w/w % to about 13 w/w %, about 4 w/w % to about 12 w/w %, about 4 w/w %, about 5 w/w %, about 6 w/w %, about 7 w/w %, about 8 w/w %, about 9 w/w %, about 10 w/w %, or about 11 w/w %, of the total amount of the SN-38, the cholesterol, and the albumin in the composition.

In some other embodiments, the lipid is cholesteryl palmitate. In some embodiments, the lipid is vitamin D3. In some embodiments, the lipid is glyceryl monostearate. In some embodiments, cholesteryl palmitate, vitamin D3, or glyceryl monostearate is used as the only lipid.

It may also be encompassed that the lipid is the mixture of cholesterol and glyceryl monostearate, wherein cholesterol:glyceryl monostearate is, for example, about (0.2-5):1 (w:w), about (0.5-3):1 (w:w), about (0.5-2):1 (w:w), or about 1:1 (w:w).

In some embodiments, the lipid is the mixture of cholesteryl palmitate and glyceryl monostearate, wherein cholesteryl palmitate:glyceryl monostearate is, for example, about (0.2-5):1 (w:w), about (0.5-3):1 (w:w), about (0.5-2):1 (w:w), or about 1:1 (w:w).

In some embodiments, the lipid is the mixture of cholesterol and cholesteryl palmitate, wherein cholesterol:cholesteryl palmitate is, for example, about (0.2-5):1 (w:w), about (0.5-3):1 (w:w), about (0.5-2):1 (w:w), or about 1:1 (w:w).

As for the embodiments comprising a lipid other than cholesterol, or a combination of cholesterol and another lipid, the lipid:SN-38 is, for example, (1-6):1 (w:w), about (1.2-5):1 (w:w), about (1.4-4.5):1 (w:w), about 4.3:1 (w:w), about 3:1 (w:w), about 1:1 (w:w), or about 2:1 (w:w). In some of such embodiments, albumin:SN-38 is, for example, about (5-25):1 (w:w), about (10-20):1 (w:w), about (6-15):1 (w:w), about (7-15):1 (w:w), about (9-12):1 (w:w), about (9-11):1 (w:w), about 9.5:1 (w:w), or about 10:1 (w:w). In some of such embodiments, albumin: the lipid is, for example, about (2-10):1 (w:w), about (3-7):1 (w:w), or about (4-6):1 (w:w). In some of such embodiments, based on the total amount of the SN-38, the lipid, and the albumin in the composition, the content of the SN-38 is, for example, about 5 w/w % to about 15 w/w %, about 6 w/w % to about 12 w/w %, about 7 w/w % to about 10 w/w %, about 8 w/w %, or about 9 w/w %. In some of such embodiments, based on the total amount of the SN-38, the lipid, and the albumin in the composition, the content of the lipid is, for example, about 5 w/w % to about 32 w/w %, about 10 w/w % to about 30 w/w %, about 18 w/w %, about 20 w/w %, about 22 w/w %, about 24 w/w %, about 26 w/w %, about 28 w/w %, or about 29 w/w %. In some of such embodiments, based on the total amount of the SN-38, the lipid, and the albumin in the composition, the content of the albumin is, for example, about 60 w/w % to about 90 w/w %, about 64 w/w % to about 85 w/w %, about 70 w/w % to about 80 w/w %, or about 75 w/w %. In some of such embodiments, the SN-38 existing in the nanoparticles accounts for at least about 3 w/w %, such as about 3 w/w % to about 10 w/w %, about 4 w/w % to about 9 w/w %, about 4 w/w %, about 5 w/w %, about 6 w/w %, about 7 w/w %, or about 8 w/w %, of the total amount of the SN-38, the lipid, and the albumin in the composition.

In some embodiments described above, the composition is in a liquid, semisolid, or solid form.

In some embodiments, the composition is in a solid form, preferably a powder form. More preferably, the composition is a lyophilized powder.

In some of such embodiments, the SN-38 exists in the composition preferably in an amorphous and/or nanocrystal form, as measured by electron microscopy or X-ray diffraction (Cu-Kα) analysis. The nanocrystal may have a particle size in a range of about 30-500 nm, preferably about 50-200 nm. The SN-38 in the nanocrystal form accounts for 75% or higher, such as 80%, 85%, 90%, or higher, of the total SN-38.

Without any hope to be bound to any theory, in the composition of the present application, the Span 20 plays a role in improving the stability of the composition, adjusting the particle size of nanoparticles and making them more dispersed.

In some embodiments, the composition comprises no additional stabilizer. In some other embodiments, the composition preferably further comprises an additional stabilizer, e.g., a lyophilization stabilizer, wherein the additional stabilizer is in such an amount that, when the composition is reconstituted to form an aqueous composition (including a solution and an emulsion), the additional stabilizer has a content of at least about 2 w/v %, such as at least about 3 w/v %, at least about 5 w/v %, about 5 w/v % to about 30 w/v %, about 10 w/v % to about 25 w/v %, or about 15 w/v % to about 20 w/v %.

In some of such embodiments, the composition further comprises an additional stabilizer which has a content of about 60 w/w % to about 98 w/w %, such as about 65 w/w % to about 97 w/w %, about 68 w/w % to about 96 w/w %, about 69 w/w % to about 95 w/w %, about 70 w/w % to about 94 w/w %, about 71 w/w % to about 93 w/w %, about 72 w/w % to about 92 w/w %, about 73 w/w %, about 74 w/w %, about 75 w/w %, about 76 w/w %, about 77 w/w %, about 78 w/w %, about 79 w/w %, about 80 w/w %, about 81 w/w %, about 82 w/w %, about 83 w/w %, about 84 w/w %, about 85 w/w %, about 86 w/w %, about 87 w/w %, about 88 w/w %, about 89 w/w %, about 90 w/w %, or about 91 w/w %, based on the total amount of the composition.

In some embodiments, when the composition is reconstituted to form an aqueous composition (including a solution and an emulsion) which has a content of the SN-38 of about 0.1 μg/mL to about 30.0 mg/mL (or the content values of the SN-38 described below with respect to the aqueous composition), the nanoparticles have an average particle size of about 50 to 200 nm, such as about 90 to 150 nm, about 95 to 140 nm, about 100 to 130 nm, about 105 to 125 nm, or about 110 to 120 nm.

In some other embodiments, the composition is an aqueous composition in the liquid form, including a solution and an emulsion.

In some embodiments, the composition in the liquid form comprises the SN-38 in the form of nanocrystals and/or vesicles. The particle size range of the nanocrystals may be about 30-500 nm, preferably about 50-200 nm.

In some of such embodiments, the composition is in the form of a solution; and in some of such embodiments, the composition is in the form of an emulsion.

The inventors have found that the aqueous composition of the present application has excellent dilution stability. In some embodiments, when diluting (e.g., using 1×PBS at about pH 7.4) the composition to result in a content of the SN-38 of about 4 μg/mL or lower, such as about 2 μg/mL or lower, about 1 μg/mL or lower, or about 0.4 μg/mL or lower, e.g., about 0.1p g/mL or 0.04 μg/mL, in the diluted composition, the nanoparticles do not undergo disintegration. Due to excellent stability, the aqueous composition may exist as a concentrated solution or a diluted solution.

Therefore, different components of the aqueous composition may have wide content ranges. In some of such embodiments, based on the total amount of the composition, the content of the SN-38 is about 0.1 μg/mL to about 30.0 mg/mL, about 0.2 μg/mL to about 27.0 mg/mL, about 0.5 μg/mL to about 24.0 mg/mL, about 1.0 μg/mL to about 21.0 mg/mL, about 5.0 μg/mL to about 18.0 mg/mL, about 10.0 μg/mL to about 15.0 mg/mL, about 20.0 μg/mL to about 12 mg/mL, about 25.0 μg/mL to about 9 mg/mL, about 50.0 μg/mL to about 6.0 mg/mL, or about 100.0 μg/mL to about 3.0 mg/mL.

In some embodiments, based on the total amount of the composition, the content of the lipid is about 0.05 μg/mL to about 100.0 mg/mL, about 0.1 μg/mL to about 90.0 mg/mL, about 0.25 μg/mL to about 80.0 mg/mL, about 0.5 μg/mL to about 70.0 mg/mL, about 2.5 μg/mL to about 60.0 mg/mL, about 5.0 μg/mL to about 50.0 mg/mL, about 10.0 μg/mL to about 40.0 mg/mL, about 12.5 μg/mL to about 30.0 mg/mL, about 25.0 μg/mL to about 20.0 mg/mL, or about 50.0 μg/mL to about 10.0 mg/mL.

In some embodiments, based on the total amount of the composition, the content of the albumin is about 3.0 μg/mL to about 300.0 mg/mL, about 6.0 μg/mL to about 270.0 mg/mL, about 15.0 μg/mL to about 240.0 mg/mL, about 30.0 μg/mL to about 210.0 mg/mL, about 150.0 μg/mL to about 180.0 mg/mL, about 300.0 μg/mL to about 150.0 mg/mL, about 600.0 μg/mL to about 120.0 mg/mL, about 750.0 μg/mL to about 90.0 mg/mL, about 1500.0 μg/mL to about 60.0 mg/mL, or about 3.0 mg/mL to about 30.0 mg/mL.

In general, based on the total amount of the composition, the content of the SN-38 may be about 100.0 μg/mL to about 3.0 mg/mL, such as about 200.0 μg/mL to about 2.5 mg/mL, about 300.0 μg/mL to about 2.0 mg/mL, about 400.0 μg/mL to about 1.5 mg/mL, about 500.0 μg/mL to about 1.0 mg/mL, or about 600 μg/mL to about 800 μg/mL; and/or the content of the lipid may be about 50.0 μg/mL to about 10.0 mg/mL, such as about 100.0 μg/mL to about 8.0 mg/mL, about 200.0 µg/mL to about 6.0 mg/mL, about 300.0 µg/mL to about 4.0 mg/mL, about 400.0 µg/mL to about 3.0 mg/mL, about 500.0 µg/mL to about 2.5 mg/mL, about 600.0 µg/mL to about 2.0 mg/mL, about 700.0 µg/mL to about 1.5 mg/mL, about 800 µg/mL to about 1.0 mg/mL, or about 200 µg/mL to about 1.5 mg/mL; and/or the content of the albumin may be about 3.0 mg/mL to about 30.0 mg/mL, such as about 4.0 mg/mL to about 25.0 mg/mL, about 5.0 mg/mL to about 20.0 mg/mL, about 6.0 mg/mL to about 15.0 mg/mL, about 7.0 mg/mL to about 12.0 mg/mL, or about 8.0 mg/mL to about 10.0 mg/mL.

Ideally, in an aqueous composition (including a solution and an emulsion), the nanoparticles have an average particle size of not more than about 200 nm, e.g., not more than about 150 nm, and preferably, the average particle size of the nanoparticles still meets the requirement as described above, after storage for a certain time before administration. The inventors have found that the aqueous composition of the present application has such excellent properties.

In some embodiments, the nanoparticles have an average particle size of about 50 to 200 nm, such as about 90 to 150 nm or about 100 to 130 nm.

In some embodiments, after storage at 4° C. for 24 h, the nanoparticles have an average particle size of about 50 to 200 nm, such as about 90 to 150 nm or about 100 to 130 nm.

In some embodiments, the nanoparticles have a particle size distribution index (PDI) of not more than about 0.30, such as not more than about 0.2, not more than about 0.10, or not more than about 0.01.

In some embodiments, the composition has a Zeta potential of about −35 mV to about −20 mV, e.g., about −31 mV.

In some of such embodiments, the composition comprises no additional stabilizer. In some of such embodiments, the composition further comprises an additional stabilizer which has a content of at least about 2 w/v %, preferably at least about 3 w/v %, such as at least about 5 w/v %, about 5 w/v % to about 30 w/v %, about 10 w/v % to about 25 w/v %, or about 15 w/v % to about 20 w/v %, based on the total amount of the composition.

The additional stabilizer described above may be selected from albumins (such as human serum albumin, recombinant human albumin, bovine serum albumin, and skim milk powder), monosaccharides, disaccharides, polysaccharides, and any combination thereof, preferably selected from glucose and sucrose, preferably sucrose.

The use of the additional stabilizer is conducive to maintaining the average particle size of the nanoparticles. The inventors have found that the existence of the additional stabilizer reduces the increase in the average particle size of the nanoparticles in the aqueous composition after storage at 4° C. for 24 h, as compared to the absence of an additional stabilizer. Meanwhile, as for a composition finally provided in the form of a lyophilized powder, the use of additional stabilizers, in particular saccharide stabilizers, further provides additional advantages because they can act as lyophilization excipients at the same time in the course of lyophilizing the aqueous composition so that the use of other lyophilization excipients, in particular albumins (e.g., HSA) used as lyophilization excipients in the prior art, can be avoided, thus producing cost effectiveness and being conducive to reducing the risk of drug anaphylaxis. Therefore, in some embodiments, the composition preferably comprises no additional lyophilization stabilizer. Of course, the composition can also include an additional lyophilization excipient, such as one or more of sucrose, mannitol, lactose, maltose, trehalose, and dextran, where necessary.

In a first subset of the first aspect, the present application provides a composition comprising SN-38, a lipid, an albumin, and Span 20, wherein the lipid is cholesterol, characterized in that the composition comprises nanoparticles, wherein in the nanoparticles, the albumin encapsulates at least part of the SN-38 and optionally at least part of the lipid, wherein:
cholesterol:SN-38 is, in some embodiments, about (1-3):1 (w:w), such as about (1.2-2.5):1 (w:w), about (1.4-2):1 (w:w), about (1.5-2):1 (w:w), about (1.3-1.8):1 (w:w), about (1.4-1.6):1 (w:w), about (1.5-1.7):1 (w:w), about (1.2-1.5):1 (w:w), about 1:1 (w:w), or about (1.4-1.5):1 (w:w), or in some other embodiments, about (0.8-1.8):1 (w:w), about (0.9-1.7):1 (w:w), or about (1-1.4):1;

albumin:SN-38 is, in some embodiments, about (5-15):1 (w:w), such as about (5-12):1 (w:w), about (6-12):1 (w:w), or about (7-12):1 (w:w), about (9-11):1 (w:w), about (10-12):1 (w:w), or about 11:1 (w:w), or in some other embodiments, about (9-21):1 (w:w), about (9-20):1 (w:w), about (11-18):1 (w:w), or about (11.1-17.3):1 (w:w);

albumin:cholesterol is, in some embodiments, about (3-10):1 (w:w), about (4-8):1 (w:w), or about (5-7):1 (w:w), or in some other embodiments, about (6-21):1 (w:w), about (6.7-13):1 (w:w), about (7-13):1 (w:w), or about (11-12.7):1 (w:w); and Span 20:SN-38 is as described above.

In some embodiments, based on the total amount of the SN-38, the cholesterol, and the albumin in the composition, the content of the SN-38 is about 6 w/w % to about 14 w/w %, such as about 6.5 w/w % to about 13 w/w %, about 7 w/w % to about 12 w/w %, about 7.5 w/w % to about 12 w/w %, about 8 w/w % to about 11 w/w %, about 8.5 w/w % to about 10 w/w %, or about 9 w/w %. In some other embodiments, the content of the SN-38 is about 4 w/w % to about 10 w/w %, about 4.5 w/w % to about 9.5 w/w %, about 5 w/w % to about 9 w/w %, or about 7.5 w/w % to about 8 w/w %. In some embodiments, based on the total amount of the SN-38, the cholesterol, and the albumin in the composition, the content of the cholesterol is about 8 w/w % to about 18 w/w %, such as 8.5 w/w % to about 17 w/w %, about 9 w/w % to about 16 w/w %, about 9.5 w/w % to about 16 w/w %, about 10 w/w % to about 16 w/w %, about 10.5 w/w % to about 16 w/w %, about 11 w/w % to about 15 w/w %, about 11.5 w/w % to about 15 w/w %, about 12 w/w % to about 15 w/w %, about 12.5 w/w % to about 14 w/w %, or about 13 w/w % to about 13.5 w/w %. In some other embodiments, the content of the cholesterol is about 4 w/w % to about 12.5 w/w %, about 4.5 w/w % to about 12 w/w %, about 7 w/w % to about 10 w/w %, or about 7.5 w/w % to about 8 w/w %. In some embodiments, based on the total amount of the SN-38, the cholesterol, and the albumin in the composition, the content of the albumin is about 66 w/w % to about 90 w/w %, such as about 68 w/w % to about 89 w/w, about 70 w/w % to about 88 w/w %, about 70 w/w % to about 87 w/w %, about 70 w/w % to about 86 w/w %, about 70 w/w % to about 85 w/w %, about 75 w/w % to about 85 w/w %, about 76 w/w %, about 77 w/w %, about 78 w/w %, about 79 w/w %, about 80 w/w %, about 81 w/w %, about 82 w/w %, about 83 w/w %, or about 84 w/w %. In some other embodiments, the content of the albumin is about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %.

In a second subset of the first aspect, the present application provides a composition comprising SN-38, a lipid, an albumin, and Span 20, wherein the lipid is cholesterol, characterized in that the composition comprises nanoparticles, wherein in the nanoparticles, the albumin encapsulates at least part of the SN-38 and optionally at least part of the lipid, wherein:
cholesterol:SN-38 is, in some embodiments, about (1-5):1 (w:w), such as about (1-4.5):1 (w:w), about (1-4):1 (w:w), about (1.2-3.8):1 (w:w), about (1.4-3.6):1 (w:w), about (1.6-3.4):1 (w:w), about (1.8-3.2):1 (w:w), about (2-3):1 (w:w), about (2.2-2.8):1 (w:w), about (2.4-2.6):1 (w:w), about 2.5:1 (w:w), or about 1:1 (w:w), or in some other embodiments, about (0.8-1.8):1 (w:w), about (0.9-1.7):1 (w:w), or about (1-1.4):1; and/or albumin:SN-38 is, in some embodiments, about (5-25):1 (w:w), such as about (5-20):1 (w:w), about (6-19):1 (w:w), about (7-18):1 (w:w), about (8-16):1 (w:w), about (9-14):1 (w:w), or about (10-12):1 (w:w), or in some other embodiments, about (9-21):1 (w:w), about (9-20):1 (w:w), about (11-18):1 (w:w), or about (11.1-17.3):1 (w:w); and/or albumin:cholesterol is, in some embodiments, about (5-25):1 (w:w), such as about (6-20):1 (w:w), about (7-18):1 (w:w), about (8-16):1 (w:w), about (9-14):1 (w:w), or about (10-12):1 (w:w), or in some other embodiments, about (6-21):1 (w:w), about (6.7-13):1 (w:w), about (7-13):1 (w:w), about (11-12.7):1 (w:w); and/or Span 20:SN-38 is, in some embodiments, about (5-15):100 (w:w), such as about (6-12):100 (w:w), about (7-10):100 (w:w), or about 7.5:100 (w:w), or in some other embodiments, about (5-10):100 (w:w), about (5-9):100 (w:w), about (6-8.6):100 (w:w), about (6-8):100 (w:w), or about (6.5-7):100 (w:w).

In some of such embodiments, based on the total amount of the SN-38, the cholesterol, and the albumin in the composition, the content of the SN-38 is about 3 w/w % to about 10 w/w %, such as about 3.5 w/w % to about 9.5 w/w %, about 4 w/w %, about 4.5 w/w %, about 5 w/w %, about 5.5 w/w %, about 6 w/w %, about 6.5 w/w %, about 7 w/w %, about 7.5 w/w %, about 8 w/w %, about 8.5 w/w %, or about 9 w/w %. In some other embodiments, the content of the SN-38 is about 4 w/w % to about 10 w/w %, about 4.5 w/w % to about 9.5 w/w %, about 5 w/w % to about 9 w/w %, or about 7.5 w/w % to about 8 w/w %.

In some of such embodiments, based on the total amount of the SN-38, the cholesterol, and the albumin in the composition, the content of the cholesterol is about 4 w/w % to about 18 w/w %, such as about 4.5 w/w % to about 17.5 w/w %, about 5 w/w %, about 5.5 w/w %, about 6 w/w %, about 6.5 w/w %, about 7 w/w %, about 7.5 w/w %, about 8 w/w %, 8.5 w/w %, about 9 w/w %, about 9.5 w/w %, about 10 w/w %, about 10.5 w/w %, about 11 w/w %, about 11.5 w/w %, about 12 w/w %, about 12.5 w/w %, about 13 w/w %, about 13.5 w/w %, about 14 w/w %, about 14.5 w/w %, about 15 w/w %, about 15.5 w/w %, about 16 w/w %, about 16.5 w/w %, or about 17 w/w %. In some other embodiments, the content of the cholesterol is about 4 w/w % to about 12.5 w/w %, about 4.5 w/w % to about 12 w/w %, about 7 w/w % to about 10 w/w %, or about 7.5 w/w % to about 8 w/w %.

In some of such embodiments, based on the total amount of the SN-38, the cholesterol, and the albumin in the composition, the content of the albumin is about 78 w/w % to about 92 w/w %, such as about 79 w/w %, about 80 w/w %, about 81 w/w %, about 82 w/w %, about 83 w/w %, about 84 w/w %, about 85 w/w %, about 86 w/w %, about 87 w/w %, about 88 w/w %, about 89 w/w %, about 90 w/w %, or about 91 w/w %. In some other embodiments, the content of the albumin is about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %.

In some further embodiments, the invention provides the composition as described above, wherein:
cholesterol:SN-38 is about (1-2.5):1 (w:w), such as about 1.25:1 (w:w) or about 1:1 (w:w); and/or
albumin:SN-38 is about (8-25):1 (w:w), such as about (10-20):1 (w:w), about (12-18):1 (w:w), about (12.5-17):1 (w:w), about (15-16):1 (w:w), about 10:1 (w:w), or about 16.7:1 (w:w); and/or
albumin:cholesterol is about (5-10):1 (w:w), such as about (6-9):1 (w:w), about (7-8):1 (w:w), about 10:1 (w:w), or about 6.7:1 (w:w); and/or
Span 20:SN-38 is about (5-40):100 (w:w), such as about (6-30):100 (w:w), about (7-25):100 (w:w), about (8-20):100 (w:w), about (9-15):100 (w:w), or about (10-12):100 (w:w).

In some embodiments, based on the total amount of the SN-38, the cholesterol, and the albumin in the composition, the content of the SN-38 is about 3 w/w % to about 9 w/w %, such as about 3.5 w/w % to about 8.5 w/w %, about 4 w/w %, about 4.5 w/w %, about 5 w/w %, about 5.5 w/w %, about 6 w/w %, about 6.5 w/w %, about 7 w/w %, about 7.5 w/w %, or about 8 w/w %.

In some embodiments, based on the total amount of the SN-38, the cholesterol, and the albumin in the composition, the content of the cholesterol is about 8 w/w % to about 18 w/w %, such as about 8.5 w/w % to about 17.5 w/w %, about 9 w/w %, about 9.5 w/w %, about 10 w/w %, about 10.5 w/w %, about 11 w/w %, about 11.5 w/w %, about 12 w/w %, about 12.5 w/w %, about 13 w/w %, about 13.5 w/w %, about 14 w/w %, about 14.5 w/w %, about 15 w/w %, about 15.5 w/w %, about 16 w/w %, about 16.5 w/w %, or about 17 w/w %.

In some embodiments, based on the total amount of the SN-38, the lipid, the albumin, and the Span 20 in the composition, the content of the Span 20 is about 0.2 w/w % to about 0.6 w/w %, such as about 0.22 w/w % to about 0.58 w/w %, about 0.24 w/w % to about 0.56 w/w %, about 0.26 w/w % to about 0.54 w/w %, about 0.28 w/w % to about 0.52 w/w %, about 0.3 w/w % to about 0.5 w/w %, about 0.32 w/w % to about 0.48 w/w %, about 0.34 w/w % to about 0.46 w/w %, about 0.36 w/w % to about 0.44 w/w %, about 0.38 w/w % to about 0.42 w/w %, or about 0.4 w/w %.

In some other further embodiments, the invention provides the composition as described above, wherein:
cholesterol:SN-38 is about (0.8-1.8):1 (w:w), about (0.9-1.7):1 (w:w), or about (1-1.4):1; and/or
albumin:SN-38 is about (9-21):1 (w:w), about (9-20):1 (w:w), about (11-18):1 (w:w), or about (11.1-17.3):1 (w:w); and/or
albumin:cholesterol is about (6-21):1 (w:w), about (6.7-13):1 (w:w), about (7-13):1 (w:w), or about (11-12.7):1 (w:w); and/or Span 20:SN-38 is about (5-10):100 (w:w), about (5-9): 100 (w:w), about (6-8.6):100 (w:w), about (6-8):100 (w:w), or about (6.5-7):100 (w:w); and/or based on the total amount of the SN-38, the cholesterol, and the albumin in the composition, the content of the SN-38 is about 4 w/w % to about 10 w/w %, about 4.5 w/w % to about 9.5 w/w %, about 5 w/w % to about 9 w/w %, or about 7.5 w/w % to about 8 w/w %; and/or the content of the cholesterol is about 4 w/w % to about 12.5 w/w %, about 4.5 w/w % to about 12 w/w %, about 7 w/w % to about 10 w/w %, or about 7.5 w/w % to about 8 w/w %; and/or the content of the albumin is about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %; and/or the content of the Span 20 is about 0.2 w/w % to about 0.8 w/w %, about 0.24 w/w % to about 0.7 w/w %, about 0.26 w/w % to about 0.7 w/w %, about 0.3 w/w % to about 0.65 w/w %, about 0.36 w/w % to about 0.6 w/w %, about 0.4 w/w % to about 0.58 w/w %, about 0.44 w/w % to about 0.56 w/w %, about 0.48 w/w % to about 0.54 w/w %, or about 0.5 w/w % to about 0.52 w/w %.

The composition according to the second subset has advantages in the preparation at a larger scale (e.g., an order of hundreds of milligrams or more of the SN-38 raw material), including in a scaled-up process, e.g., in pilot-scale preparation, such as reduced number of high pressure homogenization during preparation, effective reduction of the particle size of the nanoparticles in the composition and increased filtration flux, controllable particle size after disintegration under physiological conditions, and reduction of the raw material loss and the cost, as well as possession of an appropriate content of the albumin so that the particle size of the nanoparticles can be controlled to be closer to a size suitable for drug preparation.

In some embodiments according to the first subset and the second subset, the SN-38 existing in the nanoparticles accounts for at least about 6 w/w % to about 12 w/w %, such as about 7 w/w % to about 11 w/w %, about 8 w/w % to about 10 w/w %, about 8.3%, or about 9 w/w %, of the total amount of the SN-38, the cholesterol, and the albumin in the composition.

In some embodiments, the SN-38 existing in the nanoparticles accounts for about 95 w/w % to about 99 w/w %, such as about 96 w/w % to about 99 w/w %, about 97 w/w % to about 99 w/w %, about 98 w/w % to about 99 w/w %, or about 99 w/w % or higher, of the total amount of the SN-38 in the composition.

In some embodiments as described above, the composition is in a liquid, semisolid, or solid form.

In some embodiments, the composition is in the solid form, preferably a powder form, more preferably a lyophilized powder.

In some of such embodiments, the SN-38 exists in the composition preferably in an amorphous and/or nanocrystal form, as measured by electron microscopy and X-ray diffraction (Cu-Kα) analysis.

In some embodiments, the composition comprises no additional stabilizer. In some embodiments, the composition further comprises an additional stabilizer, wherein the additional stabilizer is in such an amount that, when the composition is reconstituted to form an aqueous composition (including a solution and an emulsion), the additional stabilizer has a content of at least about 2 w/v %, such as at least about 3 w/v %, at least about 5 w/v %, about 5 w/v % to about 30 w/v %, about 10 w/v % to about 25 w/v %, or about 15 w/v % to about 20 w/v %.

In some of such embodiments, the composition further comprises an additional stabilizer which has a content of about 70 w/w % to about 96 w/w %, such as about 70 w/w % to about 90 w/w %, about 72 w/w % to about 89 w/w %, about 74 w/w % to about 88 w/w %, about 76 w/w % to about 87 w/w %, about 80 w/w % to about 86 w/w %, about 81 w/w % to about 86 w/w %, about 82 w/w % to about 85 w/w %, or about 83 w/w % to about 84 w/w %, based on the total amount of the composition. In some other embodiments, the composition further comprises an additional stabilizer which has a content of about 80 w/w % to about 96 w/w % or about 84 w/w % to about 95 w/w %, based on the total amount of the composition.

The additional stabilizer may be selected from mannitol, lactose, maltose, trehalose, dextran, glucose, and sucrose, and any composition thereof, preferably sucrose.

In some other embodiments, the composition is an aqueous composition in the liquid form, including a solution and an emulsion.

In some of such embodiments, the composition in the liquid form comprises the SN-38 existing in the form of nanocrystals and/or vesicles.

In some of such embodiments, the composition is in the form of a solution; and in some embodiments, the composition is in the form of an emulsion.

In some of such embodiments, based on the total amount of the composition, the content of the SN-38 is about 500.0 µg/mL to about 1.0 mg/mL, such as about 600 µg/mL to about 800 µg/mL.

In some of such embodiments, based on the total amount of the composition, the content of the albumin is about 5.0 mg/mL to about 10.0 mg/mL, such as about 6.0 mg/mL to about 10 mg/mL, or about 7.0 mg/mL to about 8.0 mg/mL.

In some embodiments, the nanoparticles in the composition have an average particle size of about 90 to 160 nm, such as about 95 to 150 nm, about 100 to 140 nm, about 105 to 130 nm, about 110 to 125 nm, about 110 nm, about 115 nm, about 120 nm, about 125 nm, about 130 nm, 135 nm, about 140 nm, or about 145 nm.

In some embodiments, the nanoparticles have a particle size distribution index (PDI) of not more than about 0.30, such as not more than about 0.2, not more than about 0.10, or not more than about 0.01.

In some embodiments, the composition has a Zeta potential of about −35 mV to about −20 mV, e.g., about −31 mV.

In some embodiments, when diluting (e.g., using 1×PBS at pH of about 7.4) the composition to result in a content of the SN-38 of about 4 µg/mL or lower, such as about 2 µg/mL or lower, about 1 µg/mL or lower, about 0.4 µg/mL or lower, about 0.1 µg/mL or lower, about 0.04 µg/mL or lower, about 0.02 µg/mL or lower, or about 0.01 µg/mL or lower, in the diluted composition, the nanoparticles do not undergo disintegration.

In some of such embodiments, the composition comprises no additional stabilizer. In some embodiments, the composition further comprises an additional stabilizer, wherein based on the total amount of the composition, the content of the additional stabilizer is at least about 2 w/v %, such as at least about 3 w/v %, at least about 5 w/v %, about 5 w/v % to about 30 w/v %, about 10 w/v % to about 25 w/v %, or about 15 w/v % to about 20 w/v %.

The additional stabilizer can be selected from mannitol, lactose, maltose, trehalose, dextran, glucose, and sucrose, and any composition thereof, preferably sucrose.

Open-ring SN-38 is the inactive form of the SN-38. The inventors have surprisingly found that in the composition of the present application, the open-ring SN-38 exists only in a very low amount. In some embodiments, the open-ring SN-38 in the composition accounts for about 2 w/w % or lower, preferably about 1.8 w/w % or lower, of the total amount of the SN-38.

The albumin acting as the carrier may form multimers, including dimers, trimers, multimers, and the like. The existence of the albumin multimers increases the risk of producing immunogenicity by a drug, in particular a drug parenterally administrated. Therefore, it is advantageous to contain as few albumin multimers as possible. The inventors have surprisingly found that an albumin multimer does not exist or substantially does not exist in the composition of the present application. Preferably, the albumin in a monomer form in the composition accounts for at least about 95 w/w %, preferably at least about 96%, more preferably at least about 98%, more preferably at least about 99%, at least about 99.2%, at least about 99.4%, or at least about 99.5%, of the total amount of the albumin. It can be expected that the composition of the present application has the advantages of low immunogenicity and therefore high safety.

The albumin that can be used in the present application is selected from human serum albumin (HSA), recombinant human albumin (rHA), bovine serum albumin, and porcine serum albumin. For example, the albumin comprises an amino acid sequence shown in SEQ ID NO: 1. Preferably, the albumin is selected from human serum albumin (HSA), recombinant human albumin (rHA).

In a second aspect, the present application provides a method for preparing the composition according to the first aspect as described above, characterized in that the method includes the following steps:
(1) dissolving the SN-38, the lipid, and the Span 20 in an organic solvent to form an organic phase; and preparing an aqueous solution of the albumin as an aqueous phase;
(2) mixing the organic phase and the aqueous phase to form an emulsion, wherein the emulsion comprises the nanoparticles, wherein in the nanoparticles, the albumin encapsulates at least part of the SN-38 and optionally at least part of the lipid; and
(3) removing the organic solvent in the emulsion to obtain a product comprising the nanoparticles.

In some embodiments, the method includes the following steps:
(1) dissolving the SN-38, the lipid, and the Span 20 using a mixed organic solvent comprising a first organic solvent selected from DMSO and a $C_{1-3}$ alcohol and a second organic solvent selected from $CHCl_3$ and a mixture of $CH_2Cl_2$ and $CHCl_3$ to form an organic phase; and preparing an aqueous solution of the albumin as an aqueous phase;
(2) mixing the organic phase and the aqueous phase to prepare an emulsion, wherein the emulsion comprises the nanoparticles, wherein in the nanoparticles, the albumin encapsulates at least part of the SN-38 and optionally at least part of the lipid;
(3) removing the organic solvents; and
(4) optionally, sterilizing the product obtained in step (3).

In some preferred embodiments, in the mixed organic solvent in step (1), a volume ratio of the second organic solvent to the DMSO or $C_{1-3}$ alcohol is about 1:20 (v/v) to about 20:1 (v/v), such as about 1:5 to about 5:1 (v/v), about 1:2 to about 4:1 (v/v), about 1:1 to about 4:1 (v/v), about 1.5:1 (v/v) to about 3:1 (v/v), or about 2:1 (v/v) to 7:3 (v/v).

In some preferred embodiments, in step (2), the organic phase:the aqueous phase is about 1:2 (v/v) to about 1:50 (v/v), such as about 1:5 (v/v) to about 1:20 (v/v), about 1:7 (v/v) to about 1:15 (v/v), 1:10 (v/v) to about 1:12 (v/v), e.g., about 1:5 (v/v) to about 1:12 (v/v), about 1:5 (v/v) to about 1:12 (v/v), about 1:6 (v/v), about 1:7 (v/v), or about 1:10 (v/v).

In some preferred embodiments, step (2) includes the following steps:
(2-1) dispersing the organic phase in the aqueous phase under shearing to obtain a crude emulsion; and
(2-2) homogenizing the crude emulsion under a high pressure to obtain a fine emulsion comprising the nanoparticles.

The $C_{1-3}$ alcohol includes methanol, ethanol, and isopropanol, and any combination thereof, for example, is ethanol (EtOH).

In some embodiments, the mixed organic solvent comprises the second organic solvent and EtOH at about 7:3 (v/v). In some embodiments, the mixed organic solvent comprises the second organic solvent of and DMSO at about 1:1 (v/v).

In some further embodiments, the invention provides the method as described above, wherein the method includes the following steps:
(1) dissolving the SN-38, the lipid, and the Span 20 using the mixed organic solvent of the second organic solvent/DMSO at 1:1 (v/v) or the mixed organic solvent of the second organic solvent/EtOH at 7:3 (v/v) to form the organic phase; and preparing the aqueous solution of the albumin as the aqueous phase;
(2) mixing the organic phase and the aqueous phase at a ratio of about 1:10 (v/v) to about 1:15 (v/v), e.g., about 1:12 (v/v), to prepare the emulsion, wherein the emulsion comprises the nanoparticles, wherein in the nanoparticles, the albumin encapsulates at least part of the SN-38 and optionally at least part of the lipid;
(3) removing the organic solvents; and
(4) optionally, sterilizing the product obtained in step (3).

In some embodiments, the second organic solvent is $CHCl_3$. In some other embodiments, the second organic solvent is a mixture of $CH_2Cl_2$ and $CHCl_3$, wherein preferably, a volume ratio of $CH_2Cl_2$ to $CHCl_3$ in the mixture is about 2:5-1:1, preferably about 2:5. The use of the mixture of $CH_2Cl_2$ and $CHCl_3$ as the second organic solvent has the advantage of reducing the residual $CHCl_3$ level in the final product, thus reducing the limitation of the solvent residue on clinical dosage, as compared to $CHCl_3$ alone.

In some embodiments, the aqueous phase comprises no additional stabilizer.

In some other embodiments, the aqueous phase has already comprised an additional stabilizer; and in some other embodiments, the method further includes adding and additional stabilizer in step (2). For example, the additional stabilizer is in such an amount that the content of the additional stabilizer in the product obtained in step (3) or (4) is at least about 2 w/v %, such as at least about 3 w/v %, at least about 5 w/v %, about 5 w/v % to about 30 w/v %, about 10 w/v % to about 25 w/v %, or about 15 w/v % to about 20 w/v %. Preferably, the additional stabilizer can be selected from albumins (such as human serum albumin, recombinant human albumin, bovine serum albumin, and skim milk powder), monosaccharides, disaccharides, polysaccharides, mannitol, and any combination thereof, preferably selected from mannitol, lactose, maltose, trehalose, dextran, glucose, and sucrose, and any composition thereof, preferably is sucrose.

In some embodiments, the mixed organic solvent in step (1) is added to the aqueous phase before mixing the organic phase and the aqueous phase in step (2). For example, the volume of the added mixed solvent is equal to or smaller than that of the organic phase. For example, a volume ratio of the added mixed organic solvent to the organic phase is about 1:1 (v/v) to about 1:5 (v/v), such as about 1:2 (v/v) to about 1:4 (v/v) or about 1:3 (v/v).

In some embodiments, in the organic phase in step (1), the SN-38 has a concentration of about 5-17 mg/mL, such as about 5.25-12 mg/mL or about 7-12 mg/mL, e.g., about 10 mg/mL.

In some other embodiments, in the organic phase in step (1), the concentration of the SN-38 is 4-10 mg/mL, e.g., about 6-8 mg/mL.

In some embodiments, in the organic phase in step (1), the lipid has a concentration of about 3-50 mg/mL, such as about 5-45 mg/mL or about 7.5-30 mg/mL, about 10-25 mg/mL, or about 15-20 mg/mL.

In some other embodiments, in the organic phase in step (1), the concentration of the lipid is about 10-20 mg/mL, e.g., about 15 mg/mL.

In some embodiments, in the organic phase in step (1), the Span 20 has a concentration of about 0.3-6 mg/mL, such as about 0.3-2 mg/mL or about 0.6-1 mg/mL.

In some embodiments, in the aqueous phase, the albumin has a concentration of about 5-15 mg/mL, e.g., about 6-12 mg/mL, preferably about 6-10 mg/mL.

In some other embodiments, in the aqueous phase, the concentration of the albumin is about 8-30 mg/mL, such as about 12-20 mg/mL or about 16-18 mg/mL.

In some embodiments, the method includes step (4): sterilizing the product obtained in step (3). There is no particular limitation on methods for sterilization. In a preferred embodiment, the product obtained in step (3) is sterilized by filtering through a filter membrane of about 0.2 μm.

In some embodiments, the method further includes the following step:

(5) drying the product obtained in step (3) or (4), preferably by spray drying or lyophilizing, to provide a composition in a solid form, preferably a powder, and more preferably a lyophilized powder.

Preferably, the SN-38 exists in the composition in an amorphous and/or nanocrystal form, as measured by electron microscopy or X-ray diffraction (Cu-Kα) analysis.

In some further embodiments, step (5) further includes: adding an additional stabilizer to the product obtained in step (3) or (4) before drying, wherein the additional stabilizer is in such an amount that when the solid form obtained in step (5) is reconstituted to form an aqueous composition (including a solution and an emulsion), the additional stabilizer has a content of at least about 2 w/v %, such as at least about 3 w/v %, at least about 5 w/v %, about 5 w/v % to about 30 w/v %, about 10 w/v % to about 25 w/v %, or about 15 w/v % to about 20 w/v %.

The additional stabilizer can be selected from albumins (such as human serum albumin, recombinant human albumin, bovine serum albumin, and skim milk powder), monosaccharides, disaccharides, polysaccharides, mannitol, and any combination thereof, preferably selected from mannitol, lactose, maltose, trehalose, dextran, glucose, and sucrose, and any composition thereof, preferably is sucrose.

In a third aspect, the present application provides a method for preparing a composition comprising SN-38, a lipid, an albumin, and Span 20, characterized in that the method includes the following steps:

(1) dissolving the SN-38, the lipid, and the Span 20 in an organic solvent to form an organic phase; and preparing an aqueous solution of the albumin as an aqueous phase;

(2) mixing the organic phase and the aqueous phase to form an emulsion, wherein the emulsion comprises nanoparticles, wherein in the nanoparticles, the albumin encapsulates at least part of the SN-38 and optionally at least part of the lipid; and (3) removing the organic solvent in the emulsion to obtain a product containing the nanoparticles.

The embodiments of the method are as described above with respect to the method according to the second aspect.

In the methods according to the second and third aspects, part of the albumin can encapsulate part of the SN-38 to form the nanoparticles, or can encapsulate part of the lipid to form the nanoparticles. Therefore, in some embodiments, the compositions according to the first aspect and the fourth aspect hereinafter can comprise the nanoparticles formed by part of the albumin encapsulating part of the SN-38, and/or the nanoparticles formed by part of the albumin encapsulating part of the lipid.

In the fourth aspect, the present application provides a composition that can be prepared by the method according to the third aspect described above.

In a fifth aspect, the present application further provides a method for preparing a composition with improved properties, wherein the composition comprises SN-38, a lipid, and an albumin, and the albumin encapsulates at least part of the SN-38 and optionally at least part of the lipid to form nanoparticles, wherein the method is characterized in that Span 20 is added in the course of preparing the composition.

In some embodiments, the composition comprises no additional stabilizer.

In some embodiments, the improved properties include improved stability.

In some embodiments, when the composition is in a liquid form, the improved stability includes: reduced formation or content of an albumin multimer, and/or reduced particle size of the nanoparticles during the preparation, storage and/or use of the composition. Preferably, the albumin multimer does not exist or substantially does not exist in the composition, or the albumin multimer accounts for at most 5 w/w %, such as at most about 4%, at most about 2%, at most about 1.5%, at most about 1.2%, at most about 1.1%, at most about 1%, or at most about 0.8%, of the total amount of the albumin.

In some embodiments, the composition is as described in the first aspect above.

In some embodiments, the method includes the following steps:

(1) dissolving the SN-38, the lipid, and the Span 20 in an organic solvent to form an organic phase; and preparing an aqueous solution of the albumin as an aqueous phase;

(2) mixing the organic phase and the aqueous phase to form an emulsion, wherein the emulsion comprises the nanoparticles, wherein in the nanoparticles, the albumin encapsulates at least part of the SN-38 and optionally at least part of the lipid; and (3) removing the organic solvent in the emulsion to obtain a product comprising the nanoparticles.

Further, the embodiments of the method are as described above with respect to the method according to the second aspect.

In a sixth aspect, the present application provides a pharmaceutical composition comprising the composition described above and optionally a pharmaceutically acceptable carrier.

In a seventh aspect, the present application provides a pharmaceutical composition comprising the composition described above which has been dried and optional a pharmaceutically acceptable carrier. The drying is preferably lyophilizing or spray drying, more preferably lyophilizing. Preferably, the pharmaceutical composition is in a solid form, preferably a lyophilized powder. Preferably, the SN-38 exists in the composition in the amorphous and/or nanocrystal form.

There is no particular limitation on administration routes of the composition or the pharmaceutical composition of the present application. The administration routes that can be considered include but are not limited to oral, intranasal, topical, and parenteral administration. Preferably, the pharmaceutical composition is used for parenteral administration, including but not limited to intravenous, intraarterial, subcutaneous, intracutaneous, and intramuscular administration, more preferably administration by intravenous injection (e.g., bolus or infusion).

The selection of the pharmaceutically acceptable carrier depends on the dosage form of the drug or the pharmaceutical composition, which depends firstly on an administration route of the dosage form (e.g., a dosage form for oral, intranasal, intracutaneous, subcutaneous, topical, intramuscular, or intravenous administration) and secondly on the formula of the dosage form. For example, the pharmaceutically acceptable carrier may include water (e.g., water for injection), a buffer, an isotonic saline solution (e.g., phosphate buffer (PBS)), glucose, mannitol, dextrose, lactose, starch, magnesium stearate, cellulose, magnesium carbonate, 0.3% glycerin, hyaluronic acid, ascorbic acid, lactic acid, ethanol, polyalkylene glycol such as polyethylene glycol (e.g., polyethylene glycol 4000) or polypropylene glycol, triglyceride, etc.

In an eighth aspect, the present application provides use of the composition or the pharmaceutical composition described above in the manufacture of a medicament for treating an SN-38 sensitive tumor in a subject.

In a ninth aspect, the present application provides the composition or the pharmaceutical composition described above for use in treating an SN-38 sensitive tumor in a subject.

In a tenth aspect, the present application provides a method for treating an SN-38 sensitive tumor in a subject, which includes administering a therapeutically effective amount of the composition or the pharmaceutical composition described above to the subject.

In some embodiments, the subject is a mammal, including but not limited to mouse, rat, rabbit, guinea pig, dog, cat, sheep, cow, goat, and horse. In some embodiments, the individual is human.

"An SN-38 sensitive tumor" refers to a tumor responsive to the administration of the SN-38, and the response including reduction in tumor cells, reduction in tumor size, elimination of tumor metastasis, inhibition of tumor growth, and the like. Preferably, the SN-38 sensitive tumor is selected from colorectal cancer, small cell lung cancer, lymph cancer, breast cancer (preferably triple-negative breast cancer), esophageal cancer, gastric cancer, liver cancer, renal cancer, pancreatic cancer, uterine cancer, and ovarian cancer.

Experimental studies have indicated that after an antitumor drug is bond to an albumin, the antitumor effect of the drug can be significantly improved. For example, nano albumin-bound paclitaxel has tumor tissue selectivity and a unique transport mechanism, and an intratumor paclitaxel drug concentration increased by 33% as compared to paclitaxel in solution (Desai N, Trieu V, Yao Z, et al., Increased antitumor activity, intratumor paclitaxel concentrations, and endothelial cell transport of cremophor-free, albumin-bound paclitaxel, ABI-007, compared with cremophor-based paclitaxel, [J]. *Clinical cancer research*, 2006, 12(4): 1317-1324). The above result is produced due to the active tumor-targeting effect achieved by the bonding of the gp60 receptors in the tumor tissue to the albumin, and the passive tumor-targeting effect achieved by the EPR effect of the drug-albumin conjugate nanoparticles, after the drug is bound to the albumin. Thus, the drug distribution in the tumor is greatly increased, the therapeutic effect is improved, and the toxic and side effects are reduced. It can be expected that the composition or the pharmaceutical composition of the present application has advantageous antitumor efficacy. By preliminary experiments, the inventors have found that the composition of the present application has antitumor activity superior to that of the commercially available irinotecan hydrochloride injection.

In an eleventh aspect, the present application provides a kit comprising the composition or the pharmaceutical composition described above. Where necessary, the kit may further comprise an instruction, a package, and a container for accommodating the composition or the pharmaceutical composition.

Although the embodiments of the invention have been described with the SN-38 as the active ingredient in the above first to eleventh aspects, these are merely one aspect of the concept of the invention. The concept of the invention further contemplates the technical solutions with other camptothecin drugs as active ingredients. It is expected that the above embodiments are still applicable when the SN-38 is replaced with other camptothecin drugs. In other words, the present application further includes any and all embodiments described in any one of the first to eleventh aspects above, except that the SN-38 is replaced with other camptothecin drugs, unless there is a conflict in the context. The other camptothecin drugs may be selected from: irinotecan (CPT-11), 10-hydroxycamptothecine (HCPT), topotecan (TPT), rubitecan (9-NC), 9-aminocamptothecin (9-AC), belotecan (Cas. No.: 256411-32-2), Dxd (Cas. No.: 1599440-33-1), DX-8951 (exatecan), CKD602 (belotecan), lurtotecan, namitecan (Cas. No.: 372105-27-6), ST1481 (gimatecan, Cas. No.: 292618-32-7), BNP-1350 (Cas. No. 203923-89-1), and BN80915 (diflomotecan). A person skilled in the art will appreciate that such embodiments may also achieve the beneficial effects as described hereinafter.

The embodiments of the invention as described in the Contents of the Invention of the present application include:

Embodiment 1. A composition, comprising SN-38, a lipid, an albumin, and Span 20, characterized in that the composition comprises nanoparticles, wherein in the nanoparticles, the albumin encapsulates at least part of the SN-38 and optionally at least part of the lipid;

lipid:SN-38 is about (0.1-10):1 (w:w), about (0.5-6):1 (w:w), about (0.5-5):1 (w:w), about (0.5-3):1 (w:w), about (1-4):1 (w:w), about (1.2-4):1 (w:w), about (1.4-2):1 (w:w), about (1.5-2.5):1 (w:w), or about 1:1;

albumin:SN-38 is about (1-100):1 (w:w), about (1-50):1 (w:w), about (3-25):1 (w:w), about (5-25):1 (w:w), about (5-20):1 (w:w), about (5-18):1 (w:w), about (6-15):1 (w:w), about (7-15):1 (w:w), about (6-12):1 (w:w), about (7-12):1 (w:w), about (9-11):1 (w:w), or about 10:1 (w:w); and Span 20:SN-38 is about (3-60):100 (w:w), about (4-60):100 (w:w), about (5-60):100 (w:w), about (6-60):100 (w:w), about (7-55):100 (w:w), about (8-50):100 (w:w), about (10-45):100 (w:w), about (12-40):100 (w:w), about (14-35):100 (w:w), about (15-30):100 (w:w), about (16-25):100 (w:w), or about (18-20):100 (w:w); and wherein the lipid is selected from cholesterol, cholesterol derivatives, cholesterol analogues, and fatty acid esters, and any combination of two or more of them.

Embodiment 2. The composition of Embodiment 1, characterized in that albumin:lipid is about (1-100):1 (w:w), such as about (2-20):1 (w:w), about (3-15):1 (w:w), about (5-10):1 (w:w), about 7:1 (w:w), or about 10:1 (w:w).

Embodiment 3. The composition of Embodiment 1 or 2, characterized in that, based on the total amount of the SN-38, the lipid, and the albumin in the composition, the SN-38 has a content of about 1 w/w % to about 25 w/w %; and/or the lipid has a content of about 1 w/w % to about 35 w/w %; and/or the albumin has a content of about 50 w/w % to about 98 w/w %;

or, the content of the SN-38 is about 3 w/w % to about 20 w/w %; and/or the content of the lipid is about 2 w/w % to about 30 w/w %; and/or the content of the albumin is about 55 w/w % to about 95 w/w %;

or, the content of the SN-38 is about 3 w/w % to about 15 w/w %, about 4 w/w %, about 5 w/w %, about 6 w/w %, about 6.5 w/w %, about 7 w/w %, about 7.5 w/w %, about 8 w/w %, about 8.5 w/w %, about 9 w/w %, about 10 w/w %, about 11 w/w %, about 12 w/w %, about 13 w/w %, or about 14 w/w %; and/or the content of the lipid is about 3 w/w % to about 30 w/w %, about 4 w/w %, about 5 w/w %, about 6 w/w %, about 7 w/w %, about 8 w/w %, about 8.5 w/w %, about 9 w/w %, about 9.5 w/w %, about 10 w/w %, about 10.5 w/w %, about 11 w/w %, about 11.5 w/w %, about 12 w/w %, about 12.5 w/w %, about 13 w/w %, about 13.5 w/w %, about 14 w/w %, about 15 w/w %, about 16 w/w %, about 17 w/w %, about 18 w/w %, about 19 w/w %, about 20 w/w %, about 21 w/w %, about 24 w/w %, about 26 w/w %, or about 28 w/w %; and/or the content of the albumin is about 60 w/w % to about 94 w/w %, about 64 w/w % to about 93 w/w %, about 66 w/w % to about 92 w/w %, about 68 w/w % to about 91 w/w %, about 70 w/w % to about 90 w/w %, about 75 w/w % to about 90 w/w %, about 76 w/w %, about 77 w/w %, about 78 w/w %, about 79 w/w %, about 80 w/w %, about 81 w/w %, about 82 w/w %, about 83 w/w %, about 84 w/w %, about 85 w/w %, about 86 w/w %, about 87 w/w %, about 88 w/w %, or about 89 w/w %.

Embodiment 4. The composition of any one of Embodiments 1 to 3, characterized in that, the Span 20 has a content of about 0.03 w/w % to about 12 w/w %, about 0.06 w/w % to about 10 w/w %, 0.08 w/w % to about 9 w/w %, about 0.1 w/w % to about 8 w/w %, about 0.2 w/w % to about 7 w/w %, about 0.4 w/w % to about 6 w/w %, about 0.6 w/w % to about 5 w/w %, about 0.8 w/w % to about 4 w/w %, or about 1 w/w % to about 2 w/w %, based on the total amount of the SN-38, the lipid, the albumin, and the Span 20 in the composition.

Embodiment 5. The composition of any one of Embodiments 1 to 4, characterized in that:

lipid:SN-38 is about (1-10):1 (w:w), about (1-8):1 (w:w), about (1-6):1 (w:w), about (1-5):1 (w:w), about (1-4.5):1 (w:w), about (1-4):1 (w:w), about (1.2-3.8):1 (w:w), about (1.4-3.6):1 (w:w), about (1.6-3.4):1 (w:w), about (1.8-3.2):1 (w:w), about (2-3):1 (w:w), about (2.2-2.8):1 (w:w), about (2.4-2.6):1 (w:w), about 1:1 (w:w), about 2.5:1 (w:w), or about (0.8-1.8):1 (w:w), about (0.9-1.7):1 (w:w), or about (1-1.4):1; and/or albumin:SN-38 is about (5-40):1 (w:w), about (5 to less than 40):1 (w:w), about (5-35):1 (w:w), about (5-30):1 (w:w), about (8-25):1 (w:w), about (10-22.5):1 (w:w), about (12.5-20):1 (w:w), about (15-17.5):1 (w:w), about (16-18):1 (w:w), about 10:1 (w:w), or about (9-21):1 (w:w), about (9-20):1 (w:w), about (11-18):1 (w:w), or about (11.1-17.3):1 (w:w); and/or Span 20:SN-38 is about (5-60):100 (w:w), about (6-60):100 (w:w), about (7-55):100 (w:w), about (8-50):100 (w:w), about (10-45):100 (w:w), about (12-40):100 (w:w), about (14-35):100 (w:w), about (15-30):100 (w:w), about (16-25):100 (w:w), about (18-20):100 (w:w), or about (5-10):100 (w:w), about (5-9):100 (w:w), about (6-8.6):100 (w:w), about (6-8):100 (w:w), or about (6.5-7):100 (w:w); and/or albumin:lipid is about (1-40):1 (w:w), about (1 to less than 40):1 (w:w), about (2-35):1 (w:w), about (3-15):1 (w:w), about (5-10):1 (w:w), about (6-8):1 (w:w), or about 7:1 (w:w), or about (6-21):1 (w:w), about (6.7-13):1 (w:w), about (7-13):1 (w:w), or about (11-12.7):1 (w:w).

Embodiment 6. The composition of any one of Embodiments 1 to 5, characterized in that, based on the total amount of the SN-38, the lipid, and the albumin in the composition, the content of the SN-38 is about 2 w/w % to about 16 w/w %; and/or the content of the lipid is about 2 w/w % to about 35 w/w %; and/or the content of the albumin is about 75 w/w % to about 96 w/w %;

or, the content of the SN-38 is about 2.5 w/w % to about 15 w/w %, about 4 w/w % to about 10 w/w %, about 4.5 w/w % to about 9.5 w/w %, about 5 w/w % to about 9 w/w %, or about 7.5 w/w % to about 8 w/w %; and/or the content of the lipid in the composition is about 2.5 w/w % to about 30 w/w %, about 4 w/w % to about 12.5 w/w %, about 4.5 w/w % to about 12 w/w %, about 7 w/w % to about 10 w/w %, or about 7.5 w/w % to about 8 w/w %; and/or the content of the albumin in the composition is about 76 w/w % to about 95 w/w %, about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %;

or, the content of the SN-38 is about 3 w/w % to about 14 w/w %, about 3.5 w/w % to about 12 w/w %, about 4 w/w %, about 4.2 w/w %, about 4.5 w/w %, about 4.6 w/w %, about 4.8 w/w %, about 5 w/w %, about 5.5 w/w %, about 6 w/w %, about 6.5 w/w %, about 7 w/w %, about 7.5 w/w %, about 7.6 w/w %, about 7.8 w/w %, about 8 w/w %, about 8.5 w/w %, about 9 w/w %, about 9.2 w/w %, about 9.5 w/w %, about 9.6 w/w %, about 9.8 w/w %, about 10 w/w %, about 10.5 w/w %, about 11 w/w %, or about 11.5 w/w %; and/or the content of the lipid is about 4 w/w % to about 25 w/w %, about 4.5 w/w % to about 20 w/w %, about 4.3 w/w %, about 4.5 w/w %, about 4.7 w/w %, about 5 w/w %, about 5.5 w/w %, about 6 w/w %, about 6.5 w/w %, about 6.7 w/w %, about 6.9 w/w %, about 7 w/w %, about 7.5 w/w %, about 7.6 w/w %, about 7.8 w/w %, about 8 w/w %, about 8.5 w/w %, about 9 w/w %, about 9.5 w/w %, about 10 w/w %, about 10.5 w/w %, about 11 w/w %, about 11.5 w/w %, about 12 w/w %, about 12.1 w/w %, about 12.3 w/w %, about 12.5 w/w %, about 13 w/w %, about 13.5 w/w %, about 14 w/w %, about 14.5 w/w %, about 15 w/w %, about 15.5 w/w %, about 16 w/w %, about 16.5 w/w %, about 17 w/w %, about 17.5 w/w %, about 18 w/w %, about 18.5 w/w %, about 19 w/w %, or about 19.5 w/w %; and/or the content of the albumin is about 78 w/w % to about 92 w/w %, about 79 w/w %, about 79.2 w/w %, about 79.4 w/w %, about 79.6 w/w %, about 79.8 w/w %, about 80 w/w %, about 81 w/w %, about 82 w/w %, about 83 w/w %, about 84 w/w %, about 84.3 w/w %, about 84.5 w/w %, about 84.7 w/w %, about 84.9 w/w %, about 85 w/w %, about 86 w/w %, about 87 w/w %, about 87.3 w/w %, about 87.5 w/w %, about 87.7 w/w %, about 87.9 w/w %, about 88 w/w %, about 89 w/w %, about 90 w/w %, about 91 w/w %, about 91.3 w/w %, or about 91.5 w/w %.

Embodiment 7. The composition of any one of Embodiments 1 to 6, characterized in that, based on the total amount of the SN-38, the lipid, the albumin, and the Span 20 in the composition, the content of the Span 20 is about 0.14 w/w % to about 5 w/w %, about 0.2 w/w % to about 2.5 w/w %, about 0.22 w/w % to about 2.0 w/w %, about 0.24 w/w % to about 2 w/w %, about 0.26 w/w % to about 1.5 w/w %, about 0.28 w/w % to about 1.0 w/w %, about 0.3 w/w % to about 0.9 w/w %, about 0.32 w/w % to about 0.8 w/w %, about 0.34 w/w % to about 0.7 w/w %, about 0.36 w/w % to about 0.6 w/w %, about 0.38 w/w % to about 0.58 w/w %, about 0.4 w/w % to about 0.56 w/w %, about 0.42 w/w % to about 0.54 w/w %, about 0.44 w/w % to about 0.52 w/w %, about 0.46 w/w %, about 0.48 w/w %, about 0.5 w/w %, about 0.2 w/w % to about 0.8 w/w %, about 0.24 w/w % to about 0.7 w/w %, about 0.26 w/w % to about 0.7 w/w %, about 0.3 w/w % to about 0.65 w/w %, about 0.36 w/w % to about 0.6 w/w %, about 0.4 w/w % to about 0.58 w/w %, about 0.44 w/w % to about 0.56 w/w %, about 0.48 w/w % to about 0.54 w/w %, or about 0.5 w/w % to about 0.52 w/w %.

Embodiment 8. The composition of any one of Embodiments 1 to 7, characterized in that:
the SN-38 existing in the nanoparticles accounts for at least about 1 w/w % or at least about 2 w/w %, such as at least about 3 w/w %, about 3 w/w % to about 13 w/w %, about 4 w/w % to about 12 w/w %, about 4 w/w %, about 5 w/w %, about 6 w/w %, about 7 w/w %, about 8 w/w %, about 9 w/w %, about 10 w/w %, or about 11 w/w %, of the total amount of the SN-38, the lipid, and the albumin in the composition; and/or
the SN-38 existing in the nanoparticles accounts for about 80 w/w % to about 99 w/w %, such as about 88 w/w % to about 98 w/w %, about 89 w/w %, about 90 w/w %, about 91 w/w %, about 92 w/w %, about 93 w/w %, about 94 w/w %, about 95 w/w %, about 96 w/w %, or about 97 w/w %, of the total amount of the SN-38 in the composition.

Embodiment 9. The composition of any one of Embodiments 1 to 8, characterized in that:
the cholesterol derivatives are selected from esters formed by cholesterol and organic acids, including cholesteryl palmitate, cholesteryl caprylate, and a combination thereof; and/or
the cholesterol analogues are selected from vitamin D2, vitamin D3, and a combination thereof; and/or
the fatty acid esters are selected from fatty acid glycerides, such as long-chain fatty acid glycerides, including glyceryl stearate, e.g., glyceryl monostearate.

Embodiment 10. The composition of any one of Embodiments 1 to 9, characterized in that the lipid is cholesterol.

Embodiment 11. The composition of Embodiment 10, characterized in that:
cholesterol:SN-38 is about (1-6):1 (w:w), about (1.2-5):1 (w:w), about (1.4-4):1 (w:w), about 3:1 (w:w), about 2:1 (w:w), about 1:1 (w:w), or about (0.8-1.8):1 (w:w), about (0.9-1.7):1 (w:w), or about (1-1.4):1; and/or
albumin:SN-38 is about (3-25):1 (w:w), about (4-20):1 (w:w), about (5-15):1 (w:w), about (6-12):1 (w:w), about (7-12):1 (w:w), about (9-11):1 (w:w), or about 10:1 (w:w), or about (9-21):1 (w:w), about (9-20):1 (w:w), about (11-18):1 (w:w), or about (11.1-17.3):1 (w:w); and/or
albumin:cholesterol is about (2-20):1 (w:w), about (3-15):1 (w:w), about (5-10):1 (w:w), or about 7:1 (w:w), or about (6-21):1 (w:w), about (6.7-13):1 (w:w), about (7-13):1 (w:w), or about (11-12.7):1 (w:w); and/or
based on the total amount of the SN-38, the cholesterol, and the albumin in the composition,
the content of the SN-38 is about 3 w/w % to about 15 w/w %, about 4 w/w % to about 15 w/w %, about 6 w/w % to about 10 w/w %, or about 8 w/w % to about 12 w/w %, or about 4 w/w % to about 10 w/w %, about 4.5 w/w % to about 9.5 w/w %, about 5 w/w % to about 9 w/w %, or about 7.5 w/w % to about 8 w/w %; and/or
the content of the cholesterol is about 5 w/w % to about 25 w/w %, about 6 w/w % to about 22 w/w %, about 15 w/w % to about 20 w/w %, or about 4 w/w % to about 12.5 w/w %, about 4.5 w/w % to about 12 w/w %, about 7 w/w % to about 10 w/w %, or about 7.5 w/w % to about 8 w/w %; and/or
the content of the albumin is about 64 w/w % to about 90 w/w %, about 70 w/w % to about 90 w/w %, or about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %; and/or
the SN-38 existing in the nanoparticles accounts for at least about 3 w/w %, such as about 3 w/w % to about 13 w/w %, about 4 w/w % to about 12 w/w %, about 4 w/w %, about 5 w/w %, about 6 w/w %, about 7 w/w %, about 8 w/w %, about 9 w/w %, about 10 w/w %, or about 11 w/w %, of the total amount of the SN-38, the cholesterol, and the albumin in the composition.

Embodiment 12. The composition of Embodiment 10, wherein:
cholesterol:SN-38 is about (1-3):1 (w:w), about (1.2-2.5):1 (w:w), about (1.4-2):1 (w:w), about (1.5-2):1 (w:w), about (1.3-1.8):1 (w:w), about (1.4-1.6):1 (w:w), about (1.5-1.7):1 (w:w), about (1.2-1.5):1

(w:w), about 1:1 (w:w), about (1.4-1.5):1 (w:w), or about (0.8-1.8):1 (w:w), about (0.9-1.7):1 (w:w), or about (1-1.4):1;

albumin:SN-38 is about (5-15):1 (w:w), about (5-12):1 (w:w), about (6-12):1 (w:w), or about (7-12):1 (w:w), about (9-11):1 (w:w), about (10-12):1 (w:w), about 11:1 (w:w), or about (9-21):1 (w:w), about (9-20):1 (w:w), about (11-18):1 (w:w), or about (11.1-17.3):1 (w:w); and albumin:cholesterol is about (3-10):1 (w:w), about (4-8):1 (w:w), about (5-7):1 (w:w), or about (6-21):1 (w:w), about (6.7-13):1 (w:w), about (7-13):1 (w:w), or about (11-12.7):1 (w:w).

Embodiment 13. The composition of Embodiment 12, characterized in that, based on the total amount of the SN-38, the cholesterol, and the albumin in the composition, the content of the SN-38 is about 6 w/w % to about 14 w/w %, about 6.5 w/w % to about 13 w/w %, about 7 w/w % to about 12 w/w %, about 7.5 w/w % to about 12 w/w %, about 8 w/w % to about 11 w/w %, about 8.5 w/w % to about 10 w/w %, about 9 w/w %, or about 4 w/w % to about 10 w/w %, about 4.5 w/w % to about 9.5 w/w %, about 5 w/w % to about 9 w/w %, or about 7.5 w/w % to about 8 w/w %; and/or the content of the cholesterol is about 8 w/w % to about 18 w/w %, about 8.5 w/w % to about 17 w/w %, about 9 w/w % to about 16 w/w %, about 9.5 w/w % to about 16 w/w %, about 10 w/w % to about 16 w/w %, about 10.5 w/w % to about 16 w/w %, about 11 w/w % to about 15 w/w %, about 11.5 w/w % to about 15 w/w %, about 12 w/w % to about 15 w/w %, about 12.5 w/w % to about 14 w/w %, about 13 w/w % to about 13.5 w/w %, or about 4 w/w % to about 12.5 w/w %, about 4.5 w/w % to about 12 w/w %, about 7 w/w % to about 10 w/w %, or about 7.5 w/w % to about 8 w/w %; and/or the content of the albumin is about 66 w/w % to about 90 w/w %, about 68 w/w % to about 89 w/w, about 70 w/w % to about 88 w/w %, about 70 w/w % to about 87 w/w %, about 70 w/w % to about 86 w/w %, about 70 w/w % to about 85 w/w %, about 75 w/w % to about 85 w/w %, about 76 w/w %, about 77 w/w %, about 78 w/w %, about 79 w/w %, 80 w/w %, 81 w/w %, about 82 w/w %, about 83 w/w %, about 84 w/w %, about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %.

Embodiment 14. The composition of Embodiment 10, characterized in that:

cholesterol:SN-38 is about (1-5):1 (w:w), about (1-4.5):1 (w:w), about (1-4):1 (w:w), about (1.2-3.8):1 (w:w), about (1.4-3.6):1 (w:w), about (1.6-3.4):1 (w:w), about (1.8-3.2):1 (w:w), about (2-3):1 (w:w), about (2.2-2.8):1 (w:w), about (2.4-2.6):1 (w:w), about 2.5:1 (w:w), about 1:1 (w:w), or about (0.8-1.8):1 (w:w), about (0.9-1.7):1 (w:w), or about (1-1.4):1; and/or albumin:SN-38 is about (5-25):1 (w:w), about (5-20):1 (w:w), about (6-19):1 (w:w), about (7-18):1 (w:w), about (8-16):1 (w:w), about (9-14):1 (w:w), or about (10-12):1 (w:w), or about (9-21):1 (w:w), about (9-20):1 (w:w), about (11-18):1 (w:w), or about (11.1-17.3):1 (w:w); and/or albumin:cholesterol is about (5-25):1 (w:w), about (6-20):1 (w:w), about (7-18):1 (w:w), about (8-16):1 (w:w), about (9-14):1 (w:w), about (10-12):1 (w:w), or about (9-21):1 (w:w), about (6.7-13):1 (w:w), about (7-13):1 (w:w), or about (11-12.7):1 (w:w); and/or Span 20:SN-38 is about (5-40):100 (w:w), about (6-30):100 (w:w), about (7-25):100 (w:w), about (8-20):100 (w:w), about (9-15):100 (w:w), about (10-12):100 (w:w), or about (5-10):100 (w:w), about (5-9):100 (w:w), about (6-8.6):100 (w:w), about (6-8):100 (w:w), or about (6.5-7):100 (w:w); and/or based on the total amount of the SN-38, the cholesterol, and the albumin in the composition, the content of the SN-38 is about 3 w/w % to about 10 w/w %, about 3.5 w/w % to about 9.5 w/w %, about 4 w/w %, about 4.5 w/w %, about 5 w/w %, about 5.5 w/w %, about 6 w/w %, about 6.5 w/w %, about 7 w/w %, about 7.5 w/w %, about 8 w/w %, about 8.5 w/w %, about 9 w/w %, or about 4 w/w % to about 10 w/w %, about 4.5 w/w % to about 9.5 w/w %, about 5 w/w % to about 9 w/w %, or about 7.5 w/w % to about 8 w/w %; and/or the content of the cholesterol is about 4 w/w % to about 18 w/w %, about 4.5 w/w % to about 17.5 w/w %, about 5 w/w %, about 5.5 w/w %, about 6 w/w %, about 6.5 w/w %, about 7 w/w %, about 7.5 w/w %, about 8 w/w %, 8.5 w/w %, about 9 w/w %, about 9.5 w/w %, about 10 w/w %, about 10.5 w/w %, about 11 w/w %, about 11.5 w/w %, about 12 w/w %, about 12.5 w/w %, about 13 w/w %, about 13.5 w/w %, about 14 w/w %, about 14.5 w/w %, about 15 w/w %, about 15.5 w/w %, about 16 w/w %, about 16.5 w/w %, about 17 w/w %, or about 4 w/w % to about 12.5 w/w %, about 4.5 w/w % to about 12 w/w %, about 7 w/w % to about 10 w/w %, or about 7.5 w/w % to about 8 w/w %; and/or the content of the albumin is about 78 w/w % to about 92 w/w %, about 79 w/w %, about 80 w/w %, about 81 w/w %, about 82 w/w %, about 83 w/w %, about 84 w/w %, about 85 w/w %, about 86 w/w %, about 87 w/w %, about 88 w/w %, about 89 w/w %, about 90 w/w %, about 91 w/w %, or about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %.

Embodiment 15. The composition of any one of Embodiments 12 to 14, characterized in that:

the SN-38 existing in the nanoparticles accounts for at least about 6 w/w % to about 12 w/w %, such as about 7 w/w % to about 11 w/w %, about 8 w/w % to about 10 w/w %, about 8.3%, or about 9 w/w %, of the total amount of the SN-38, the cholesterol, and the albumin in the composition; and/or the SN-38 existing in the nanoparticles accounts for about 95 w/w % to about 99 w/w %, such as about 96 w/w % to about 99 w/w %, about 97 w/w % to about 99 w/w %, about 98 w/w % to about 99 w/w %, about 99 w/w % or higher, of the total amount of the SN-38 in the composition.

Embodiment 16. The composition of any one of Embodiments 1 to 15, characterized in that the composition is in a liquid, semisolid, or solid form.

Embodiment 17. The composition of any one of Embodiments 1 to 16, characterized in that the composition is in the solid form, preferably a powder form, more preferably a lyophilized powder;

preferably, the SN-38 exists in the composition in an amorphous and/or nanocrystal form.

Embodiment 18. The composition of any one of Embodiments 1 to 17, characterized in that the composition comprises no additional stabilizer; or preferably, the composition further comprises an additional stabilizer, e.g., a lyophilization stabilizer, wherein the additional stabilizer is in such an amount that, when the composition is reconstituted to form an aqueous composition (including a solution and an emulsion), the additional stabilizer has a content of at least about 2 w/v %, e.g., at least about 3 w/v %, such as at least about 5 w/v %, about 5 w/v % to about 30 w/v %, about 10 w/v % to about 25 w/v %, or about 15 w/v % to about 20 w/v %.

Embodiment 19. The composition of Embodiment 17 or 18, characterized in that the composition further comprises the additional stabilizer, and based on the total amount of the composition, the additional stabilizer has a content of about 60 w/w % to about 98 w/w %, such as about 65 w/w % to about 97 w/w %, about 68 w/w % to about 96 w/w %, about 69 w/w % to about 95 w/w %, about 70 w/w % to about 94 w/w %, about 71 w/w % to about 93 w/w %, about 72 w/w % to about 92 w/w %, about 73 w/w %, about 74 w/w %, about 75 w/w %, about 76 w/w %, about 77 w/w %, about 78 w/w %, about 79 w/w %, about 80 w/w %, about 81 w/w %, about 82 w/w %, about 83 w/w %, about 84 w/w %, about 85 w/w %, about 86 w/w %, about 87 w/w %, about 88 w/w %, about 89 w/w %, about 90 w/w %, or about 91 w/w %;

for example, the content of the additional stabilizer is about 70 w/w % to about 96 w/w %, about 70 w/w % to about 90 w/w %, about 72 w/w % to about 89 w/w %, about 74 w/w % to about 88 w/w %, about 76 w/w % to about 87 w/w %, or about 80 w/w % to about 96 w/w %, about 80 w/w % to about 86 w/w %, about 81 w/w % to about 86 w/w %, about 82 w/w % to about 85 w/w %, about 83 w/w % to about 84 w/w %, or about 84 w/w % to about 95 w/w %.

Embodiment 20. The composition of Embodiment 18 or 19, wherein the additional stabilizer is selected from albumins (such as human serum albumin, recombinant human albumin, bovine serum albumin, and skim milk powder), monosaccharides, disaccharides, polysaccharides, mannitol, and any combination thereof, preferably selected from mannitol, lactose, maltose, trehalose, dextran, glucose, and sucrose, and any composition thereof, preferably is sucrose.

Embodiment 21. The composition of any one of Embodiments 17 to 20, wherein when the composition is reconstituted to form an aqueous composition (including a solution and an emulsion) at about 0.1 µg/mL to about 30.0 mg/mL, the nanoparticles have an average particle size of about 50 to 200 nm, such as about 90 to 150 nm, about 95 to 140 nm, about 100 to 130 nm, about 105 to 125 nm, or about 110 to 120 nm.

Embodiment 22. The composition of any one of Embodiments 1 to 16, characterized in that the composition is an aqueous composition in a liquid form, including a solution and an emulsion; and in particular, the composition in the liquid form comprises the SN-38 in the form of nanocrystals and/or vesicles.

Embodiment 23. The composition of Embodiment 22, characterized in that, based on the total amount of the composition, the content of the SN-38 is about 0.1 µg/mL to about 30.0 mg/mL, about 0.2 µg/mL to about 27.0 mg/mL, about 0.5 µg/mL to about 24.0 mg/mL, about 1.0 µg/mL to about 21.0 mg/mL, about 5.0 µg/mL to about 18.0 mg/mL, about 10.0 µg/mL to about 15.0 mg/mL, about 20.0 µg/mL to about 12 mg/mL, about 25.0 µg/mL to about 9 mg/mL, about 50.0 µg/mL to about 6.0 mg/mL, or about 100.0 µg/mL to about 3.0 mg/mL; and/or the content of the lipid is about 0.05 µg/mL to about 100.0 mg/mL, about 0.1 µg/mL to about 90.0 mg/mL, about 0.25 µg/mL to about 80.0 mg/mL, about 0.5 µg/mL to about 70.0 mg/mL, about 2.5 µg/mL to about 60.0 mg/mL, about 5.0 µg/mL to about 50.0 mg/mL, about 10.0 µg/mL to about 40.0 mg/mL, about 12.5 µg/mL to about 30.0 mg/mL, about 25.0 µg/mL to about 20.0 mg/mL, or about 50.0 µg/mL to about 10.0 mg/mL; and/or the content of the albumin is about 3.0 µg/mL to about 300.0 mg/mL, about 6.0 µg/mL to about 270.0 mg/mL, about 15.0 µg/mL to about 240.0 mg/mL, about 30.0 µg/mL to about 210.0 mg/mL, about 150.0 µg/mL to about 180.0 mg/mL, about 300.0 µg/mL to about 150.0 mg/mL, about 600.0 µg/mL to about 120.0 mg/mL, about 750.0 µg/mL to about 90.0 mg/mL, about 1500.0 µg/mL to about 60.0 mg/mL, or about 3.0 mg/mL to about 30.0 mg/mL.

Embodiment 24. The composition of Embodiment 22 or 23, characterized in that, based on the total amount of the composition, the content of the SN-38 is about 100.0 µg/mL to about 3.0 mg/mL, such as about 200.0 µg/mL to about 2.5 mg/mL, about 300.0 µg/mL to about 2.0 mg/mL, about 400.0 µg/mL to about 1.5 mg/mL, about 500.0 µg/mL to about 1.0 mg/mL, or about 600 µg/mL to about 800 µg/mL; and/or the content of the lipid is about 50.0 µg/mL to about 10.0 mg/mL, such as about 100.0 µg/mL to about 8.0 mg/mL, about 200.0 µg/mL to about 6.0 mg/mL, about 300.0 µg/mL to about 4.0 mg/mL, about 400.0 µg/mL to about 3.0 mg/mL, about 500.0 µg/mL to about 2.5 mg/mL, about 600.0 µg/mL to about 2.0 mg/mL, about 700.0 µg/mL to about 1.5 mg/mL, about 800 µg/mL to about 1.0 mg/mL, or about 200 µg/mL to about 1.5 mg/mL; and/or the content of the albumin is about 3.0 mg/mL to about 30.0 mg/mL, such as about 4.0 mg/mL to about 25.0 mg/mL, about 5.0 mg/mL to about 20.0 mg/mL, about 6.0 mg/mL to about 15.0 mg/mL, about 7.0 mg/mL to about 12.0 mg/mL, or about 8.0 mg/mL to about 10.0 mg/mL.

Embodiment 25. The composition of any one of Embodiments 22 to 24, characterized in that the nanoparticles have an average particle size of about 50 to 200 nm, such as about 90 to 150 nm, about 95 to 140 nm, about 100 to 130 nm, about 105 to 125 nm, or about 110 to 120 nm.

Embodiment 26. The composition of any one of Embodiments 22 to 25, characterized in that after storage at 4° C. for 24 h, the nanoparticles have an average particle size of about 50 to 200 nm, such as about 90 to 150 nm or about 100 to 130 nm.

Embodiment 27. The composition of any one of Embodiments 22 to 26, characterized in that the nanoparticles have a particle size distribution index (PDI) of not more than about 0.30, such as not more than about 0.2, not more than about 0.10, or not more than about 0.01.

Embodiment 28. The composition of any one of Embodiments 22 to 27, characterized in that the composition has a Zeta potential of about −35 mV to about −20 mV, e.g., about −31 mV.

Embodiment 29. The composition of any one of Embodiments 22 to 28, characterized in that when diluting (e.g., using 1×PBS at pH of about 7.4) the composition to result in a content of the SN-38 of about 4 µg/mL or lower, such as about 2 µg/mL or lower, about 1 µg/mL or lower, about 0.4 µg/mL or lower, about 0.1 µg/mL or lower, about 0.04 µg/mL or lower, about 0.02 µg/mL or lower, or about 0.01 µg/mL or lower, in the diluted composition, the nanoparticles do not undergo disintegration.

Embodiment 30. The composition of any one of Embodiments 22 to 29, characterized in that the composition comprises no additional stabilizer; or
preferably, the composition further comprises an additional stabilizer, wherein based on the total amount of the composition, the content of the additional stabilizer is at least about 2 w/v %, such as at least about 3 w/v %, at least about 5 w/v %, about 5 w/v % to about 30 w/v %, about 10 w/v % to about 25 w/v %, or about 15 w/v % to about 20 w/v %.

Embodiment 31. The composition of Embodiment 30, wherein the additional stabilizer is selected from albumins (such as human serum albumin, recombinant human albumin, bovine serum albumin, and skim milk powder), monosaccharides, disaccharides, polysaccharides, mannitol, and any combination thereof, preferably selected from mannitol, lactose, maltose, trehalose, dextran, glucose, and sucrose, and any composition thereof, preferably is sucrose.

Embodiment 32. The composition of any one of Embodiments 1 to 31, which is characterized in that the open-ring SN-38 in the composition accounts for about 2 w/w % or lower, such as about 1.8 w/w % or lower, of the total amount of the SN-38; and/or
an albumin multimer does not exist or substantially does not exist in the composition; for example, the albumin in a monomer form in the composition accounts for at least about 95 w/w, such as at least about 96%, at least about 98%, at least about 99%, at least about 99.2%, at least about 99.4%, or at least about 99.5%, of the total amount of the albumin.

Embodiment 33. The composition of any one of Embodiments 1 to 32, characterized in that the albumin is selected from human serum albumin (HSA), recombinant human albumin (rHA), bovine serum albumin, and porcine serum albumin; for example, the albumin comprises an amino acid sequence shown in SEQ ID NO: 1; and
preferably, the albumin is selected from human serum albumin (HSA), and recombinant human albumin (rHA).

Embodiment 34. A method for preparing the composition of any one of Embodiments 1 to 33, characterized in that the method includes the following steps:
(1) dissolving the SN-38, the lipid, and the Span 20 in an organic solvent to form an organic phase; and preparing an aqueous solution of the albumin as an aqueous phase;
(2) mixing the organic phase and the aqueous phase to form an emulsion, wherein the emulsion comprises the nanoparticles, wherein in the nanoparticles, the albumin encapsulates at least part of the SN-38 and optionally at least part of the lipid; and
(3) removing the organic solvent in the emulsion to obtain a product comprising the nanoparticles.

Embodiment 35. The method of Embodiment 34, characterized in that the method includes the following steps:
(1) dissolving the SN-38, the lipid, and the Span 20 using a mixed organic solvent comprising a first organic solvent selected from DMSO and a $C_{1-3}$ alcohol (including methanol, ethanol, and isopropanol, and any combination thereof, preferably ethanol (EtOH)) and a second organic solvent selected from $CHCl_3$ and a mixture of $CH_2Cl_2$ and $CHCl_3$ to form an organic phase, wherein in the mixed organic solvent, a volume ratio of the second organic solvent to the DMSO or $C_{1-3}$ alcohol is about 1:20 (v/v) ro about 20:1 (v/v), such as about 1:5 to about 5:1 (v/v), about 1:2 to about 4:1 (v/v), about 1:1 to about 4:1 (v/v), about 1.5:1 (v/v) to about 3:1 (v/v), or about 2:1 (v/v) to 7:3 (v/v); and preparing an aqueous solution of the albumin as an aqueous phase;
(2) mixing the organic phase and the aqueous phase to prepare an emulsion, wherein the emulsion comprises the nanoparticles, wherein in the nanoparticles, the albumin encapsulates at least part of the SN-38 and optionally at least part of the lipid;
(3) removing the organic solvent; and
(4) optionally, sterilizing the product obtained in step (3), preferably by filtering through a filter membrane of about 0.2 µm;
wherein optionally, the second organic solvent is $CHCl_3$, or a mixture of $CH_2Cl_2$ and $CHCl_3$, wherein optionally, a volume ratio of $CH_2Cl_2$ to $CHCl_3$ in the mixture is about 2:5-1:1, preferably about 2:5.

Embodiment 36. The method of Embodiment 34 or 35, characterized in that in step (2), the organic phase:the aqueous phase is about 1:2 (v/v) to about 1:50 (v/v), such as about 1:5 (v/v) to about 1:20 (v/v), about 1:7 (v/v) to about 1:15 (v/v), about 1:10 (v/v) to about 1:12 (v/v), e.g., about 1:5 (v/v) to about 1:12 (v/v), about 1:5 (v/v) to about 1:12 (v/v), about 1:6 (v/v), about 1:7 (v/v), or about 1:10 (v/v).

Embodiment 37. The method of any one of Embodiments 34 to 36, characterized in that step (2) includes the following steps:
(2-1) dispersing the organic phase in the aqueous phase under shearing to obtain a crude emulsion; and
(2-2) homogenizing the crude emulsion under a high pressure to obtain a fine emulsion comprising the nanoparticles.

Embodiment 38. The method of any one of Embodiments 34 to 37, characterized in that:
the aqueous phase comprises no additional stabilizer; or
the aqueous phase has already comprised an additional stabilizer; or
the method further includes adding an additional stabilizer in step (2); and
wherein the additional stabilizer is in such an amount that the content of the additional stabilizer in the product obtained in step (3) or (4) is at least about 2 w/v %, such as at least about 3 w/v %, at least about 5 w/v %, about 5 w/v % to about 30 w/v %, about 10 w/v % to about 25 w/v %, or about 15 w/v % to about 20 w/v %.

Embodiment 39. The method of Embodiment 38, wherein the additional stabilizer is selected from albumins (such as human serum albumin, recombinant human albumin, bovine serum albumin, and skim milk powder), monosaccharides, disaccharides, polysaccharides, mannitol, and any combination thereof, preferably selected from mannitol, lactose, maltose, trehalose, dextran, glucose, and sucrose, and any composition thereof, preferably is sucrose.

Embodiment 40. The method of any one of Embodiments 34 to 39, characterized in that the mixed organic solvent in step (1) is added to the aqueous phase before mixing the organic phase and the aqueous phase in step (2).

Embodiment 41. The method of Embodiment 40, characterized in that the volume of the added mixed solvent is equal to or smaller than the volume of the organic phase; for example, a volume ratio of the added mixed organic solvent to the organic phase is about 1:1 (v/v) to about 1:5 (v/v), such as about 1:2 (v/v) to about 1:4 (v/v) or about 1:3 (v/v).

Embodiment 42. The method of any one of Embodiments 34 to 41, characterized in that:
in the organic phase in step (1),
the SN-38 has a concentration of about 5-17 mg/mL, such as about 5.25-12 mg/mL, about 7-12 mg/mL, or about 10 mg/mL; and/or
the lipid has a concentration of about 3-50 mg/mL, such as about 5-45 mg/mL or about 7.5-30 mg/mL, about 10-25 mg/mL or about 15-20 mg/mL; and/or
in the aqueous phase, the albumin has a concentration of about 5-15 mg/mL, such as about 6-12 mg/mL or about 6-10 mg/mL.

Embodiment 43. The method of any one of Embodiments 34 to 41, characterized in that:
in the organic phase in step (1),
the concentration of the SN-38 is about 4-10 mg/mL, such as about 6-8 mg/mL; and/or
the concentration of the lipid is about 10-20 mg/mL, such as about 15 mg/mL; and/or
the concentration of the Span 20 is about 0.3-6 mg/mL, such as about 0.3-2 mg/mL or about 0.6-1 mg/mL; and/or
in the aqueous phase, the concentration of the albumin is about 8-30 mg/mL, such as about 12-20 mg/mL or about 16-18 mg/mL.

Embodiment 44. The method of any one of Embodiments 34 to 43, including step (4): sterilizing the product obtained in step (3), preferably by filtering through a filter membrane of about 0.2 μm.

Embodiment 45. The method of any one of Embodiments 34 to 44, characterized in that the method further includes the following step:
(5) drying the product obtained in step (3) or (4), preferably by spray drying or lyophilizing, to provide a composition in a solid form, preferably a powder, and more preferably a lyophilized powder; and
preferably, the SN-38 exists in the composition in an amorphous form.

Embodiment 46. The method of Embodiment 45, characterized in that step (5) further includes: adding the additional stabilizer as recited in Embodiment 39 to the product obtained in step (3) or (4) before drying, wherein the additional stabilizer is in such an amount that when the solid form obtained in step (5) is reconstituted to form an aqueous composition (including a solution and an emulsion), the additional stabilizer has a content of at least about 2 w/v %, such as at least about 3 w/v %, at least about 5 w/v %, about 5 w/v % to about 30 w/v %, about 10 w/v % to about 25 w/v %, or about 15 w/v % to about 20 w/v %.

Embodiment 47. A pharmaceutical composition, comprising the composition of any one of Embodiments 1 to 33, and optionally a pharmaceutically acceptable carrier.

Embodiment 48. A pharmaceutical composition, comprising the composition of any one of Embodiments 1 to 33 which has been dried, and optionally a pharmaceutically acceptable carrier.

Embodiment 49. The pharmaceutical composition of Embodiment 48, wherein the drying is lyophilizing or spray drying, preferably lyophilizing.

Embodiment 50. The pharmaceutical composition of Embodiment 48 or 49, which is in a solid form, preferably a lyophilized powder, and preferably used for parenteral administration, more preferably administration by intravenous injection.

Embodiment 51. Use of the composition of any one of Embodiments 1 to 33 or the pharmaceutical composition of any one of Embodiments 47 to 50 in the manufacture of a medicament for treating an SN-38 sensitive tumor in a subject, wherein the tumor is preferably is selected from colorectal cancer, small cell lung cancer, lymph cancer, breast cancer (preferably triple-negative breast cancer), esophageal cancer, gastric cancer, liver cancer, renal cancer, pancreatic cancer, uterine cancer, and ovarian cancer.

Embodiment 52. The composition of any one of Embodiments 1 to 33 or the pharmaceutical composition of any one of Embodiments 47 to 50, for use in treating an SN-38 sensitive tumor in a subject, wherein the tumor is preferably selected from colorectal cancer, small cell lung cancer, lymph cancer, breast cancer (preferably triple-negative breast cancer), esophageal cancer, gastric cancer, liver cancer, renal cancer, pancreatic cancer, uterine cancer, and ovarian cancer.

Embodiment 53. A method for treating an SN-38 sensitive tumor in a subject, including administering a therapeutically effective amount of the composition of any one of Embodiments 1 to 33 or the pharmaceutical composition of any one of Embodiments 47 to 50 to the subject, wherein the tumor is preferably selected from colorectal cancer, small cell lung cancer, lymph cancer, breast cancer (preferably triple-negative breast cancer), esophageal cancer, gastric cancer, liver cancer, renal cancer, pancreatic cancer, uterine cancer, and ovarian cancer.

Embodiment 54. A kit, comprising the composition of any one of Embodiments 1 to 33 or the pharmaceutical composition of any one of Embodiments 47 to 50.

Embodiment 55. A method for preparing a composition with improved properties, wherein the composition comprises SN-38, a lipid, and an albumin, and the albumin encapsulates at least part of the SN-38 and optionally at least part of the lipid to form nanoparticles, and
wherein the method is characterized in that Span 20 is added in the course of preparing the composition;
wherein optionally, the composition comprises no additional stabilizer; and/or
wherein optionally, the improved properties include improved stability; wherein, for example, when the composition is in a liquid form, the improved stability includes: reduced formation or content of an albumin multimer (for example, the albumin multimer does not exist or substantially does not exist in the composition, or the albumin multimer accounts for at most 5 w/w %, such as at most about 4%, at most about 2%, at most about 1.5%, at most about 1.2%, at most about 1.1%, at most about 1%, or at most about 0.8%, of the total amount of the albumin), and/or reduced particle size of the nanoparticles during the preparation, storage and/or use of the composition; and/or
wherein optionally, the composition is as defined in any one of Embodiments 1 to 33.

Embodiment 56. The method of Embodiment 55, characterized in that the method includes the following steps:
(1) dissolving the SN-38, the lipid, and the Span 20 in an organic solvent to form an organic phase; and preparing an aqueous solution of the albumin as an aqueous phase;
(2) mixing the organic phase and the aqueous phase to form an emulsion, wherein the emulsion comprises the nanoparticles, wherein in the nanoparticles, the albumin encapsulates at least part of the SN-38 and optionally at least part of the lipid; and
(3) removing the organic solvent in the emulsion to obtain a product comprising the nanoparticles.

Embodiment 57. The method of Embodiment 56, characterized in that the method includes the following steps:

(1) dissolving the SN-38, the lipid, and the Span 20 using a mixed organic solvent comprising a first organic solvent selected from DMSO and a $C_{1-3}$ alcohol (including methanol, ethanol, and isopropanol, and any combination thereof, preferably ethanol (EtOH)) and a second organic solvent selected from $CHCl_3$ and a mixture of $CH_2Cl_2$ and $CHCl_3$ to form an organic phase, wherein in the mixed organic solvent, a volume ratio of the second organic solvent to the DMSO or $C_{1-3}$ alcohol is about 1:20 (v/v) ro about 20:1 (v/v), such as about 1:5 to about 5:1 (v/v), about 1:2 to about 4:1 (v/v), about 1:1 to about 4:1 (v/v), about 1.5:1 (v/v) to about 3:1 (v/v), or about 2:1 (v/v) to 7:3 (v/v); and preparing an aqueous solution of the albumin as an aqueous phase;

(2) mixing the organic phase and the aqueous phase to prepare an emulsion, wherein the emulsion comprises the nanoparticles, wherein in the nanoparticles, the albumin encapsulates at least part of the SN-38 and optionally at least part of the lipid;

(3) removing the organic solvent; and (4) optionally, sterilizing the product obtained in step (3), preferably by filtering through a filter membrane of about 0.2 μm;

wherein optionally, the second organic solvent is $CHCl_3$, or a mixture of $CH_2Cl_2$ and $CHCl_3$, wherein optionally, a volume ratio of $CH_2Cl_2$ to $CHCl_3$ in the mixture is about 2:5-1:1, preferably about 2:5.

Beneficial Effects

The inventors have found that the invention allows for reduced number of high pressure homogenization during preparation, effectively reduced particle size of the nanoparticles in the composition, increased filtration flux, stabilization of the particle size of the nanoparticles after disintegration, reduced raw material loss and reduced cost, especially in the scaled-up process, e.g., in pilot-scale preparation. In addition, by further controlling the content of the albumin in the composition, the invention allows for control of the particle size of the nanoparticles. Therefore, the particle size of the nanoparticles in the composition of the invention is closer to a size suitable for drug preparation. In addition, the composition of the invention has low immunogenicity, high safety and has excellent storage stability, since the formation of albumin multimers is prevented due to the existence of Span 20 during storage.

EXAMPLES

The invention will be further illustrated in the following Examples. These examples are merely used for describing the invention, but not intended to limit the invention in any way.

Abbreviations used in Examples have the following meanings.

| Abbreviation | Chinese Name | Abbreviation | Chinese Name |
| --- | --- | --- | --- |
| rHA | Recombinant human serum albumin | HSA | Human serum albumin |
| HPLC | High performance liquid chromatography | EtOH | Ethanol |
| SEC-HPLC | Size-exclusion chromatography | $CHCl_3$ | Chloroform |
| PDI | Polymer dispersity index | Chol | Cholesterol |
| Chol-PA | Cholesteryl palmitate | SA-Gly | Glyceryl monostearate |

Methods of Measuring Various Parameters of Products Prepared in Examples

1. Measurement of Particle Size and Particle Size Distribution

A Malvern Nano ZSE particle size potentiometer was used to measure particle size and particle size distribution of nanoparticles in samples. A laser beam emitted by the instrument had a wavelength of 633 nm, and an included angle between incident light and scattered light was 173°. Parameters were set as follows: protein as the sample material; water as the dispersant; the measurement temperature of 25° C.; and automatic scanning detection. Each sample was measured thrice in parallel and results were averaged.

2. Measurement of Zeta Potential

The Malvern Nano ZSE particle size potentiometer was used to measure Zeta potential of nanoparticles in samples. Parameters were set as follows: protein as the sample material; and water as the dispersant. DTS1070 sample pool was selected; the measurement temperature was 25° C.; and automatic scanning detection was adopted. Test samples were diluted 10 times by volume using deionized water before detection. Each sample was measured thrice in parallel and results were averaged.

3. Measurement of Content of SN-38 in System 10 mg of a prepared sample was taken, diluted 5 times with deionized water, then diluted 10 times times isopropanol, extracted ultrasonically for 15 min, and then centrifuged at 10000 rpm/min for 12 min. The supernatant was taken for determining SN-38 in the system by HPLC, and the peak area was fitted to a standard curve to calculate the content of SN-38 in the system.

The chromatographic conditions of HPLC were as shown in Table 1.

TABLE 1

Chromatographic Conditions for Measuring the Content of SN-38 by HPLC

| | |
| --- | --- |
| Chromatographic column model | Agilent Poroshell 120 EC-C18 2.7 μm 3.0 * 150 mm |
| Detector wavelength | 265 nm, 381 nm |
| Column temperature | 50° C. |
| Sample tray temperature | Room temperature |
| Mobile phases | A: 25 mM $NaH_2PO_4$, pH 3.1; B: acetonitrile (ACN) |
| Flow rate | 0.6 mL/min |
| Elution mode | Gradient elution |
| Sample injection volume | 5 μL |
| Running time | 25 min |

Conditions of gradient elution were as shown in Table 2.

TABLE 2

Conditions of Gradient Elution Used in Measuring the Content of SN-38 by HPLC

| Time (min) | A % | B % |
| --- | --- | --- |
| 0 | 80 | 20 |
| 5 | 80 | 20 |
| 15 | 15 | 85 |

TABLE 2-continued

Conditions of Gradient Elution Used in Measuring the Content of SN-38 by HPLC

| Time (min) | A % | B % |
|---|---|---|
| 20 | 15 | 85 |
| 22 | 80 | 20 |
| 25 | 80 | 20 |

The resulting typical chromatogram of the measurement of the content of SN-38 is as shown in FIG. 1 (taking Example 1 for example).

4. Measurement of Content of Albumin in System

The BCA method was used to measure the content of albumin in the system. BSA was used as a standard and the sample was diluted 10 times. 25 µL of the diluted sample was taken, added with 200 L of a detection solution, and mixed homogeneously by shaking on a shaker, and then the microwell plate was sealed and incubated at 37° C. for 120 min. Absorbance was measured at 562 nm on a microplate reader, and the concentration of albumin in the sample was calculated according to a standard curve.

5. Measurement of Content of Cholesterol in System

The content of the cholesterol in the sample was measured by HPLC. The method for diluting the sample was the same with the above measurement of the SN-38 content. Chromatographic conditions were as shown in Table 3.

TABLE 3

Chromatographic Conditions for Measuring Content of Cholesterol by HPLC

| Chromatographic column model | Agilent Eclipse XDB-C18 5 µm 4.6 * 250 mM |
|---|---|
| Chromatographic column No. | ZJ-RP-001 |
| Detector wavelength | 205 nm |
| Column temperature | 30° C. |
| Sample tray temperature | 15° C. |
| Flow rate | 1 mL/min |
| Mobile phase | Methanol |

TABLE 3-continued

Chromatographic Conditions for Measuring Content of Cholesterol by HPLC

| Elution mode | Isocratic elution |
|---|---|
| Sample injection volume | 5 µL |
| Running time | 20 min |

Figure 2:
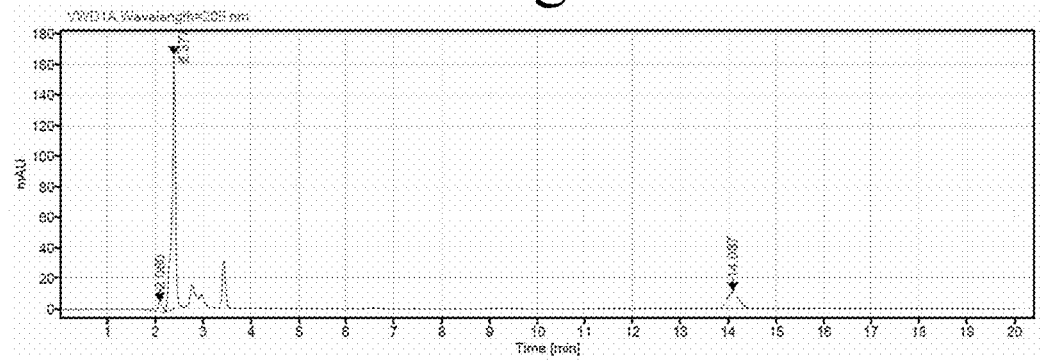
FIG. 2 is a typical HPLC chromatogram of a content measurement of cholesterol in the product prepared in Example 1.

The resulting typical chromatogram of the measurement of the content of cholesterol is as shown in FIG. 2 (taking Example 1 for example).

6. Calculation of Loading of Drug (LD) and Encapsulation Efficiency (EE)

$$LD\ (\%) = \frac{\text{Content of total } SN-38 \text{ in system} - \text{Content of free } SN-38 \text{ in system}}{\text{Content of albumin in system} + \text{Content of total } SN-38 \text{ in system} + \text{content of lipid in system}} \times 100\%$$

$$EE\ (\%) = \frac{\text{Content of total } SN-38 \text{ in system} - \text{Content of free } SN-38 \text{ in system}}{\text{Content of total } SN-38 \text{ in system}} \times 100\%$$

wherein the content of total SN-38 in system was measured by the method described in "3. Measurement of Content of SN-38 in System".

The content of free SN-38 in system was measured by HPLC after being extracted by solid-phase extraction. The specific method of the solid-phase extraction was as follows:

1) SPE plug (Select Core™ HLB, 1 mL) activation: activated firstly using 3 mL of methanol and then using 3 mL.

2) 200 µL of a sample to be separated was loaded and passed through the column under gravity.

3) Elution was performed with 2 mL of water under gravity.

4) Elution was performed with 2 mL of methanol under gravity. The methanol phase was collected to obtain the detection solution of free SN-38.

7. Detection of Two Structures of SN-38

The two structures of SN-38 different in activity are as schematically shown below:

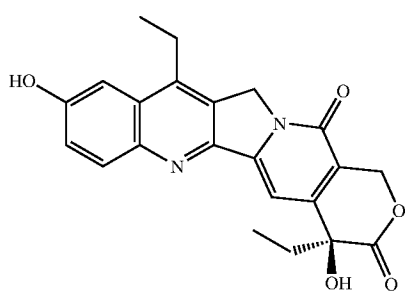
Close-ringed structure-lactone (active)

nuetral/base ⇌ acid

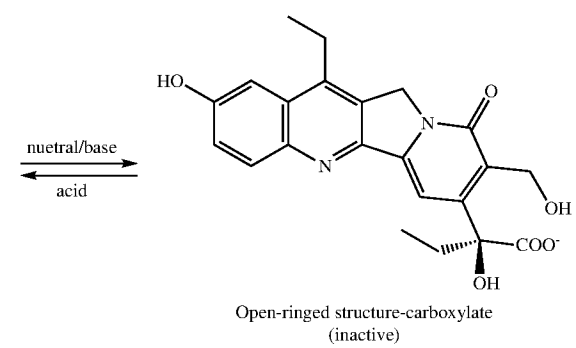
Open-ringed structure-carboxylate (inactive)

The method for treating the sample was the same with the above measurement of the SN-38 content and the chromatographic conditions of HPLC were as shown in Table 4.

TABLE 4

Chromatographic Conditions of HPLC for Measurement of the contents of Different Structures of SN-38

| | |
|---|---|
| Chromatographic column model | Agilent Poroshell 120 EC-C18 4 μm 3.0 * 150 mM |
| Chromatographic column No. | QCCA-RP-007 |
| Detector wavelength | 265 nm, Ref 460 nm, 40 nm |
| Column temperature | 40° C. |
| Sample tray temperature | Room temperature |
| Flow rate | 1 mL/min |
| Mobile phases | A: 25 mM $KH_2PO_4$; B: ACN |
| Elution mode | Gradient elution |
| Sample injection volume | 5 μL |
| Running time | 20 min |

Conditions of gradient elution were as shown in Table 5.

TABLE 5

Conditions of Gradient Elution Used in Measuring Contents of Different Structures of SN-38 by HPLC

| Time (min) | A % | B % |
|---|---|---|
| 0 | 95 | 5 |
| 15 | 40 | 60 |
| 18 | 40 | 60 |
| 18.1 | 95 | 5 |
| 20 | 95 | 5 |

Figure 3:
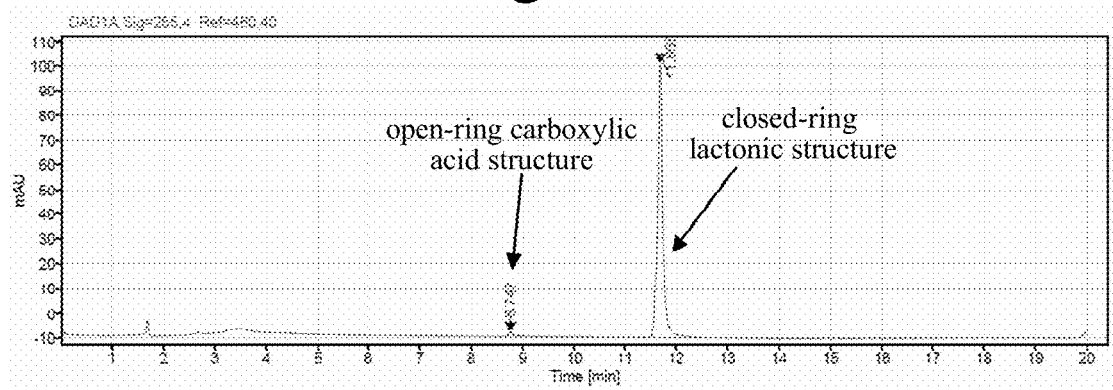
FIG. 3 is a typical HPLC chromatogram of a content measurement of SN-38 of different structures in the product prepared in Example 1.

The resulting typical chromatogram measured for the contents of different structures of SN-38 is as shown in FIG. 3 (taking Example 1 for example).

A proportion of the open-ring SN-38 in the sample can be calculated according to the peak area ratio of the open-ring structure to the lactonic ring structure in the chromatogram. The proportions of the open-ring SN-38 in the samples prepared in the Examples according to the invention were all <2.0%.

8. Measurement of Albumin Aggregates in Sample

SEC-HPLC was used to measure the aggregation of albumin in the sample. 5 l of the prepared sample was directly taken for detection, and chromatographic conditions were as shown in Table 6.

TABLE 6

Chromatographic Conditions of SEC-HPLC for Measuring Albumin Aggregates in Sample

| | |
|---|---|
| Chromatographic column model | TSKgel G4000SWxl 7.8 × 300 mm, 8 μm |
| Chromatographic column No. | QCCA-RP-007 |
| Detector wavelength | 280 nm, 260 nm |
| Column temperature | 30° C. |
| Sample tray temperature | 10° C. |
| Flow rate | 0.5 mL/min |
| Mobile phase | 0.05M Tris-HCl, pH 7.0 |
| Elution mode | Isocratic elution |
| Sample injection volume | 5 μL |
| Running time | 30 min |

Figure 4:
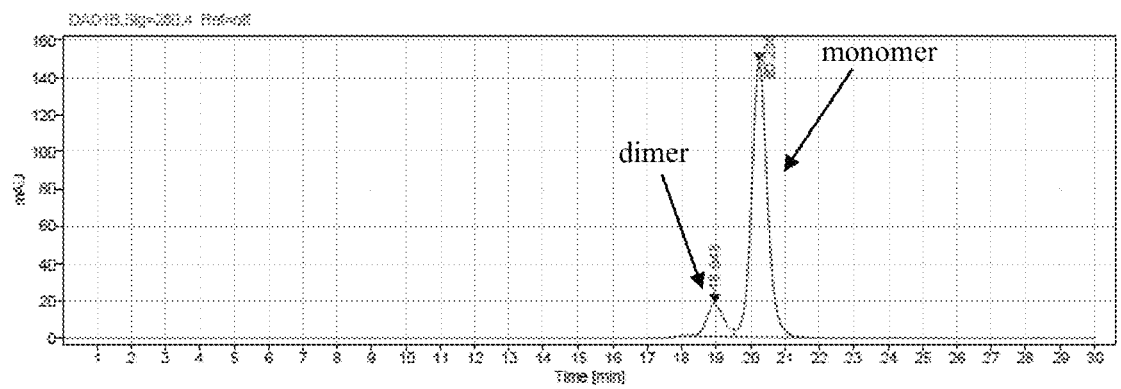
FIG. 4 is a typical SEC-HPLC chromatogram of a measurement of albumin aggregates in the product prepared in Example 1.

The resulting typical chromatogram of the measurement of albumin aggregates is as shown in FIG. 4 (taking Example 1 for example). The results showed that there was no albumin multimer in the samples and only little dimer existed, indicating that this product did not produce immunogenicity due to albumin multimers.

9. Experiments on Stability and Disintegration

The stability of samples was measured mainly by storing the prepared samples at room temperature and 4° C. separately and observing whether there was obvious precipitation or precipitate in the samples at intervals; meanwhile, samples were taken for detection of the particle size and the particle size distribution to study particle size change of the nanoparticles in the samples.

The disintegration experiment was conducted to study the binding stability of the albumin and the SN-38 in the sample. The sample was diluted with 1×PBS at pH of 7.4, and the particle size and the particle size distribution of the samples at different dilution factors were measured to study at what dilution factor disintegration of the nanoparticles will occur to precipitate out the SN-38 raw material. A higher dilution factor indicates better stability of the nanoparticles.

10. XRD Detection Method

The X-ray diffraction method (Bruker, D8 ADVANCE) was used to evaluate the crystal form change of the active pharmaceutical ingredient (API) in the sample. The crystal forms of lyophilized albumin powder, lyophilized albumin-SN-38 powder, and SN-38 were detected separately. Cu-Kα rays were used to scan a 2θ range of 2°-40° at a speed of 2°/min.

11. Electron Microscopy Detection Method

Sample preparation conditions: the API concentration of each sample was adjusted to 2 mg/mL with water for injection. The temperature was 4° C., the humidity was 100%, the blot time was 9 seconds, and the blot force was 3. A cryogenic transmission electron microscope (Talos 120C) was used to observe the morphology of vesicles and crystals in the sample under 120 Kv.

According to specific circumstances, the above measurement methods were selected to measure the samples prepared in the following Examples.

Experimental Materials

Unless otherwise stated, the SN-38 used in the following Examples was provided by Sichuanxieli Pharmaceutical Co., Ltd.; the cholesterol was provided by Jiangsu Southeast Nanomaterials Co., Ltd.; rHA was provided by North China Pharmaceutical Company Ltd.; HSA was provided by Guang Dong Shuang Lin Bio-Pharmacy Co., Ltd.; and the irinotecan hydrochloride injection (CPT-11, 60 mg/kg) was provided by Jiangsu Hengrui Pharmaceuticals Co., Ltd.

Unless otherwise stated, in the following animal experimental studies, the doses of the rHA-SN-38 or HSA-SN-38 products and CPT-11 were based on active ingredients; the solvent was water for injection and used as blank control.

Example 1: Preparation of rHA-SN-38 Product 1

1. Preparation Process
  1) An organic solvent of EtOH/CHCl$_3$ in a volume ratio of 2/3 was prepared;
  2) 21 mg of SN-38 and 30 mg of cholesterol were taken, added with 3 mL of the organic solvent in step 1), and dissolved completely to obtain a drug solution;
  3) An aqueous solution of rHA with a total volume of about 21 mL was prepared with deionized water as an aqueous phase such that the total content of rHA in the aqueous phase was 200 mg;
  4) Shearing dispersion: after the drug solution in step 2) was mixed with the aqueous phase in step 3), shearing dispersion was performed for 10-15 min to obtain a crude emulsion;

5) The crude emulsion was transferred to a high pressure homogenizer and homogenized under a pressure of 1300-1500 bar for 2-7 min;
6) Rotary evaporation was performed at 40° C.-45° C. for 4-8 min;
7) Filtration was performed through a 0.2 μm PES syringe filter membrane (Sartorius Pham.).

Before and after the filtration, the parameters such as particle size, encapsulation efficiency, and loading of drug of the product sample were measured.

2. Measurement Results

The measurement results of the sample prepared in Example 1 are shown in Table 7.

8) A lyophilized formulation of HSA-SN-38 nanoparticles was obtained by filtering through a 0.2 μm PES syringe filter membrane, filling in vials, and lyophilizing in vacuum.

The lyophilized product was subjected to XRD analysis.

Two lyophilized samples were taken, of which one was diluted with deionized water such that the concentration of SN-38 was the same as the concentration before lyophilization (reconstituted solution 1) while the other was diluted with deionized water such that the concentration of SN-38 was 6 times the concentration before lyophilization (recon-

TABLE 7

Measurement Results of Parameters of Sample Prepared in Example 1

| Parameters | Sample Before Passing Through Membrane | Sample After Passing Through Membrane |
| --- | --- | --- |
| Particle size (nm) | 171.2 ± 8.04 nm | 124.6 ± 3.62 nm |
| PDI | 0.243 ± 0.015 | 0.217 ± 0.015 |
| Zeta potential (mV) | −33.5 | −31.3 |
| Loading of drug (%) | — | 3.27 |
| Encapsulation efficiency (%) | — | 90.10 |
| Proportion (%) of open-ring SN-38 | 1.987 | 1.833 |
| Concentration at disintegration | — | When the original sample was diluted 1000 times, the particle size distribution became wide, but no disintegration occurred to precipitate SN-38 particles. After dilution 10000 times, obvious disintegration occurred. That is, when the concentration of SN-38 in the sample was diluted to <0.05 μg/mL, the nanoparticles disintegrated rapidly. |
| Stability | — | After the sample was stored in a refrigerator at 4° C. for 24 h, the particle size of the sample was 138.2 ± 5.36 nm, and the particle size was increased by a proportion of 10.91%. |

Notes:
Proportion of particle size increase = ((particle size after placement − particle size before placement) * 100%/particle size before placement)

Example 2: Preparation of Lyophilized Formulation of HSA-SN-38 Product 1 and Reconstituted Solution Thereof 1. Preparation Process
1) An organic solvent of EtOH/CHCl$_3$ in a volume ratio of 2/3 was prepared;
2) 21 mg of SN-38 and 30 mg of cholesterol were taken, added with 3 mL of the organic solvent in step 1), and dissolved completely to obtain a drug solution;
3) An aqueous solution of HSA with a total volume of about 32 mL was prepared with deionized water as an aqueous phase such that the total content of HSA in the aqueous phase was 200 mg;
4) Shearing dispersion: after the drug solution in step 2) was mixed with the aqueous phase in step 3), shearing dispersion was performed for 10-15 min to obtain a crude emulsion;
5) The crude emulsion was transferred to a high pressure homogenizer and homogenized under a pressure of 1300-1500 bar for 2-7 min;
6) Rotary evaporation was performed at 40° C.-45° C. for 4-8 min;
7) Sucrose was added to the product obtained in step 6) and stirred such that the sucrose was dissolved completely to obtain a sucrose concentration of 30 mg/mL;

stituted solution 2). The parameters such as particle size and encapsulation efficiency of the two reconstituted solutions were measured.

2. Measurement Results (1) Measurement Results of Parameters of Reconstituted Solutions The measurement results of the parameters of the reconstituted solutions of the lyophilized products prepared in Example 2 are shown in Table 8.

TABLE 8

Measurement Results of Parameters of Reconstituted Solutions of Lyophilized Products Prepared in Example 2

| Parameters | Reconstituted Solution 1 | Reconstituted Solution 2 |
| --- | --- | --- |
| pH | 6.91 | 6.90 |
| Particle size (d, nm) | 158.3 ± 3.4 | 178.2 ± 3.2 |
| PDI | 0.210 ± 0.018 | 0.241 ± 0.018 |
| Zeta potential (mV) | −31.4 ± 0.6 | −29.3 ± 0.9 |
| Open-ring proportion (%) | 1.86 | 1.92 |
| Encapsulation efficiency (%) | 98.64 | 98.97 |

TABLE 8-continued

Measurement Results of Parameters of Reconstituted Solutions of Lyophilized Products Prepared in Example 2

| Parameters | Reconstituted Solution 1 | Reconstituted Solution 2 |
|---|---|---|
| Loading of drug (%) | 5.08 | 5.08 |

Notes:
in the encapsulation efficiency measurement here, the method for measuring the content of free SN-38 was as follows: the sample was centrifuged at a high speed (centrifuged at 21000 rpm for 1 h), and the supernatant was taken and then extracted by adding 9 times the volume of acetonitrile for for detection.

The results show that when the concentration of the active ingredient was increased by up to 6 times after reconstitution, the particle size was just increased slightly and remained less than 200 nm. Other properties of the sample were not affected greatly. Therefore, the lyophilized formulation of the present application can be diluted to various concentrations as needed for use.

Figure 5:
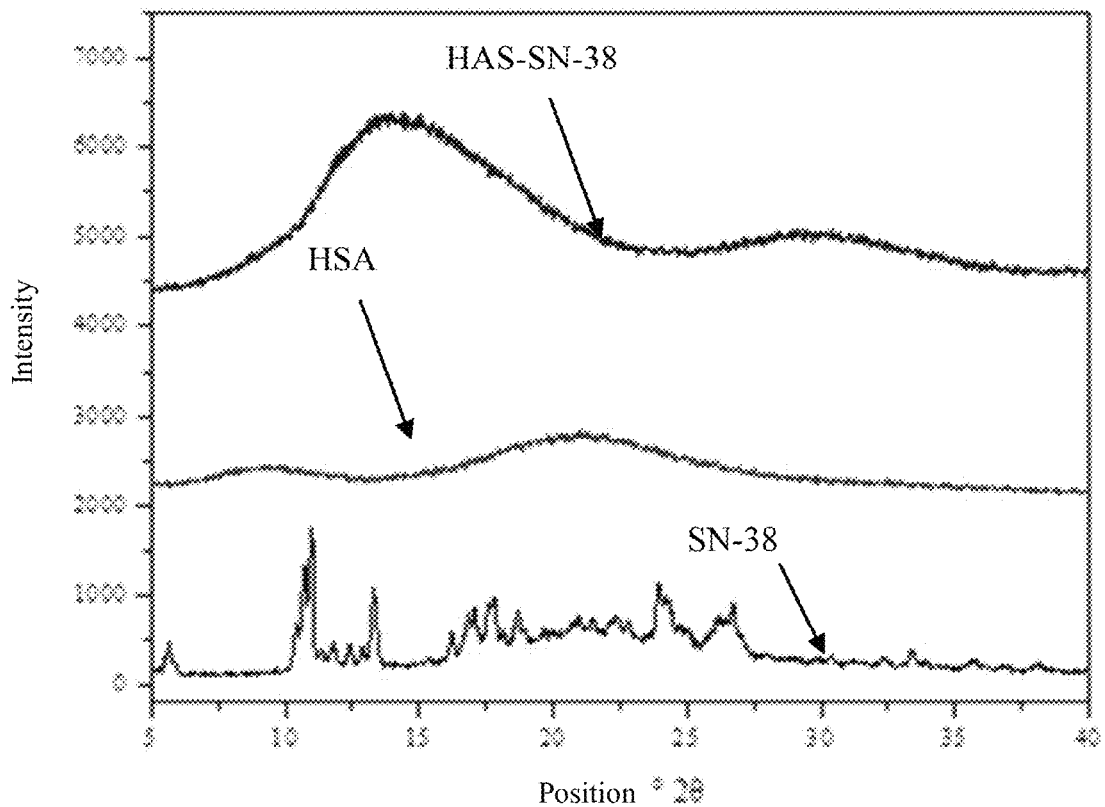
FIG. 5 is an XRD spectrum of the lyophilized product prepared in Example 2, SN-38, and HSA.

(2) XRD Analysis Results The lyophilized product, the SN-38 crystal, and HSA were subjected to XRD detection, and the results are shown in FIG. 5.

The results show that by comparing the measurement results of HSA-SN-38 and SN-38, the SN-38 in the lyophilized powder was in an amorphous state. It has been reported that an active pharmaceutical ingredient in amorphous form is more prone to dissolving and higher in bioavailability, as compared to a crystalline form (e.g., Wang, D., Liang, N., Kawashima, Y. et al. Biotin-modified bovine serum albumin nanoparticles as a potential drug delivery system for paclitaxel. *J Mater Sci* 54, 8613-8626 (2019)). The formulation of the present application has the advantages of high SN-38 dissolution rate and high bioavailability, as compared to a crystalline form of SN-38.

Example 3: Preparation of rHA-SN-38 Product 2

1. Preparation Process
    1) An organic solvent of EtOH/CHCl$_3$ in a volume ratio of 2/3 was prepared;
    2) 42 mg of SN-38 and 60 mg of cholesterol were taken, added with 3 mL of the organic solvent in step 1), and dissolved completely to obtain a drug solution;
    3) An aqueous solution of rHA with a total volume of about 21 mL was prepared with deionized water as an aqueous phase such that the total content of rHA in the aqueous phase was 500 mg;
    4) Shearing dispersion: after the drug solution in step 2) was mixed with the aqueous phase in step 3), shearing dispersion was performed for 10-15 min to obtain a crude emulsion; 5) The crude emulsion was transferred to a high pressure homogenizer and homogenized under a pressure of 1300-1500 bar for 2-7 min;
    6) Rotary evaporation was performed at 40° C.-45° C. for 4-8 min;
    7) Filtration was performed through a 0.2 µm PES syringe filter membrane. Before and after the filtration, the parameters such as particle size, encapsulation efficiency, and loading of drug of the product sample were measured.

2. Measurement Results
The measurement results of Product 2 are shown in Table 9.

TABLE 9

Measurement Results of Parameters of Sample Prepared in Example 3

| Parameters | Sample Before Passing Through Membrane | Sample After Passing Through Membrane |
|---|---|---|
| Particle size/PDI (nm/—) | 177.6 nm/0.24 | 124.4 nm/0.214 |
| Zeta potential | −26.2 | −25.2 |
| Loading of drug (%) | 4.61 | 3.21 |
| Encapsulation efficiency (%) | 92.21 | 91.01 |

Example 4: Preparation of rHA-SN-38 Product 3

1. Preparation Process
    1) An organic solvent of EtOH/CHCl$_3$ in a volume ratio of 2/3 was prepared;
    2) 42 mg of SN-38 and 60 mg of cholesterol were taken, added with 3 mL of the organic solvent in step 1), and dissolved completely to obtain a drug solution;
    3) An aqueous solution of rHA with a total volume of about 21 mL was prepared with deionized water as an aqueous phase such that the total content of rHA in the aqueous phase was 200 mg;
    4) Shearing dispersion: after the drug solution in step 2) was mixed with the aqueous phase in step 3), shearing dispersion was performed for 10-15 min to obtain a crude emulsion;
    5) The crude emulsion was transferred to a high pressure homogenizer and homogenized under a pressure of 1300-1500 bar for 2-7 min;
    6) Rotary evaporation was performed at 40° C.-45° C. for 4-8 min;
    7) Filtration was performed through a 0.2 µm PES syringe filter membrane. Before and after the filtration, the parameters such as particle size, encapsulation efficiency, and loading of drug of the product sample were measured.

2. Measurement Results
The measurement results of Product 3 are shown in Table 10.

TABLE 10

Measurement Results of Parameters of Sample Prepared in Example 4

| Parameter | Sample Before Passing Through Membrane | Sample After Passing Through Membrane |
|---|---|---|
| Particle size/PDI (nm/—) | 150.7 nm/0.264 | 117.1 nm/0.204 |
| Loading of drug (%) | 10.6 | 9.3 |
| Encapsulation efficiency (%) | 80.3 | 79.10 |

Example 5: Preparation of rHA-SN-38 Product 4

1. Preparation Process
    1) An organic solvent of EtOH/CHCl$_3$ in a volume ratio of 2/3 was prepared;

2) 10 mg of SN-38 and 60 mg of cholesterol were taken, added with 3 mL of the organic solvent in step 1), and dissolved completely to obtain a drug solution;
3) An aqueous solution of rHA with a total volume of about 21 mL was prepared with deionized water as an aqueous phase such that the total content of rHA in the aqueous phase was 150 mg;
4) Shearing dispersion: after the drug solution in step 2) was mixed with the aqueous phase in step 3), shearing dispersion was performed for 10-15 min to obtain a crude emulsion;
5) The crude emulsion was transferred to a high pressure homogenizer and homogenized under a pressure of 1300-1500 bar for 2-7 min;
6) Rotary evaporation was performed at 40° C.-45° C. for 4-8 min;
7) Filtration was performed through a 0.2 μm PES syringe filter membrane. Before and after the filtration, the parameters such as the particle size, encapsulation efficiency, and the loading of drug of the product sample were measured.

2. Measurement Results

The measurement results of Product 4 are shown in Table 11.

TABLE 11

Measurement Results of Parameters of Sample Prepared in Example 5

| Parameter | Sample Before Passing Through Membrane | Sample After Passing Through Membrane |
|---|---|---|
| Particle size/PDI (nm/—) | 180.7 nm/0.226 | 146.3 nm/0.207 |
| Zeta potential | −26.1 | −35.6 |
| Loading of drug (%) | 4.1 | 3.13 |
| Encapsulation efficiency (%) | 92.1 | 90.4 |

Example 6: Preparation of rHA-SN-38 Product in the Absence of Lipid

The rHA-SN-38 product of Example 6 was prepared according to the preparation process of Example 1, except adding no lipid (e.g., the cholesterol) in step 2) of the preparation process of Example 1, and tested. The measurement results of the parameters of the rHA-SN-38 product are shown in Table 12.

TABLE 12

Measurement Results of Parameters of rHA-SN-38 Product Prepared in Example 6

| Parameters | Sample Before Passing Through Membrane | Sample After Passing Through Membrane |
|---|---|---|
| Particle size/PDI (nm/—) | 248.5 nm/0.205 | 160.3 nm/0.157 |
| Particle size after 24 h/PDI (nm/—) | — | 271.1 nm/0.228 |
| Loading of drug (%) | — | 2.15 |
| Encapsulation efficiency (%) | — | 82.70 |

The results show that the sample prepared without adding lipid was poor in stability, and the particle size of the sample was increased by 69.120 after storage in refrigerator at 4° C. for 24 h. In contrast, after the sample prepared in Example 1 (added with lipid) was stored in refrigerator at 4° C. for 24 h, the particle size of the sample was increased only by 10.91%. This shows that the addition of the cholesterol greatly improved the stability of the sample. In addition, the loading of drug and the encapsulation efficiency without adding lipid were lower than the results with addition of the cholesterol.

Example 7: Preparation of rHA-SN-38 Products with Addition of Other Lipids

Two rHA-SN-38 products were prepared according to the preparation process of Example 1 except replacing cholesterol in step 2) of the preparation process of Example 1 with cholic acid or palmic acid, and tested. The measurement results of the parameters of the rHA-SN-38 products are shown in Table 13.

TABLE 13

Measurement Results of Parameters of rHA-SN-38 Products Prepared in Example 7

| Sample | | Particle Size (nm) | PDI |
|---|---|---|---|
| 5 mg/mL of cholic acid added to the organic solvent | Sample Before Passing Through Membrane | 295.7 nm | 0.191 |
| | Sample After Passing Through Membrane | — | — |
| 5 mg/mL of palmic acid added to the organic solvent | Sample Before Passing Through Membrane | 533.4 nm | 0.222 |
| | Sample After Passing Through Membrane | — | — |

The results show that the samples prepared by the same preparation process with the cholic acid or the palmic acid as the lipid had a larger particle size, and the sample added with the palmic acid had even larger particle size and wider particle size distribution than the sample added with the cholic acid. After treatment through the membrane, the contents of the nanoparticles in the samples were extremely low and the particle size distribution was very large, and no objective results of the particle size and the PDI could be given.

Example 8: Study on Different Organic Solvent Systems

Except replacing the organic solvent in step 1) of the preparation process of Example 1 with the organic solvent system shown in Table 14, the rH4A-SN-38 products were prepared according to the preparation process of Example 1 and tested. The particle size of the obtained products were also measured after storage in refrigerator at 4° C. overnight. The measurement results of the parameters of the obtained rHA-SN-38 products are shown in Table 14.

TABLE 14

Measurement Results of Parameters of rHA-SN-38 Products Prepared Using Different Organic Solvent Systems

| Organic Solvent System (v/v) | Particle Size Before Passing Through Membrane/PDI (nm/—) | Particle Size After Passing Through Membrane/PDI (nm/—) | Particle Size After Storage at 4° C. Overnight/PDI (nm/—) | Loading of drug (%) | Absolute SN-38 Recovery (%) |
|---|---|---|---|---|---|
| Chloroform:ethanol = 1:1 | 178.2/0.251 | 118.2/0.177 | 137.1/0.197 | 4.21 | 34.39 |
| Chloroform:isopropanol = 1:1 | 230.1/0.253 | 132.8/0.186 | 153.8/0.171 | 2.66 | 22.92 |
| Chloroform:methanol = 1:1 | 209.2/0.311 | 128.5/0.245 | 150.1/0.180 | 2.80 | 26.93 |
| Dichloromethane:ethanol = 1:1 | 247.1/0.206 | 148.3/0.198 | 168.4/0.125 | 1.63 | 14.63 |
| Dichloromethane:methanol = 1:1 | 287.0/0.191 | 151.6/0.189 | 171.2/0.183 | 1.02 | 7.68 |
| Dichloromethane:isopropanol = 1:1 | 283.2/0.164 | 148.7/0.266 | 161.9/0.249 | 0.28 | 1.87 |

Notes:
the recovery of SN-38 was calculated according to the following formula: Absolute SN-38 recovery (%) = (SN-38 concentration in sample after passing through membrane measured by HPLC × Sample volume after passing through membrane)/(Amount of SN-38 feeded) × 100%

The results show that the sample prepared with the chloroform/ethanol system as the organic solvent had the smallest particle size and the highest loading of drug.

Example 9: Investigation on Different Ratios of Organic Solvents

Except that the organic solvent in step 1) of the preparation process of Example 1 was replaced with EtOH/CHCl$_3$ in different ratios shown in Table 15 and the amount of rHA used in the system was adjusted to 300 mg, rHA-SN-38 products were prepared according to the preparation process of Example 1 and tested. The measurement results of the parameters of the obtained rHA-SN-38 products are shown in Table 15.

TABLE 15

Measurement Results of Parameters of rHA-SN-38 Products Prepared Using EtOH/CHCl$_3$ in Different Ratios

| | Sample | Particle Size (nm) | PDI | Loading of drug (%) | Encapsulation efficiency (%) |
|---|---|---|---|---|---|
| EtOH/CHCl$_3$ = 1/1 (v/v) | Sample before passing through membrane | 154.7 | 0.220 | — | — |
| | Sample after passing through membrane | 125.0 | 0.197 | 3.89 | 92.74 |
| EtOH/CHCl$_3$ = 2/8 (v/v) | Sample before passing through membrane | 175.2 | 0.248 | — | — |
| | Sample after passing through membrane | 119.2 | 0.214 | 3.82 | 89.43 |
| EtOH/CHCl$_3$ = 1/9 (v/v) | Sample before passing through membrane | 318.3 | 0.348 | — | — |
| | Sample after passing through membrane | 120.7 | 0.235 | 1.34 | 84.02 |

It can be seen that the rHA-SN-38 products with satisfactory particle size, loading of drug and encapsulation efficiency can be obtained with the organic solutions of EtOH/CHCl$_3$ in different ratios.

Example 10: Investigation on Different Cholesterol Concentrations

Except that the amount of the cholesterol used in step 2) of the preparation process of Example 1 was adjusted to the amounts shown in Table 16, rHA-SN-38 products were prepared according to the preparation process of Example 1 and tested. The measurement results of the parameters of the obtained rHA-SN-38 products are shown in Table 16.

TABLE 16

Measurement Results of Parameters of rHA-SN-38 Products Prepared Using Different Concentrations of Cholesterol

|  | Sample | Particle Size (nm) | PDI | Loading of drug (%) | Encapsulation efficiency (%) |
| --- | --- | --- | --- | --- | --- |
| Cholesterol 9 mg | Sample before passing through membrane | 220.0 | 0.233 | — | — |
|  | Sample after passing through membrane | 145.1 | 0.189 | 1.94 | 92.74 |
| Cholesterol 15 mg | Sample before passing through membrane | 170.8 | 0.214 | — | — |
|  | Sample after passing through membrane | 132.7 | 0.179 | 3.79 | 90.47 |
| Cholesterol 45 mg | Sample before passing through membrane | 173.6 | 0.371 | — | — |
|  | Sample after passing through membrane | 126.8 | 0.247 | 3.60 | 94.07 |

The results show that when the amount of the cholesterol used in the formulation was increased, the particle size of the samples after passing through the membrane was smaller, and the encapsulation efficiency and the loading of drug of SN-38 in the samples were higher.

Example 11: Investigation on Different Concentrations of SN-38

Except that the amount of SN-38 used in step 2) of the preparation process of Example 1 was adjusted to the amounts shown in Table 17, rHA-SN-38 products were prepared according to the preparation process of Example 1 and tested. The measurement results of the parameters of the obtained rHA-SN-38 products are shown in Table 17.

TABLE 17

Measurement Results of Parameters of rHA-SN-38 Products Prepared Using Different Concentrations of SN-38

|  | Sample | Particle size (nm) | PDI | Loading of drug (%) | Encapsulation efficiency (%) |
| --- | --- | --- | --- | --- | --- |
| SN-38 15 mg | Sample Before Passing Through Membrane | 175.1 | 0.265 | — | — |
|  | Sample After Passing Through Membrane | 122.3 | 0.246 | 2.57 | 91.29 |
| SN-38 30 mg | Sample Before Passing Through Membrane | 180.3 | 0.226 | — | — |
|  | Sample After Passing Through Membrane | 126.7 | 0.195 | 4.60 | 88.94 |

The results show that the increase in SN-38 concentration in the formulation had little influence on the particle size but led to increased loading of drug.

Example 12: Investigation on Different rHA Concentrations in Aqueous Phase

Except that the amount of rHA or the volume of the aqueous phase in step 3) of the preparation process of Example 1 was adjusted to the values shown in Table 18, rHA-SN-38 products were prepared according to the preparation process of Example 1 and tested. The measurement results of the parameters of the obtained rH4A-SN-38 products are shown in Table 18.

TABLE 18

Measurement Results of Parameters of rHA-SN-38 Products Prepared Using Different Concentrations of rHA

| | Sample | Particle Size (nm) | PDI | Loading of drug (%) | Encapsulation efficiency (%) |
|---|---|---|---|---|---|
| rHA 150 mg | Sample before passing through membrane | 170.6 | 0.231 | — | — |
| | Sample after passing through membrane | 125.8 | 0.198 | 3.98 | 92.30 |
| rHA 250 mg | Sample before passing through membrane | 177.6 | 0.240 | — | — |
| | Sample after passing through membrane | 124.4 | 0.214 | 2.81 | 91.01 |

The results show that the increase in the amount of the albumin resulted in a slight reduction in loading of drug and had little influence on the encapsulation efficiency.

Example 13: Investigation on Different Volume Ratios of Organic Solvent/Aqueous Phase Except that the volume of the organic solvent in step 2) or the volume of the aqueous phase in step 3) of the preparation process of Example 1 was adjusted to the values shown in Table 19, rHA-SN-38 products were prepared according to the preparation process of Example 1 and tested. The measurement results of the parameters of the obtained rHA-SN-38 products are shown in Table 19.

TABLE 19

Measurement Results of Parameters of rHA-SN-38 Products Prepared with Different Volume Ratios of Organic Solvent/Aqueous Phase

| | Sample | Particle Size (nm) | PDI | Loading of drug (%) | Encapsulation efficiency (%) |
|---|---|---|---|---|---|
| Organic solvent volume 2 mL | Sample before passing through membrane | 176.5 | 0.248 | — | — |
| | Sample after passing through membrane | 120.7 | 0.235 | 3.56 | 89.23 |
| Organic solvent volume 4 mL | Sample before passing through membrane | 190.5 | 0.223 | — | — |
| | Sample after passing through membrane | 121.6 | 0.222 | 2.66 | 90.67 |
| Aqueous phase volume 17 mL | Sample before passing through membrane | 175.2 | 0.251 | — | — |
| | Sample after passing through membrane | 122.1 | 0.209 | 1.81 | 79.32 |
| Aqueous phase volume 27 mL | Sample before passing through membrane | 164.9 | 0.236 | — | — |
| | Sample after passing through membrane | 129.6 | 0.206 | 3.46 | 94.22 |

The results show that the smaller the volume ratio of organic solvent:aqueous phase, the higher the loading of drug of the product, and the encapsulation efficiency of SN-38 was increased.

Example 14: Preparation of rHA-SN-38 Products Comprising Additional Stabilizers 1. Preparation Process
   1) An organic solvent of EtOH/CHCl$_3$ in a volume ratio of 2/3 was prepared;
   2) 21 mg of SN-38 and 30 mg of cholesterol were taken, added with 3 mL of the organic solvent in step 1), and dissolved completely to obtain a drug solution;
   3) An HSA solution was prepared with deionized water and added with sucrose or glucose as the stabilizer to form an aqueous phase (about 32 mL), wherein the total content of HSA in the aqueous phase was 200 mg, and the concentration of the sucrose or the glucose in the final product was shown in Table 20;
   4) Shearing dispersion: after the drug solution in step 2) was mixed with the aqueous phase in step 3), shearing dispersion was performed for 10-15 min to obtain a crude emulsion;
   5) The crude emulsion was transferred to a high pressure homogenizer and homogenized under a pressure of 1300-1500 bar for 2-7 min;
   6) Rotary evaporation was performed at 40° C.-45° C. for 4-8 min;
   7) Filtration was performed through a 0.2 μm PES syringe filter membrane. Before and after the filtration, the parameters such as particle size, encapsulation efficiency, and loading of drug of the product samples were measured.
   8) The particle size of the obtained products was measured again after storage in refrigerator at 4° C. overnight.

2. Measurement Results

The measurement results of the parameters of the prepared HSA-SN-38 products are shown in Table 20.

TABLE 20

Measurement Results of Parameters of HSA-SN-38 Products Comprising Additional Stabilizers

| Saccharide Content (w/v) | Particle Size Before Passing Through Membrane/PDI (nm/—) | Particle Size After Passing Through Membrane/PDI (nm/—) | Particle Size After Storage at 4° C. Overnight/PDI (nm/—) | Loading of drug (%) | Absolute SN-38 Recovery (%) |
|---|---|---|---|---|---|
| 3% Sucrose | 176.6/0.265 | 117.0/0.263 | 124.2/0.251 | 3.86 | 34.25 |
| 10% Sucrose | 149.1/0.267 | 100.3/0.221 | 112.5/0.225 | 5.01 | 43.99 |
| 3% Glucose | 185.9/0.248 | 132.1/0.235 | 159.7/0.230 | 6.46 | 58.57 |
| 10% Glucose | 152.6/0.250 | 118.5/0.225 | 139.7/0.224 | 5.76* | 64.50 |

Notes:
*since the glucose is a reductive saccharide and will affect the result of the BAC detection of protein concentration, the measurement result of the loading of drug of the product added with glucose may be lower.

The results show that the product prepared by adding sucrose to the aqueous phase had a relatively smaller particle size and better stability as compared with the glucose, but had a lower loading of drug than the product prepared by adding glucose. For the same stabilizer, with the increase of its concentration, the parameters were further improved.

The inventors further measured the effect of cyclodextrin (5%, 10%, and 15%) as the stabilizer and found that after being placed at room temperature for 24 h, the prepared products were turbid due to precipitation or had a particle size of greater than 250 nm. Hence, cyclodextrin may not be suitable for use as the stabilizer.

Example 15: Preparation of HSA-SN-38 Products by Different Preparation Process 1. Preparation Process
   1) An organic solvent of EtOH/CHCl$_3$ in a volume ratio of 2/3 was prepared;
   2) 21 mg of SN-38 and 30 mg of cholesterol were taken, added with 3 mL of the organic solvent in step 1), and dissolved completely to obtain a drug solution;
   3) An HSA solution was prepared with deionized water and added with sucrose as an aqueous phase (about 32 mL), wherein the total content of HSA in the aqueous phase was 200 mg, and the concentration of the sucrose in the final product was 10% (w/v);
   4) Shearing dispersion: 1 mL of the organic solvent in step 1) was added to the aqueous phase in step 3) and dispersed under shearing for 5 min, and then added with the drug solution in step 2) and continuously dispersed under shearing for 5 min to obtain a crude emulsion;
   5) The crude emulsion was transferred to a high pressure homogenizer and homogenized under a pressure of 1300-1500 bar for 2-7 min;
   6) Rotary evaporation was performed at 40° C.-45° C. for 4-8 min;
   7) Filtration was performed through a 0.2 μm PES syringe filter membrane. Before and after filtration, the parameters such as particle size, encapsulation efficiency, and loading of drug of the product samples were measured.
   8) The particle size of the obtained products was measured again after storage in refrigerator at 4° C. overnight.

2. Measurement Results

The measurement results of the parameters of the prepared HSA-SN-38 product are shown in Table 21.

TABLE 21

Measurement Results of Parameters of HSA-SN-38 Product Prepared by Different Preparation Process

| Sample | Particle Size Before Passing Through Membrane/PDI (nm/—) | Particle Size After Passing Through Membrane/PDI (nm/—) | Particle Size After Storage at 4° C. Overnight/PDI (nm/—) | Loading of drug (%) | Absolute SN-38 Recovery (%) |
|---|---|---|---|---|---|
| Product of Example 15 | 156.2 nm/0.243 | 121.1 nm/0.210 | 145.5 nm/0.203 | 8.41 | 60.04 |

The results show that the HSA-SN-38 product prepared by firstly treating the albumin solution with a small amount of the organic solvent and then adding the drug solution exhibited excellent parameters, especially a higher loading of drug.

Example 16: Preparation of rHA-SN-38 Products Prepared Using Other Lipids rHA-SN-38 products were prepared according to the preparation process of Example 1 and tested, except that the cholesterol in step 2) of the preparation process of Example 1 was replaced with the lipids in Table 22 below (cholesteryl palmitate (Chol-PA, TCI Co., Ltd.); glyceryl monostearate (SA-Gly, damas-beta Co., Ltd.); and vitamin D3 (Aladdin Reagent Co., Ltd.)). The particle sizes of the obtained products were also measured after storage in refrigerator at 4° C. overnight. The measurement results of the parameters of the rHA-SN-38 products are shown in Table 22.

TABLE 22

Measurement Results of Parameters of rHA-SN-38 Products Prepared Using Other Lipids

| Lipid and Amount | Particle Size Before Passing Through Membrane/PDI (nm/—) | Particle Size After Passing Through Membrane/PDI (nm/—) | Particle Size After Storage at 4° C. Overnight/PDI (nm/—) | Loading of drug (%) | Absolute SN-38 Recovery (%) |
|---|---|---|---|---|---|
| 30 mg Chol-PA | 184.4/0.255 | 128.1/0.238 | 165.3/0.281 | 4.74 | 38.43 |
| 60 mg Chol-PA | 177.0/0.265 | 121.5/0.283 | 131.7/0.283 | 5.34 | 44.43 |
| 90 mg Chol-PA | 151.1/0.342 | 100.1/0.290 | 119.5/0.409 | 5.50 | 49.00 |
| 30 mg Vitamin D3 | 172.7/0.224 | 111.5/0.271 | — | 2.76 | 35.83 |
| 30 mg SA-Gly | 183.6/0.211 | 141.3/0.160 | 458.1/0.546 | 7.04 | 65.99 |

The results show that the products with a homogeneous particle size and high loading of drug can be obtained in case of Chol-PA and SA-Gly. The higher the amount of Chol-PA, the smaller the particle size of the product and the higher the absolute SN-38 recovery and the loading of drug. However, the particle size distribution was widened. The product prepared by adding SA-Gly had a larger particle size and higher absolute SN-38 recovery and loading of drug, but poorer stability.

Example 17: Preparation of rHA-SN-38 Products Prepared Using Lipid Combinations

Except that the cholesterol in step 2) of the preparation process of Example 1 was replaced with the lipid combinations shown in Table 23 below, rHA-SN-38 products were prepared according to the preparation process of Example 1 and tested. The particle sizes of the obtained products were also measured after storage in refrigerator at 4° C. overnight. The measurement results of the parameters of the rHA-SN-38 products are shown in Table 23.

TABLE 23

Measurement Results of Parameters of rHA-SN-38 Products Prepared Using Lipid Combinations

| Additive and Amount | Particle Size Before Passing Through Membrane/PDI (nm/—) | Particle Size After Passing Through Membrane/PDI (nm/—) | Particle Size After Storage at 4° C. Overnight/PDI (nm/—) | Loading of drug (%) | Absolute SN-38 Recovery (%) |
|---|---|---|---|---|---|
| 30 mg Chol + 15 mg Chol-PA | 178.6/0.281 | 112.6/0.241 | 131.2/0.213 | 4.43 | 43.43 |
| 30 mg Chol + 30 mg Chol-PA | 157.5/0.278 | 101.3/0.232 | 114.0/0.186 | 5.12 | 46.55 |
| 15 mg Chol + 30 mg Chol-PA | 176.2/0.290 | 103.2/0.230 | 114.9/0.197 | 4.05 | 35.63 |
| 30 mg Chol + 30 mg SA-Gly | 213.6/0.235 | 168.8/0.202 | — | 5.52 | 49.71 |
| 30 mg Chol-PA + 30 mg SA-Gly | 195.6/0.226 | 143.7/0.183 | 153.6/0.152 | 5.19 | 41.49 |

The results show that by adding Chol-PA to the formulation, the particle size of the product can be reduced; and the larger the amount added, the smaller the particle size and the better stability of the product. The product prepared by adding SA-Gly to the formulation had a large particle size but reduced particle size distribution. The product prepared by adding both Chol-PA and SA-Gly had lower particle size distribution and good storage stability.

Example 18: Preparation of rHA-SN-38 Products Prepared with Increased Lipid Proportion Except that the amount of the cholesterol was 60 mg, other raw materials in this example were the same with Example 1. To obtain liquid and lyophilized powder formulations, the raw materials were divided into two groups for preparing the liquid formulation by the method of Example 1 and preparing the lyophilized powder formulation by the method of Example 2 (step 7 was not performed), respectively. The measurement results of the parameters of the obtained liquid and lyophilized powder formulations of rHA-SN-38 are shown in the following table:

| Liquid Formulation | | | Lyophilized Powder | | |
|---|---|---|---|---|---|
| Particle Size Before Lyophilization/PDI (nm/—) | Loading of drug (%) | rHA Multimer Content (%) | Particle Size After reconstitution/PDI (nm/—) | Loading of drug (%) | rHA Multimer (%) |
| 142.5/0.259 | 4.56 | 0.95 | 164.0/0.226 | 4.4 | 0.57 |

Example 19: Large-Scale Preparation of HSA-SN-38 Product

The pilot-scale preparation process was studied on the basis of the foregoing small-scale preparations and the HSA-SN-38 product of this example was prepared under a large-scale condition.

1. Preparation Process
   1) A mixed organic solvent of EtOH (152 mL) and CHCl$_3$ (228 mL) was prepared;
   2) 3.36 g of SN-38 and 4.8 g of cholesterol were taken, dissolved completely in the organic solvent in step 1), and incubated at 50° C. for 30 min or more to obtain a drug solution;
   3) An aqueous solution (3360 mL) of HSA (32 g) was prepared with deionized water as an aqueous phase;
   4) Shearing dispersion: after the drug solution in step 2) was mixed with the aqueous phase in step 3), shearing dispersion was performed for 10-15 min to obtain a crude emulsion;
   5) The crude emulsion was transferred to a high pressure homogenizer and homogenized for 10 cycles under a pressure of 900-1200 bar;
   6) A sucrose solution (100 g/L, 2.16 L) was added to the product obtained in step 5) and mixed;
   7) The mixture obtained in step 6) was evaporated by rotary evaporation under 60-70 mbar, and the sample was concentrated using tangential flow ultra-filtration (Suzhou Saiensi Instrument Co., Ltd.);
   8) A bag filter (Sartorius, SARTOBRAN P) was used for filtration. Samples were taken before and after filtration for measuring the particle size and the encapsulation effect. The filtrate was filled in vials and lyophilized in vacuum to obtain a lyophilized formulation of HSA-SN-38 nanoparticles.
2. Measurement Results
(1) Particle Size Result
   The particle size of the filtrate sample prepared in step 8) was 124.6 nm (PDI=0.187).
(2) Encapsulation Effect 3. Disintegration Experiment The prepared lyophilized formulation was reconstituted with 1×PBS at pH of 7.4 to the concentration of 1 mg/mL of SN-38, and then gradiently diluted to 100 μg/mL, 10 μg/mL, 1 μg/mL, 0.1 g/mL, and 0.01 μg/mL, and the particle size and the particle size distribution under different concentrations were measured.

Figure 6:
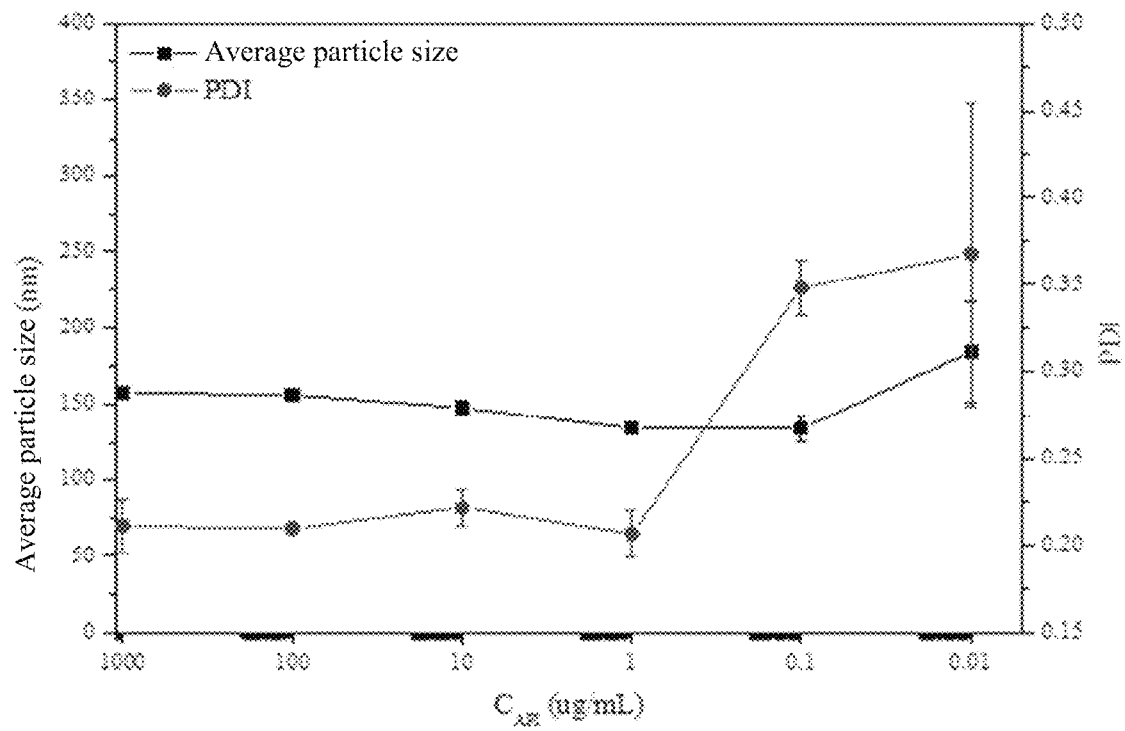
FIG. 6 shows the results of a disintegration experiment conducted under gradient dilution in Example 19.

The obtained results are as shown in FIG. 6. The results show that the HSA-SN-38 nanoparticles began to disintegrate when the concentration of SN-38 was less than 1 μg/mL and disintegrated slowly when the concentration of SN-38 reached 0.01 ug/mL. This indicates that the HSA-SN-38 lyophilized product prepared in Example 19 had excellent stability and was greatly superior to other albumin nanoformulations commercially available at present.

Example 20: Large-Scale Preparation of HSA-SN-38 Product

The pilot-scale preparation process was studied on the basis of the foregoing small-scale preparations and the HSA-SN-38 product of this example was prepared under a large-scale condition.

1. Preparation Process
   1) A mixed organic solvent of EtOH (222 mL) and CHCl$_3$ (333 mL) was prepared;
   2) 4.41 g of SN-38 and 6.30 g of cholesterol were taken, dissolved completely in 480 mL of the organic solvent in step 1), incubated at 50° C. for 30 min or more, and then mixed with the remaining organic solvent to obtain a drug solution;
   3) An aqueous solution (3360 mL) of HSA (32 g) was prepared with deionized water as an aqueous phase;
   4) Shearing dispersion: after the drug solution in step 2) was mixed with the aqueous phase in step 3), shearing dispersion was performed for 10-15 min to obtain a crude emulsion;
   5) The crude emulsion was transferred to a high pressure homogenizer and homogenized for 10 cycles under a pressure of 900-1200 bar;
   6) A sucrose solution (36 g/L, 6 L) was added to the product obtained in step 5) and mixed;
   7) The mixture obtained in step 6) was evaporated by rotary evaporation under 60-70 mbar, and the sample was concentrated using tangential flow ultra-filtration (Suzhou Saiensi Instrument Co., Ltd.);
   8) A bag filter (Sartorius, SARTOBRAN P) was used for filtration. Samples were taken before and after filtration for measuring the particle size and the encapsulation effect. The filtrate was filled in vials and lyophilized in vacuum to obtain a lyophilized formulation of HSA-SN-38 nanoparticles.

TABLE 24

Encapsulation Effect of Filtrate Sample Prepared in Step 8) of Example 19

| Concentration of SN-38 (mg/mL) | Relative SN-38 Recovery (%) | Absolute SN-38 Recovery (%) | SN-38 Purity (%) | HSA Content (mg/mL) | HSA Multimer Content (%) | Absolute HSA Recovery (%) | Organic Solvent Residue (mg/mL) | Loading of drug (%) |
|---|---|---|---|---|---|---|---|---|
| 0.605 | 73.083 | 57.638 | 99.851 | 6.7 | 0.5 | 66.608 | Ethanol 0.76; chloroform 0.0049 | 8.329 |

Notes:
the relative SN-38 recovery (%) represents the percentage of the concentration difference of SN-38 in the sample before and after passing through the membrane, relative to the concentration of SN-38 in the sample before passing through the membrane; and the absolute HSA recovery (%) represents the percentage of the amount of HSA in the product after passing through the membrane relative to the amount of HSA feeded.

2. Measurement Results
(1) Particle Size Result
The particle size of the filtrate sample prepared in step 8) was 146.9 nm (PDI=0.208).
(2) Encapsulation effect

TABLE 25

Encapsulation Effect of Filtrate Sample Prepared in Step 8) of Example 20

| SN-38 Content (mg/mL) | Relative SN-38 Recovery (%) | Absolute SN-38 Recovery (%) | SN-38 Purity (%) | HSA Content (mg/mL) | HSA Multimer Content (%) | Absolute HSA Recovery (%) | Organic Solvent Residue (mg/mL) | Loading of drug (%) |
|---|---|---|---|---|---|---|---|---|
| 0.772 | 71.015 | 46.236 | 99.882 | 8.5 | 0.1 | 69.838 | Ethanol 1.18; chloroform 0.0048 | 8.358 |

3. Disintegration Experiment

The prepared lyophilized formulation was reconstituted with water for injection to the concentration of 1 mg/mL of SN-38, and then gradiently diluted to 100 μg/mL, 10 μg/mL, 1 μg/mL, 0.1 g/mL, and 0.01 μg/mL, and the particle size and the particle size distribution under different concentrations were measured.

Figure 7:
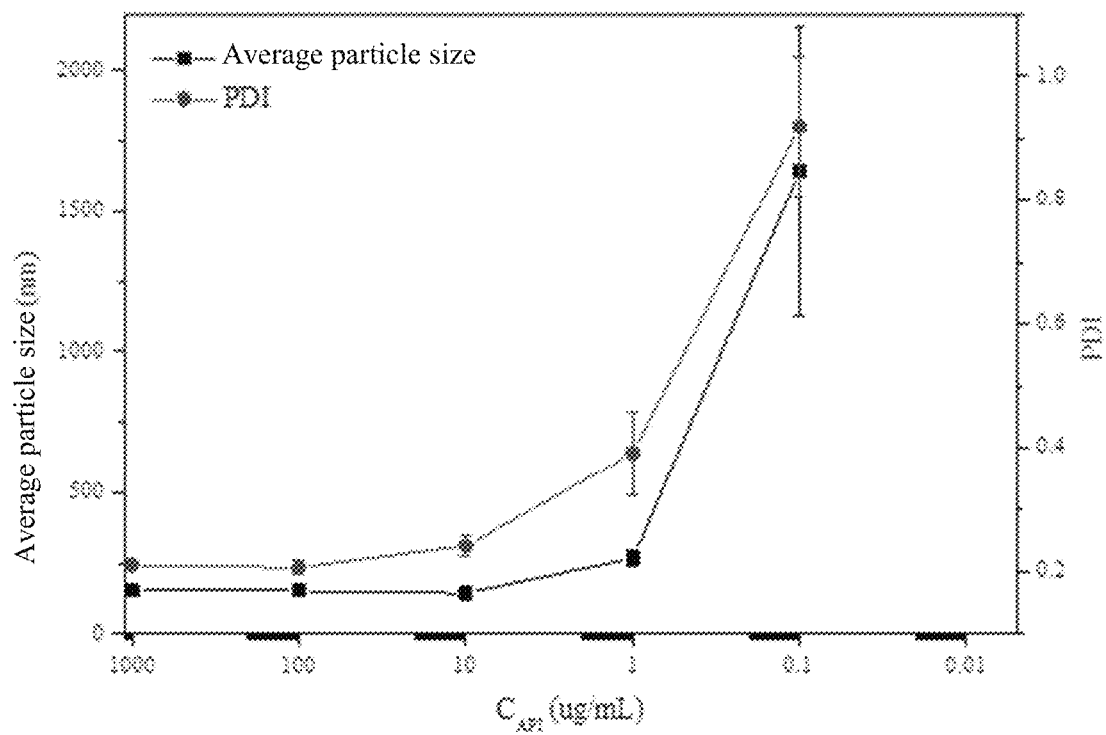
FIG. 7 shows the results of a disintegration experiment conducted under gradient dilution in Example 20.

The obtained results are as shown in FIG. 7. The results show that similar to the product of Example 19, the HSA-SN-38 product of this example began to disintegrate with a significantly widened particle size distribution when the concentration of SN-38 was less than about 1 μg/mL, and disintegrated rapidly when the concentration of SN-38 reached 0.1 ug/mL. The HSA-SN-38 product of this example still had good stability and was obviously superior to other commercially available albumin nanoformulations.

Example 21: Toxicity Study on rHA-SN-38 Product of Example 1

A pharmacodynamic experiment was conducted on the rHA-SN-38 product prepared in Example 1 in a subcutaneously implanted tumor model of human Hep 3B cells (ATCC HB-8064 cells) in BALB/c nude mice, and the safety was evaluated at the same time.

Figure 8:
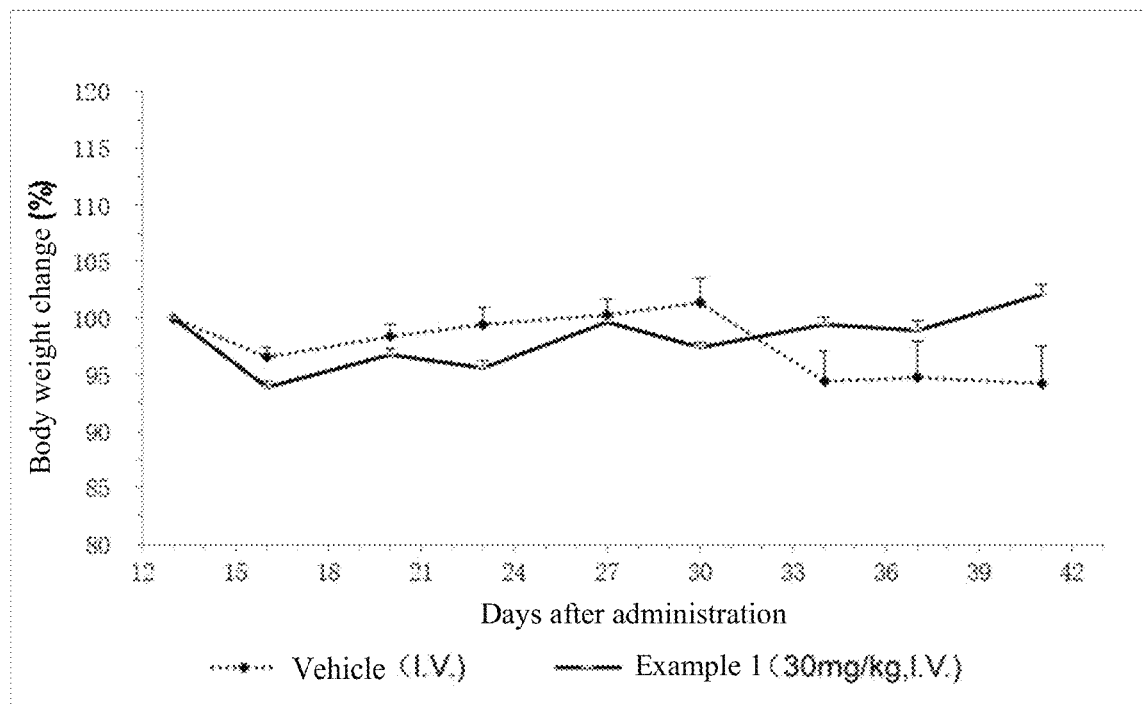
FIG. 8 shows body weight changes of animals administrated with the rHA-SN-38 product of Example 1 in Example 21.

By tail intravenous injection, the selected qualified tumor-bearing BALB/c nude mice (5 mice in each group) were administered with the rHA-SN-38 product (30 mg/kg) of Example 1 once a week, for 6 consecutive weeks. The body weights of the animals were measured on days 13, 16, 20, 23, 27, 30, 34, 37, and 41 after administration. The results are as shown in FIG. 8.

The results show that the product (30 mg/kg) of Example 1 had no influence on the body weights of the animals, and had good safety and good tumor inhibition efficacy.

Example 22: Study on Anti-Breast Tumor Activity of rHA-SN-38 Product

A pharmacodynamic experiment was conducted on the rHA-SN-38 product prepared in Example 1 in a subcutaneously implanted tumor model of human triple-negative breast cancer MDA-MB-231 (ATCC: CRM-HTB-26™) in BALB/c nude mice to study the use of the composition according to the invention in cancer treatment.

The study was carried out according to two protocols.
Protocol I:

21 Qualified tumor-bearing BALB/c nude mice were selected and randomly divided into 3 groups, with 7 mice in each group, and administered with sterile water for injection, commercially available irinotecan hydrochloride injection (60 mg/kg), and the rHA-SN-38 product (15 mg/kg), respectively. By tail intravenous injection, the mice were administered twice a week, for 3 consecutive weeks. The day of the first administration was taken as day 0, and the tumor volume of each animal was measured on this day. During the administration, general clinical manifestations of the animals were observed each day, and the body weights and the tumor volumes were measured twice a week.

The experimental results are shown in Table 26. The rHA-SN-38 product of the invention had extremely significant tumor inhibition effect in the subcutaneously implanted tumor model of human triple-negative breast cancer MDA-MB-231 in BALB/c nude mice and was obviously superior to the commercially available irinotecan hydrochloride injection. After 3 doses, the tumor inhibition rate of the rHA-SN-38 product (15 mg/kg) was 95% and the tumor inhibition rate of the commercially available irinotecan hydrochloride injection (60 mg/kg) was 71%.

TABLE 26

Therapeutic Effect of rHA-SN-38 Product on Subcutaneously Implanted Tumor of Human Triple-Negative Breast Cancer Mda-Mb-231 in Nude Mice

| Group | Administered Dose (mg/kg) | Tumor Volume on Day 0 (mm³) | Tumor Volume on Day 16 (mm³) | Tumor Inhibition Rate (%) |
|---|---|---|---|---|
| Water for Injection | — | 138 | 2624 | — |
| rHA-SN-38 Product | 15 | 143 | 128 | 95 |
| Commercial irinotecan hydrochloride injection | 60 | 141 | 754 | 71 |

Protocol II:

42 Qualified tumor-bearing BALB/c nude mice were selected and randomly divided into 6 groups, with 7 mice in each group, and administered with sterile water for injection, commercially available irinotecan hydrochloride injection (60 mg/kg, 80 mg/kg), rHA (220 mg/kg), and the rHA-SN-38 product (1.67 mg/kg, 5 mg/kg, 15 mg/kg), respectively. By tail intravenous injection, the mice were administered once a week, for 3 consecutive weeks. The day of the first administration was taken as day 0, and the tumor volume of each animal was measured on this day. During the administration, general clinical manifestations of the animals were observed each day, and the body weights and the tumor volumes were measured twice a week.

Figure 9:
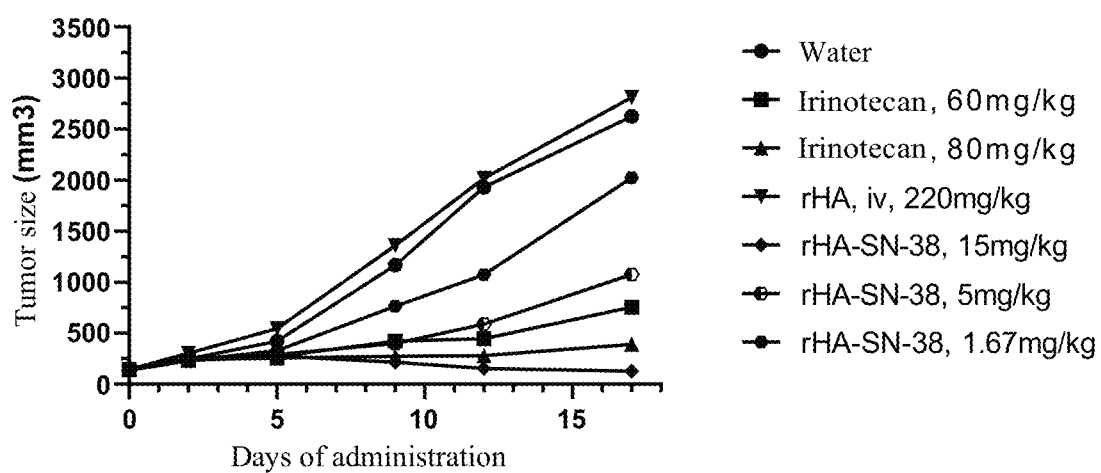
FIG. 9 shows the results of inhibiting human triple-negative breast cancer MDA-MB-23 with the product of Example 1 in an in vivo experiment.

Experimental results are as shown in FIG. 9. As shown in FIG. 9, the employed different doses of rHA-SN-38 product exhibited an excellent advantage in tumor inhibition which was dose-dependent.

As shown by the above experimental results, the rHA-SN-38 product of the invention was low in administration dose and high in tumor inhibition rate, had significantly better therapeutic effect than the commercially available irinotecan hydrochloride injection, and had excellent therapeutic effect on human triple-negative breast cancer.

Example 23: Study on Anti-Colon Cancer Activity (HT-29) of rHA-SN-38 Product The rHA-SN-38 lyophilized powder product prepared in Example 2 was reconstituted and subjected to a pharmacodynamic experiment in a subcutaneously implanted tumor model of human colon cancer HT-29 (ATCC: HTB 3B™) in BALB/c nude mice to study the use of the composition of the invention in cancer treatment.

The study was carried out according to two protocols.

Protocol I:

21 Qualified tumor-bearing BALB/c nude mice were selected and randomly divided into 3 groups, with 7 mice in each group, and administered with sterile water for injection, commercially available irinotecan hydrochloride injection (60 mg/kg), and the rHA-SN-38 product (30 mg/kg), respectively. By tail intravenous injection, the mice were administered once a week, for 3 consecutive weeks. The day of the first administration was taken as day 0, and the tumor volume of each animal was measured on this day. During the administration, general clinical manifestations of the animals were observed each day, and the body weights and the tumor volumes were measured twice a week.

The experimental results are as shown in Table 27. The rHA-SN-38 product (30 mg/kg) of the invention had extremely significant tumor inhibition effect in the subcutaneously implanted tumor model of human colon cancer HT-29 in BALB/c nude mice and was obviously superior to the commercially available irinotecan hydrochloride injection (60 mg/kg). After 4 doses, the tumor inhibition rate of the rHA-SN-38 product (30 mg/kg) was 72% and the tumor inhibition rate of the commercially available irinotecan hydrochloride injection (60 mg/kg) was 47%.

TABLE 27

Therapeutic Effect of rHA-SN-38 Product on Subcutaneously Implanted Tumor of Human Colon Cancer HT-29 in Nude Mice

| Group | Administered Dose (mg/kg) | Tumor Volume on Day 0 (mm$^3$) | Tumor Volume on Day 26 (mm$^3$) | Tumor Inhibition Rate (%) |
| --- | --- | --- | --- | --- |
| Water for Injection | — | 97 | 1082 | — |
| rHA-SN-38 Product | 30 | 99 | 308 | 72 |
| Commercially irinotecan hydrochloride injection | 60 | 97 | 578 | 47 |

Protocol II:

15 Qualified tumor-bearing BALB/c nude mice were selected and randomly divided into 3 groups, with 5 mice in each group, and administered with sterile water for injection, commercially available irinotecan hydrochloride injection (60 mg/kg, 80 mg/kg), and the rHA-SN-38 product (3.3 mg/kg, 10 mg/kg, 30 mg/kg), respectively. By tail intravenous injection, the mice were administered once a week, for 4 consecutive weeks. The day of the first administration was taken as day 0, and the tumor volume of each animal was measured on this day. During the administration, general clinical manifestations of the animals were observed each day, and the body weights and the tumor volumes were measured twice a week.

Figure 10:
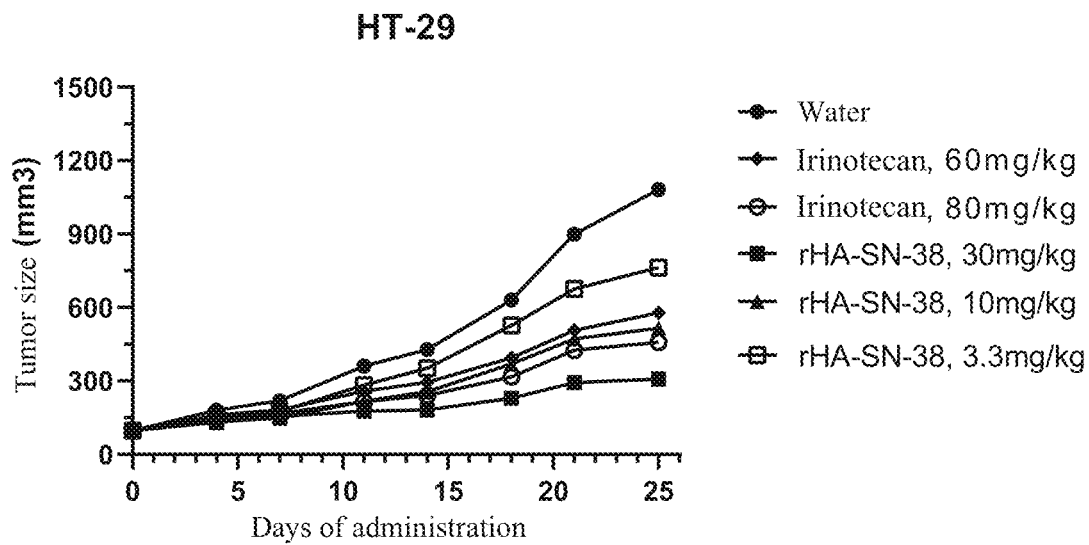
FIG. 10 shows results of inhibiting human colon cancer HT-29 with the product of Example 2 in an in vivo experiment.

As shown in FIG. 10, different doses of rHA-SN-38 product exhibited excellent advantage in tumor inhibition which was dose-dependent.

As shown by the above experimental results, the rHA-SN-38 product of the invention was low in administration dose and high in tumor inhibition rate, had significantly better therapeutic effect than the commercially available irinotecan hydrochloride injection, and had excellent therapeutic effect on human colon cancer.

Example 24: In Vivo Pharmacodynamic Study on MDA-MB-231 Tumor

Objective: the antitumor activity of different doses of the HSA-SN-38 product of Example 19 (administered after reconstituted in a vehicle) were evaluated in a subcutaneous xenograft model of human triple-negative breast cancer cell line MDA-MB-231 (ATCC: CRM-HTB-26™) in BALB/c nude mice, and compared with that of the commercially available irinotecan hydrochloride (CPT-11) for injection.

1. Experiment Design

TABLE 28

Experiment Design for Antitumor Effects of Test Agents in MDA-MB-231 Human Breast Cancer Model

| Group | Treatment | Number of Animals | Dose (mg/kg) | Administration Route | c Volume (mL/kg) | Dosage Regimen |
| --- | --- | --- | --- | --- | --- | --- |
| 1 | Vehicle (Blank) | 7 | — | iv | 10 | QW × 3 |
| 2 | CPT-11 | 7 | 60 | iv | 10 | QW × 3 |
| 3 | CPT-11 | 7 | 80 | iv | 10 | QW × 3 |
| 4 | A01S | 7 | 240 | iv | 10 | QW × 3 |
| 5 | HSA-SN-38 | 7 | 15 | iv | 10 | QW × 3 |
| 6 | HSA-SN-38 | 7 | 5 | iv | 10 | QW × 3 |
| 7 | HSA-SN-38 | 7 | 1.67 | iv | 10 | QW × 3 |

Notes:
QW: dosed once a week.

A01S: human serum albumin (Guang Dong Shuang Lin Bio-Pharmacy Co., Ltd.) was used as negative control.

2. Experimental Method

49 Balb/c female nude mice (6-8 weeks old) were selected, and MDA-MB-231 tumor masses were inoculated to the right scapulas of the nude mice. The animals were randomly grouped (7 animals in each group) 16 days after the inoculation of the tumor masses, and administered by tail intravenous injection. One week after the last administration, tumors were taken from all the mice and weighed.

3. Experimental Observation and Data Collection

After the inoculation of the tumor cells, in addition to observing the tumor growth, the influence of treatment on animal behaviors was also detected, including the activity, food and water intake, body weight change (the body weight was measured twice a weak), as well as any abnormalities in the eyes, fur and other conditions of the test animals. The clinical symptoms observed during the experiment were recorded in the raw data. Tumor volume was calculated by the following formula:

$$\text{Tumor volume } (mm^3) = 1/2 \times (a \times b^2)$$

(a representing the long diameter and b representing the short diameter).

When the body weight of an individual animal decreased by more than 15% (BWL>15%), the administration to the individual animal was stopped, and resumed when the body weight decrease recovered to below 10%. When the body weight of the individual animal decreased by more than 20%, the individual animal was euthanatized according to animal welfare regulations.

4. Evaluation Criteria for Therapeutic Effect

Relative tumor proliferation rate (T/C (%)) represents a ratio in percentage of relative tumor volumes or tumor weights of a treatment group and a control group at a time point, which was calculated by the following formula:

$$T/C(\%) = T_{RTV}/C_{RTV} \times 100\%$$

wherein $T_{RTV}$ was the average RTV of the treatment group; and $C_{RTV}$ was the average RTV of the vehicle control group;

wherein:

$$RTV = V_t/V_0,$$

wherein $V_0$ was the tumor volume of an animal when grouping, and $V_t$ was the tumor volume of the animal after treatment;

or $$T/C\% = T_{TW}/C_{TW} \times 100\%$$

wherein $T_{TW}$ was the average tumor weight of the treatment group at the end of the experiment; and $C_{TW}$ was the average tumor weight of the vehicle control group at the end of the experiment.

Relative tumor inhibition rate (TGI (%)) was calculated by the following formula:

$$TGI(\%) = (1 - T/C) \times 100\%,$$

wherein T and C were the relative tumor volumes (RTVs) or tumor weights (TWs) of the treatment group and the control group at a particular time point, respectively.

5. Statistical Analysis

The average values of the tumor of different groups were compared using one-way ANOVA in the experiment. Analysis of homogeneity of variance showed a significant difference in the F value, and multiple comparison was performed using Dunnet's T3 (heterogeneous variance) method after the ANOVA analysis. Analysis on all data was performed using SPSS 17.0. $p<0.05$ was considered to indicate a significant difference.

Figure 11:
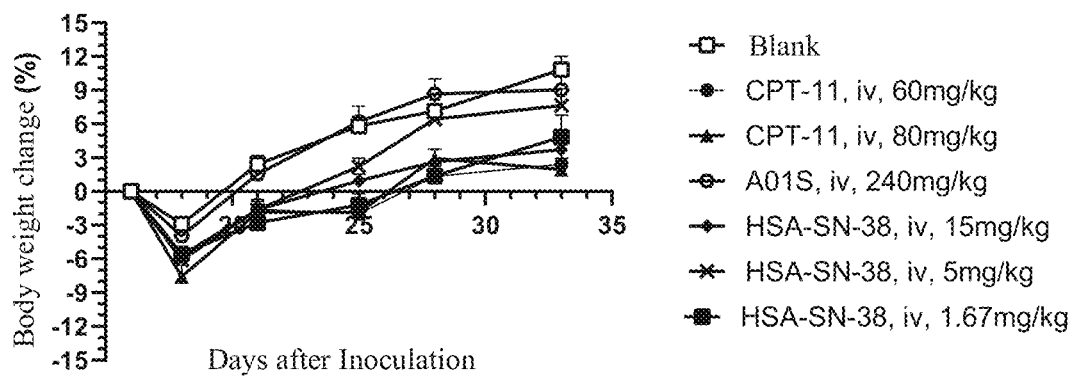
FIG. 11 shows body weight changes of test animals in Example 24.
Figure 12:
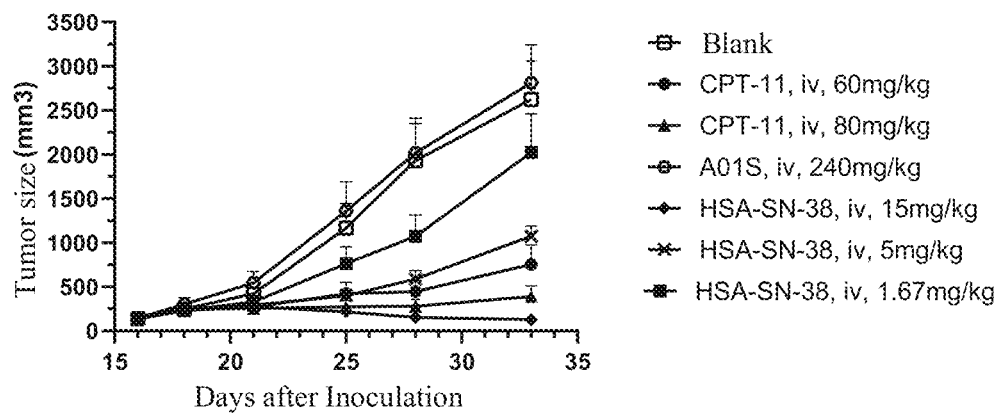
FIG. 12 shows tumor volume changes of test animals in Example 24.

6. Experimental Results 6.1 Body Weight Change: as shown in FIG. 11.
6.2 Tumor Volume Change: as shown in FIG. 12.
6.3 Antitumor Efficacy Evaluation Indicators The following Table 29 shows the evaluation indicators for tumor inhibition efficacy of agents such as HSA-SN-38 and CPT-11 in the MDA-MB-231 xenograft model.

TABLE 29

Analysis on Efficacy in Each Treatment Group in MDA-MB-231 Human Breast Cancer Model

| Agent | $N^a$ | Tumor Volume (mm³) D16 | Tumor Volume (mm³) D33 | RTV (D33) | Tumor Weight (mg) (D33) | T/C (%) RTV | T/C (%) TW | p Value TV | p Value TW |
|---|---|---|---|---|---|---|---|---|---|
| Vehicle | 7/7 | 138 ± 22 | 2624 ± 433 | 19.01 ± 1.31 | 2451 ± 354 | 100 | 100 | 1.000 | 1.000 |
| CPT-11 60 mg/kg | 7/7 | 141 ± 23 | 754 ± 218 | 4.59 ± 1.04 | 680 ± 212 | 24 | 28 | 0.058 | 0.027 |
| CPT-11 80 mg/kg | 7/6 | 144 ± 27 | 389 ± 120 | 2.46 ± 0.41 | 391 ± 143 | 13 | 16 | 0.023 | 0.011 |
| A01S 240 mg/kg | 7/7 | 145 ± 27 | 2811 ± 432 | 20.67 ± 2.65 | 2399 ± 304 | 109 | 98 | 1.000 | 1.000 |
| HSA-SN-38 15 mg/kg | 7/7 | 143 ± 28 | 128 ± 25 | 0.89 ± 0.05 | 69 ± 17 | 5 | 3 | 0.015 | 0.007 |
| HSA-SN-38 5 mg/kg | 7/7 | 143 ± 28 | 1074 ± 116 | 8.42 ± 1.02 | 920 ± 90 | 44 | 38 | 0.130 | 0.057 |

TABLE 29-continued

Analysis on Efficacy in Each Treatment Group in MDA-MB-231 Human Breast Cancer Model

| Agent | N[a] | Tumor Volume (mm³) D16 | Tumor Volume (mm³) D33 | RTV (D33) | Tumor Weight (mg) (D33) | T/C (%) RTV | T/C (%) TW | p Value TV | p Value TW |
|---|---|---|---|---|---|---|---|---|---|
| HSA-SN-38 1.67 mg/kg | 7/7 | 135 ± 19 | 2022 ± 438 | 16.98 ± 4.16 | 1641 ± 367 | 89 | 67 | 0.998 | 0.873 |

Notes:
[a]representing the number of animals before administration/the number of animals at the end of the experiment 7. Conclusion The high dose of HSA-SN-38 (15 mg/kg) had an obvious tumor inhibition effect and was superior to CPT-11. At the end of the experiment (day 33 after the tumor inoculation), after 3 doses, the high-dosed HSA-SN-38 group had the tumor volume of 128 mm³, the RTV of 0.89, the T/C value of 5%, and p=0.015. The intermediate dose of HSA-SN-38 (5 mg/kg) also had a certain inhibition effect on tumor growth, but was not significantly different from the vehicle group (p=0.130). No obvious antitumor activity was observed in the low-dosed (1.67 mg/kg) HSA-SN-38 treatment group. The analysis result of the tumor weights was substantially consistent with that of the tumor volume.

The influence on the body weight change of the tumor-bearing mice in each group was as shown in FIG. 11. During the experiment, in the high-dosed (80 mg/kg) CPT-11 treatment group, one animal died and the remaining 6 animals had no obvious reduction in body weight after the second dose. At the end of the experiment, the body weight increased by 1.950% as compared with that before administration. No animal died in the low-dosed (60 mg/kg) CPT-11 treatment group, and after the last dose, the body weight increased by 2.41% as compared with that before administration. No animal died and no any other abnormal toxic reaction was observed in the groups of three doses of HSA-SN-38. After the last dose, the body weight increased to different extents as compared with that before administration, the body weight increase in the groups of high, intermediate, and low doses were 3.70%, 7.63%, and 4.85%, respectively. The body weight increase in the vehicle and A01S control groups were the most obvious, which, at the end of the experiment, were 10.84% and 9.04% as compared with that before administration, respectively.

To sum up, HSA-SN-38 at a dose of 15 mg/kg had a significant effect in inhibiting tumor growth in the MDA-MB-231 human breast cancer model. Likewise, CPT-11 at a dose of 80 mg/kg had a significant effect in inhibiting tumor growth which, however, was weaker than that of the high-dosed HSA-SN-38 group; and one animal died after the second drug administration. On the whole, HSA-SN-38 had stronger antitumor activity than CPT-11 and had good tolerance, led to no animal death and no other toxic reaction observed during the experiment.

Example 25: In Vivo Pharmacodynamic Study on HCT116 Tumor

Objective: the antitumor activity of HSA-SN-38 (administered after reconstituted in a vehicle) prepared in Example 20 in a subcutaneous xenograft model of human colon cancer cell line HCT116 (ATCC CCL-247) in BALB/c nude mice was verified, and compared with that of the commercially available irinotecan hydrochloride (CPT-11) for injection.

1. Experiment Design

TABLE 30

Experiment Design for Antitumor Effects of Test Agents in Human Colon Cancer Cell Line HCT116

| Group | Treatment | Number of Animals | Dose (mg/kg) | Administration Route | Dose Volume (mL/kg) | Dosage Regimen |
|---|---|---|---|---|---|---|
| 1 | Vehicle (Blank) | 7 | — | iv | 10 | QW × 4 |
| 2 | CPT-11 | 7 | 60 | iv | 10 | QW × 4 |
| 3 | CPT-11 | 7 | 80 | iv | 10 | QW × 4 |
| 4 | A01S | 7 | 450 | iv | 10 | QW × 4 |
| 5 | HSA-SN-38 | 7 | 30 | iv | 10 | QW × 4 |
| 6 | HSA-SN-38 | 7 | 10 | iv | 10 | QW × 4 |
| 7 | HSA-SN-38 | 7 | 3.3 | iv | 10 | QW × 4 |

2. Experimental Method

The HCT116 tumor mass in a good state was cut into small tumor masses of 20-30 mm³ which were inoculated to the right scapulas of 70 nude mice in total. When the average tumor volume reached about 121 mm³ 15 days after the inoculation of the tumor masses, the mice with excessively small or large tumor volumes were screened out, and the remaining 49 mice were randomly grouped (7 groups, with 7 mice in each group) by tumor volume and administered (by tail intravenous injection) once a week, for a total of 4 weeks. The therapeutic effect was evaluated based on relative tumor inhibition rate (TGI), and the safety was evaluated based on the body weight change and death of the animals. One week after the last dose, tumors were taken from all mice, weighed, and photographed.

3. Statistical Analysis

The average values of the tumor of different groups were compared using one-way ANOVA in the experiment. Analysis of homogeneity of variance showed a significant difference in the F value, and multiple comparison was performed using Dunnet's T3 (heterogeneous variance) method after the ANOVA analysis. Analysis on all data was performed using SPSS 17.0. $p<0.05$ was considered to indicate a significant difference.

Figure 13:
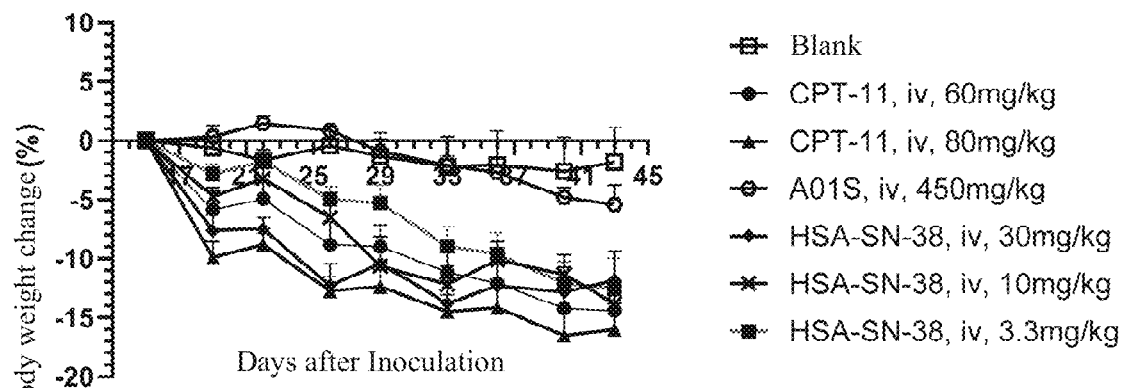
FIG. 13 shows body weight changes of test animals in Example 25.

4. Experimental Results 4.1 Body Weight Change: as shown in FIG. 13.

4.2 Tumor Volume Change

Figure 14:
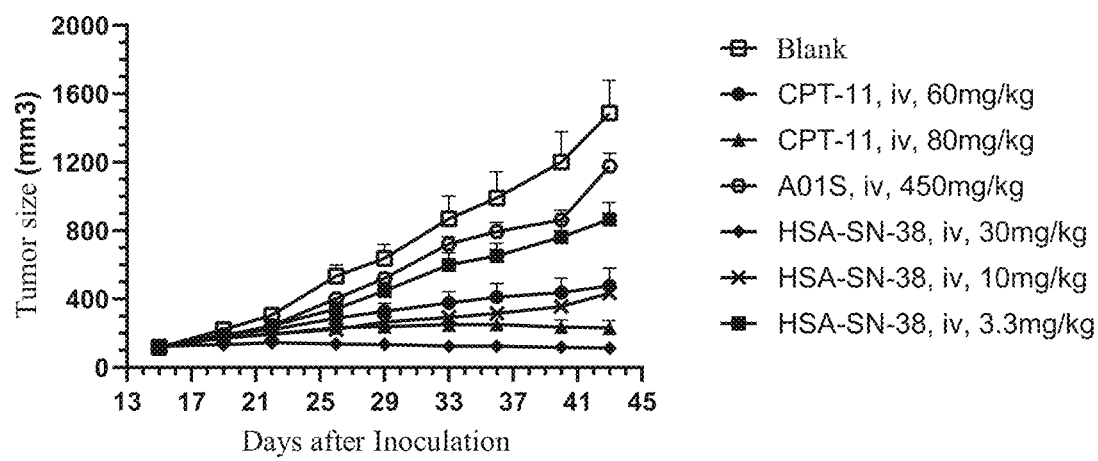
FIG. 14 shows tumor volume changes of test animals in Example 25.

The tumor volume change of different groups is as shown in Table 31 and FIG. 14.

TABLE 31

Tumor Volume of Animals of Different Groups at Different Time points

Tumor Volume (mm³, Mean ± SEM)

| Time (D) | Blank | CPT-11 60 mg/kg | CPT-11 80 mg/kg | A01S 450 mg/kg | HSA-SN-38 30 mg/kg | HSA-SN-38 10 mg/kg | HSA-SN-38 3.3 mg/kg |
|---|---|---|---|---|---|---|---|
| 15 | 117 ± 13 | 117 ± 15 | 119 ± 15 | 117 ± 14 | 123 ± 18 | 124 ± 20 | 117 ± 12 |
| 19 | 221 ± 31 | 194 ± 36 | 171 ± 21 | 184 ± 23 | 134 ± 21 | 175 ± 38 | 184 ± 19 |
| 22 | 306 ± 40 | 221 ± 36 | 194 ± 24 | 244 ± 36 | 144 ± 20 | 194 ± 35 | 243 ± 30 |
| 26 | 533 ± 66 | 287 ± 44 | 233 ± 30 | 403 ± 37 | 138 ± 28 | 222 ± 34 | 342 ± 40 |
| 29 | 637 ± 82 | 327 ± 48 | 238 ± 32 | 521 ± 28 | 135 ± 24 | 265 ± 27 | 447 ± 50 |
| 33 | 869 ± 133 | 378 ± 65 | 249 ± 37 | 723 ± 41 | 125 ± 22 | 293 ± 29 | 599 ± 72 |
| 36 | 990 ± 154 | 411 ± 79 | 252 ± 39 | 794 ± 54 | 125 ± 23 | 316 ± 34 | 653 ± 72 |
| 40 | 1200 ± 177 | 437 ± 85 | 236 ± 43 | 863 ± 57 | 117 ± 20 | 355 ± 37 | 763 ± 90 |
| 43 | 1487 ± 193 | 477 ± 103 | 231 ± 44 | 1176 ± 77 | 113 ± 20 | 433 ± 35 | 865 ± 99 |

4.3 Antitumor Efficacy Evaluation Indicators

Table 32 shows the evaluation indicators for the antitumor efficacy of agents such as HSA-SN-38 and CPT-11 in the HCT116 xenograft model.

TABLE 32

Analysis on Efficacy in Each Treatment Group in HCT116 Human Colon Cancer Model

| Agent | Nª | Tumor Volume (mm³) D 15 | Tumor Volume (mm³) D 43 | RTV (D 43) | Tumor Weight (mg) (D 43) | T/C (%) RTV | T/C (%) TW | p Value TV | p Value TW |
|---|---|---|---|---|---|---|---|---|---|
| Blank | 7/7 | 117 ± 13 | 1487 ± 193 | 12.58 ± 1.05 | 1441 ± 216 | 100 | 100 | 1.000 | 1.000 |
| CPT-11 60 mg/kg | 7/7 | 117 ± 15 | 477 ± 103 | 4.42 ± 1.05 | 370 ± 87 | 35 | 26 | 0.019 | 0.026 |
| CPT-11 80 mg/kg | 7/7 | 119 ± 15 | 231 ± 44 | 1.95 ± 0.31 | 173 ± 34 | 16 | 12 | 0.007 | 0.013 |
| A01S 450 mg/kg | 7/7 | 117 ± 14 | 1176 ± 77 | 11.22 ± 1.87 | 982 ± 78 | 89 | 68 | 0.895 | 0.640 |
| HSA-SN-38 30 mg/kg | 7/7 | 123 ± 18 | 113 ± 20 | 0.92 ± 0.13 | 86 ± 18 | 7 | 6 | 0.005 | 0.010 |
| HSA-SN-38 10 mg/kg | 7/7 | 124 ± 20 | 433 ± 35 | 3.75 ± 0.36 | 342 ± 42 | 30 | 24 | 0.018 | 0.026 |
| HSA-SN-38 3.3 mg/kg | 7/7 | 117 ± 12 | 865 ± 99 | 7.65 ± 0.96 | 778 ± 100 | 61 | 54 | 0.227 | 0.262 |

Notes:
ªrepresenting the number of animals before the administration/the number of animals at the end of the experiment ($p=0.018$). The analysis result of the tumor weight was substantially consistent with that of the tumor volume.

During the experiment, no animal died in each treatment group. However, the body weight of the animals of different groups including the vehicle group decreased to different extents. A reduction in body weight of the animals at the end of the experiment compared to the body weight before administration was 1.83% in the vehicle group, 5.41% in the A01S group, 16.00% and 14.41% in the high-dosed and low-dosed (80 mg/kg and 60 mg/kg) CPT-11 groups, respectively, and 11.84%, 13.85%, and 12.57% in the groups of three doses of HSA-SN-38 (30 mg/kg, 10 mg/kg, and 3.3 mg/kg), respectively. Given that the body weight of the animals in the vehicle group and the A01S group decreased to different extents in the experiment and no obvious body weight reduction of the animals in the HSA-SN-38 treatment groups was observated in the pharmacological experiments in other models, it was considered that the body weight reduction of the animals in each HSA-SN-38 treatment group in the experiment may be related to the cachexia feature of the HCT116 model.

To sum up, HSA-SN-38 (at doses of 30 mg/kg and 10 mg/kg) had a significant effect in inhibiting tumor growth in the human colon cancer model and was superior to the positive control CPT-11, and had good tolerance, and caused no animal death and no other toxic reaction observed during administration in the experiment.

5. Conclusion and Discussion

It was observed in the experiment that the high dose of HSA-SN-38 (30 mg/kg) had a significant tumor inhibition effect and was superior to CPT-11. At the end of the experiment (43 days (D43) after the inoculation of the tumor), after 4 doses, the high-dosed HSA-SN-38 group had the tumor volume of 113 mm³, the RTV of 0.92, and the T/C value of 7%, and was significantly different from the vehicle group ($p=0.005$). The intermediate dose of HSA-SN-38 (10 mg/kg) had equivalent antitumor activity to the low-dosed (60 mg/kg) CPT-11 group, had the tumor volume of 433 mm³, the RTV of 3.75, the T/C value of 30%, and was significantly different from the vehicle control group Example 26: In Vivo Pharmacodynamic Study in SKOV-3 Human Ovarian Cancer Model Objective: the antitumor activity of different doses of HSA-SN-38 of Example 19 (administered after reconstituted in a vehicle) in a subcutaneous xenograft model of human ovarian cancer cell line SKOV-3 (ATCC HTB 77) in NU/NU nude mice were verified, and compared with that of the commercially available irinotecan hydrochloride (CPT-11) for injection.

1. Experiment Design

TABLE 33

Experiment Design for Antitumor Effects of Test Agents in SKOV-3 Human Ovarian Cancer Model

| Group | Treatment | Number of Animals | Dose (mg/kg) | Administration Route | Dose Volume (mL/kg) | Dosage Regimen |
|---|---|---|---|---|---|---|
| 1 | Vehicle (Blank) | 8 | — | iv | 10 | QW × 4 |
| 2 | CPT-11 | 8 | 60 | iv | 10 | QW × 4 |
| 3 | CPT-11 | 8 | 80 | iv | 10 | QW × 4 |
| 4 | A01S | 8 | 450 | iv | 10 | QW × 4 |
| 5 | HSA-SN-38 | 8 | 30 | iv | 10 | QW × 4 |
| 6 | HSA-SN-38 | 8 | 10 | iv | 10 | QW × 4 |
| 7 | HSA-SN-38 | 8 | 3.3 | iv | 10 | QW × 4 |

2. Experimental Method

SKOV-3 tumor masses were subcutaneously inoculated to 80 BALB/c nude mice. 56 tumor-bearing mice were selected on day 14 after the inoculation, and averagely divided into 7 groups, with 8 mice in each group. By tail intravenous injection, the mice were administered once a week, for a total of 4 weeks. The therapeutic effect was evaluated based on relative tumor inhibition rate (TGI), and the safety was evaluated based on the body weight change and death of the animals.

3. Statistical Analysis

The average values of the tumor of different groups were compared using one-way ANOVA in the experiment. Analysis of homogeneity of variance showed a significant difference in the F value, and multiple comparison was performed using Dunnet's T3 (heterogeneous variance) method after the ANOVA analysis. Analysis on all data was performed using SPSS 17.0. $p<0.05$ was considered to indicate a significant difference.

Figure 15:
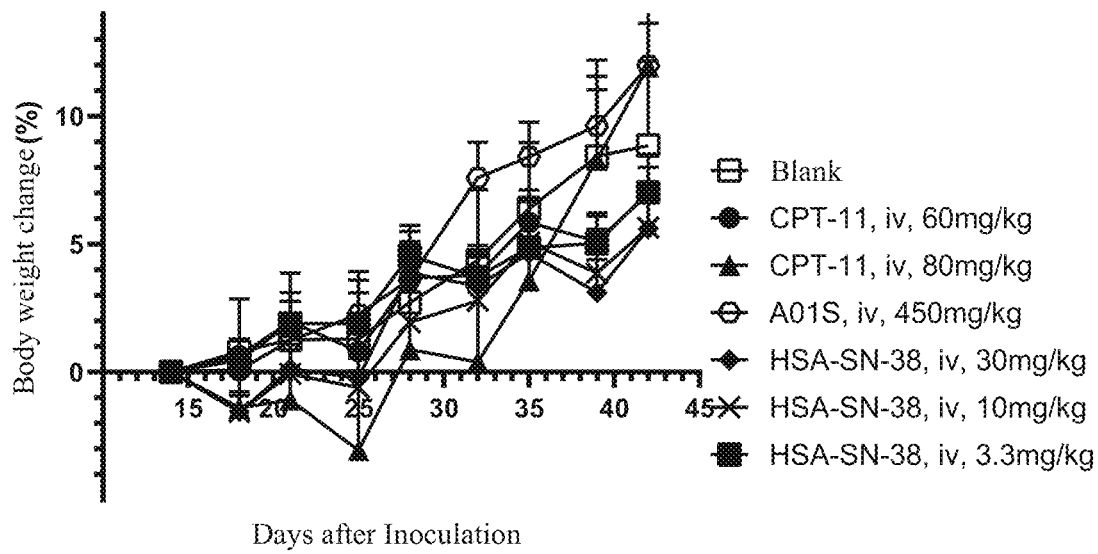
FIG. 15 shows body weight changes of test animals in Example 26.

4. Experimental Results 4.1 Body Weight Change: as shown in FIG. 15.

4.2 Tumor Volume Change

Figure 16:
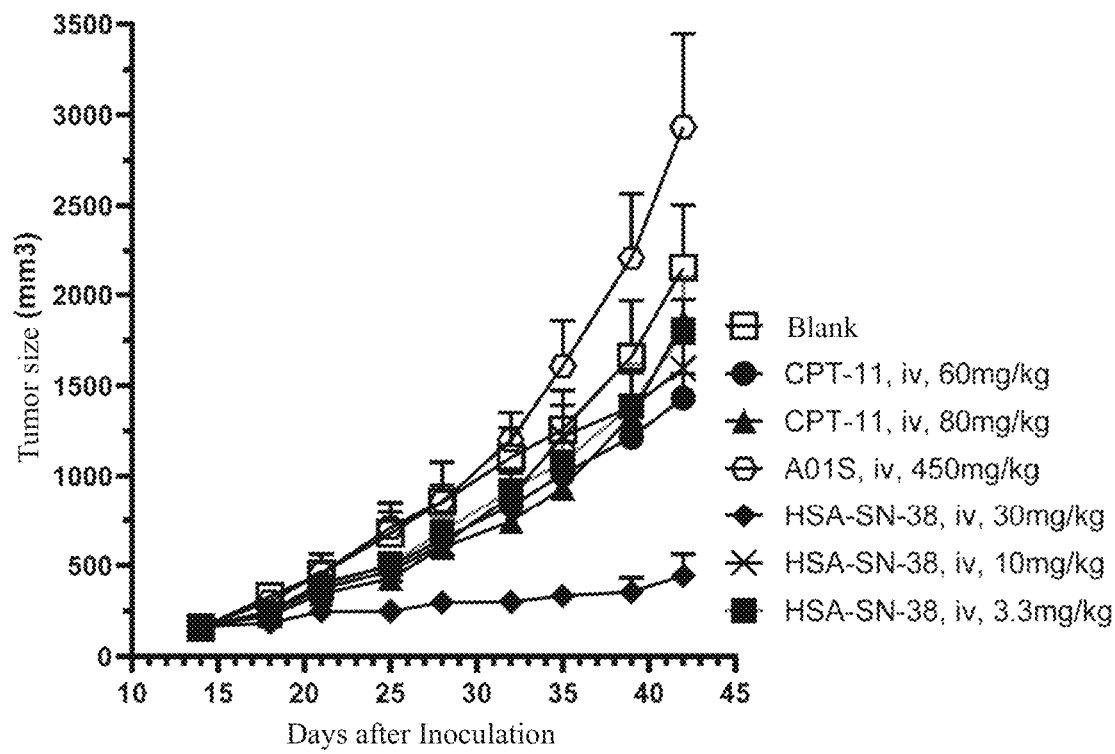
FIG. 16 shows tumor volume changes of test animals in Example 26.

The tumor volume change of different groups is as shown in Table 34 and FIG. 16.

TABLE 34

Tumor Volume of Animals of Different Groups at Different Time points

| Time (D) | Tumor Volume (mm³, Mean ± SEM) | | | | | | |
|---|---|---|---|---|---|---|---|
| | Blank | CPT-11 60 mg/kg | CPT-11 80 mg/kg | A01S 450 mg/kg | HSA-SN-38 30 mg/kg | HSA-SN-38 10 mg/kg | HSA-SN-38 3.3 mg/kg |
| 14 | 160 ± 23 | 161 ± 16 | 162 ± 17 | 163 ± 17 | 163 ± 17 | 162 ± 16 | 162 ± 16 |
| 18 | 313 ± 48 | 246 ± 30 | 224 ± 21 | 300 ± 39 | 186 ± 23 | 250 ± 31 | 235 ± 17 |
| 21 | 450 ± 83 | 405 ± 44 | 343 ± 33 | 458 ± 58 | 248 ± 32 | 372 ± 50 | 375 ± 31 |
| 25 | 687 ± 135 | 497 ± 51 | 429 ± 65 | 708 ± 89 | 249 ± 39 | 470 ± 60 | 511 ± 62 |
| 28 | 866 ± 152 | 642 ± 68 | 598 ± 62 | 857 ± 91 | 296 ± 46 | 615 ± 74 | 684 ± 83 |
| 32 | 1103 ± 163 | 834 ± 90 | 743 ± 133 | 1199 ± 149 | 299 ± 54 | 883 ± 134 | 919 ± 124 |
| 35 | 1256 ± 215 | 1010 ± 96 | 933 ± 149 | 1607 ± 249 | 334 ± 63 | 1218 ± 171 | 1078 ± 153 |
| 39 | 1658 ± 309 | 1214 ± 119 | 1332 ± 85 | 2206 ± 360 | 355 ± 78 | 1382 ± 189 | 1387 ± 231 |
| 42 | 2151 ± 351 | 1430 ± 136 | 1854 ± 120 | 2933 ± 513 | 445 ± 117 | 1596 ± 269 | 1792 ± 307 |

4.3 Antitumor Efficacy Evaluation Indicators

Table 35 showed the evaluation indicators for the antitumor efficacy of HSA-SN-38 and CPT-11 in the SKOV-3 xenograft model.

11.94%. The body weight increase of the animals in the vehicle and A01S control groups were the most obvious, which, at the end of the experiment, was 8.86% and 11.99% as compared with that before administration, respectively.

TABLE 35

Analysis on Efficacy in Each Treatment Group in SKOV-3 Human Ovarian Cancer Model

| Drug | $N^a$ | Tumor Volume ($mm^3$) D 14 | Tumor Volume ($mm^3$) D 42 | RTV (D 42) | Tumor Weight (mg) (D 42) | T/C (%) RTV | T/C (%) TW | p Value TV | p Value TW |
|---|---|---|---|---|---|---|---|---|---|
| Blank | 8/8 | 160 ± 15 | 2151 ± 351 | 14.44 ± 2.33 | 1747 ± 327 | 100 | 100 | 1.000 | 1.000 |
| CPT-11 60 mg/kg | 8/8 | 161 ± 16 | 1430 ± 136 | 9.20 ± 0.79 | 1179 ± 150 | 64 | 67 | 0.691 | 0.870 |
| CPT-11 80 mg/kg | 8/2 | 162 ± 17 | 1854 ± 120 | 11.44 ± 0.21 | 1664 ± 258 | 79 | 95 | 1.000 | 1.000 |
| A01S 450 mg/kg | 8/8 | 163 ± 17 | 2933 ± 513 | 18.75 ± 3.69 | 2611 ± 477 | 130 | 149 | 0.975 | 0.912 |
| HSA-SN-38 30 mg/kg | 8/8 | 163 ± 17 | 445 ± 117 | 2.65 ± 0.60 | 285 ± 96 | 18 | 16 | 0.023 | 0.037 |
| HSA-SN-38 10 mg/kg | 8/8 | 162 ± 16 | 1596 ± 269 | 9.85 ± 1.36 | 1336 ± 238 | 68 | 76 | 0.977 | 0.997 |
| HSA-SN-38 3.3 mg/kg | 8/8 | 162 ± 16 | 1792 ± 307 | 11.13 ± 1.90 | 1532 ± 290 | 77 | 88 | 1.000 | 1.000 |

The high dose of HSA-SN-38 (30 mg/kg) had a significant tumor inhibition effect and was superior to the low dose of CPT-11 (60 mg/kg). At the end of the experiment (on day 42 (D42) after the inoculation of the tumor), after 4 doses, the high-dosed HSA-SN-38 group had the tumor volume of 445 $mm^3$, the RTV of 2.65, and the T/C value of 18%, and was significantly different from the vehicle group (p=0.023). The low-dosed (60 mg/kg) CPT-11 group was not significantly different from the vehicle group (p=0.691). The intermediate-dosed and low-dosed HSA-SN-38 groups were not significantly different from the vehicle group (the p values were 0.977 and 1.000, respectively). The analysis result of the tumor weight was substantially consistent with that of the tumor volume.

During the experiment, 6 animals died in the high-dosed (80 mg/kg) CPT-11 treatment group and no animal died in other groups. At the end of the experiment, the body weight of the animals increased to different extents. The body weight of the animals in the groups of the high, intermediate, and low doses of HSA-SN-38 increased by 5.60%, 5.65%, and 7.03%, respectively. The body weight of the animals in the low-dosed CPT-11 group increased by 6.97% as compared with that before administration, and the body weight of two living animals in the high-dosed group increased by Conclusion:

HSA-SN-38 at a dose of 30 mg/kg had a significant effect in inhibiting tumor growth in the SKOV-3 human ovarian cancer model and was superior to CPT-11, and had good tolerance, caused no animal death and also no other toxic reaction observed during the experiment.

Example 27: In Vivo Pharmacodynamic Study in SW620 Human Colon Cancer Model

Objective: antitumor activity of different doses of rHA-SN-38 prepared in Example 4 in a subcutaneous xenograft model of human colon cancer cell line SW620 (ATCC: CCL-227) in BALB/c nude mice were verified, and compared with that of the commercially available irinotecan hydrochloride (CPT-11) for injection.

1. Experiment Design

TABLE 36

Experiment Design for Antitumor Effects of Test Agents in SW620 Human Colon Cancer Model

| Group | Treatment | Number of Animals | Dose (mg/kg) | Administration Route | Dose Volume (mL/kg) | Dosage Regimen |
|---|---|---|---|---|---|---|
| 1 | Vehicle (Blank) | 7 | — | iv | 10 | QW × 4 |
| 2 | CPT-11 | 7 | 60 | iv | 10 | QW × 4 |
| 3 | CPT-11 | 7 | 80 | iv | 10 | QW × 4 |
| 4 | A01S | 7 | 420 | iv | 10 | QW × 4 |
| 5 | HSA-SN-38 | 7 | 30 | iv | 10 | QW × 4 |
| 6 | HSA-SN-38 | 7 | 10 | iv | 10 | QW × 4 |
| 7 | HSA-SN-38 | 7 | 3.3 | iv | 10 | QW × 4 |

2. Experimental Method

SW620 tumor masses were subcutaneously inoculated to 75 BALB/c nude mice. 49 tumor-bearing mice were selected on day 13 (D13) after the inoculation, and averagely divided into 7 groups, with 7 mice in each group. By tail intravenous injection, the mice were administered once a week, for a total of 4 weeks. The therapeutic effect was evaluated based on relative tumor inhibition rate (TGI), and the safety was evaluated based on the body weight change and death of the animals.

3. Statistical Analysis

The average values of the tumor of different groups were compared using one-way ANOVA in the experiment. Analysis of homogeneity of variance showed a significant difference in the F value, and multiple comparison was performed using Dunnet's T3 (heterogeneous variance) method after the ANOVA analysis. Analysis on all data was performed using SPSS 17.0. $p<0.05$ was considered to indicate a significant difference.

Figure 17:
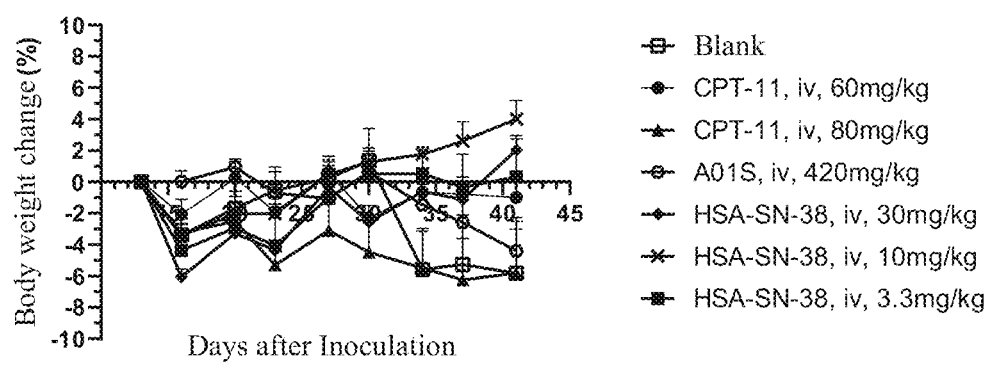
FIG. 17 shows body weight changes of test animals in Example 27.

4. Experimental Results 4.1 Body Weight Change: as shown in FIG. 17.

4.2 Tumor Volume Change

Figure 18:
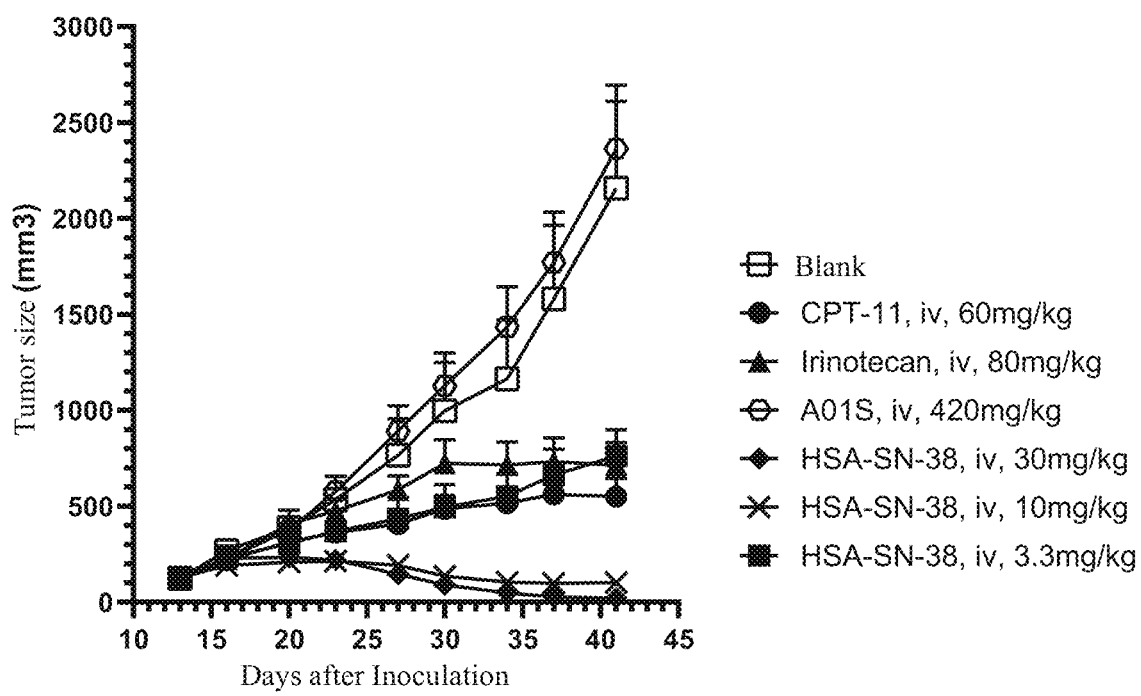
FIG. 18 shows tumor volume changes of test animals in Example 27.

The tumor volume change of different groups is as shown in Table 37 and FIG. 18.

The high-dosed and low-dosed CPT-11 groups (80 mg/kg and 60 mg/kg) had similar efficacy and no obvious dose-effect relationship, and were not significantly different from the vehicle group (p values were 0.202 and 0.133, respectively). The tumor volume of the low-dosed (3.3 mg/kg) rHA-SN-38 group was not significantly different from that of the vehicle group on D41 (p=0.231). The analysis result of the tumor weight was substantially consistent with that of the tumor volume.

No animal died in each group and there was no other abnormal toxic reaction observed. At the end of the experiment, the body weight of the animals of the high-dosed and intermediate-dosed rHA-SN-38 groups increased by 2.03% and 4.01% as compared with that before administration,

TABLE 37

Tumor Volume of Animals of Different Groups at Different Time points

| Time (D) | Tumor Volume (mm³, Mean ± SEM) | | | | | | |
|---|---|---|---|---|---|---|---|
| | Blank | CPT-11 60 mg/kg | CPT-11 80 mg/kg | A01S 420 mg/kg | rHA-SN-38 30 mg/kg | rHA-SN-38 10 mg/kg | rHA-SN-38 3.3 mg/kg |
| 13 | 125 ± 14 | 126 ± 14 | 129 ± 16 | 130 ± 17 | 129 ± 17 | 128 ± 17 | 124 ± 13 |
| 16 | 268 ± 54 | 219 ± 33 | 226 ± 30 | 227 ± 34 | 229 ± 28 | 192 ± 32 | 232 ± 62 |
| 20 | 388 ± 92 | 315 ± 46 | 408 ± 50 | 377 ± 49 | 233 ± 27 | 209 ± 35 | 307 ± 94 |
| 23 | 535 ± 122 | 362 ± 48 | 476 ± 63 | 578 ± 78 | 221 ± 24 | 214 ± 34 | 370 ± 104 |
| 27 | 766 ± 191 | 408 ± 54 | 586 ± 73 | 892 ± 132 | 145 ± 11 | 193 ± 32 | 435 ± 110 |
| 30 | 998 ± 252 | 486 ± 71 | 724 ± 123 | 1129 ± 170 | 90 ± 10 | 136 ± 16 | 494 ± 120 |
| 34 | 1164 ± 307 | 516 ± 73 | 716 ± 119 | 1434 ± 210 | 49 ± 11 | 105 ± 12 | 552 ± 118 |
| 37 | 1580 ± 384 | 563 ± 91 | 732 ± 125 | 1772 ± 262 | 28 ± 4 | 99 ± 10 | 663 ± 136 |
| 41 | 2158 ± 452 | 551 ± 94 | 714 ± 117 | 2364 ± 331 | 21 ± 2 | 101 ± 10 | 762 ± 138 |

4.3 Antitumor Efficacy Evaluation Indicators

Table 38 shows the evaluation indicators for the antitumor efficacy of rHA-SN-38 and CPT-11 in the SW620 xenograft model.

respectively. The body weight of the animals of other groups reduced to different extents at the end of the experiment as compared with that before administration: the reduction was 5.810% and 0.99% in the high-dosed and low-dosed CPT-11

TABLE 38

Analysis on Efficacy of Each Treatment Group in SW620 Human Colon Cancer Model

| Drug | N[a] | Tumor Volume (mm³) D 13 | Tumor Volume (mm³) D 41 | RTV (D 41) | Tumor Weight (mg) (D 41) | T/C (%) RTV | T/C (%) TW | p Value TV | p Value TW |
|---|---|---|---|---|---|---|---|---|---|
| Blank | 7/7 | 125 ± 14 | 2158 ± 452 | 16.43 ± 1.94 | 1754 ± 354 | 100 | 100 | 1.000 | 1.000 |
| CPT-11 60 mg/kg | 7/7 | 126 ± 14 | 551 ± 94 | 4.69 ± 1.12 | 465 ± 91 | 28 | 27 | 0.133 | 0.121 |
| CPT-11 80 mg/kg | 7/7 | 129 ± 16 | 714 ± 117 | 5.95 ± 1.22 | 495 ± 91 | 36 | 28 | 0.202 | 0.132 |
| A01S 420 mg/kg | 7/7 | 130 ± 17 | 2364 ± 331 | 18.75 ± 2.38 | 2089 ± 304 | 114 | 119 | 1.000 | 1.000 |
| HSA-SN-38 30 mg/kg | 7/7 | 129 ± 17 | 21 ± 2 | 0.17 ± 0.01 | 12 ± 3 | 1 | 1 | 0.040 | 0.033 |
| HSA-SN-38 10 mg/kg | 7/7 | 128 ± 17 | 101 ± 10 | 0.81 ± 0.06 | 74 ± 11 | 5 | 4 | 0.047 | 0.039 |
| HSA-SN-38 3.3 mg/kg | 7/7 | 124 ± 13 | 762 ± 138 | 6.08 ± 0.83 | 748 ± 141 | 37 | 43 | 0.231 | 0.321 |

Notes:
[a]representing the number of animals before administration/the number of animals at the end of the experiment The high and intermediate doses of HSA-SN-38 (30 mg/kg and 10 mg/kg) had significant tumor inhibition effects and were superior to CPT-11. At the end of the experiment (on day 41 (D41) after the inoculation of the tumor), after 4 doses, the high-dosed and intermediate-dosed rHA-SN-38 groups had the tumor volume of 21 mm³ and 101 mm³, the RTV of 0.17 and 0.81, and the T/C values of 1% and 5%, respectively, and were significantly different from the vehicle group (p values were 0.040 and 0.047, respectively).

groups, respectively, 0.33% in the low-dose rHA-SN-38 group, and 5.83% and 4.39% in the vehicle and A01S control groups, respectively.

To sum up, rHA-SN-38 at doses of 30 mg/kg and 10 mg/kg had the effect of significantly inhibiting tumor growth in the SW620 human colon cancer model and was superior to CPT-11 at doses of 80 mg/kg and 60 mg/kg. Moreover, the body weight of the animals of the two rHA-SN-38 treatment groups increased more obviously, and the body weight of the animals of the two CPT-11 treatment groups decreased or only increased slightly. On the whole, rHA-SN-38 had obviously stronger antitumor activity than CPT-11 and had good tolerance, caused no animal death and also no other toxic reaction observed during the experiment.

Example 28: In Vivo Pharmacodynamic Study on Hep3B Human Liver Cancer Model

Objective: the antitumor activity of rHA-SN-38 prepared in Example 5 in a subcutaneous xenograft model of human liver cancer cell line Hep3B (ATCC-8064) in BALB/c nude mice was verified, and compared with that of the commercially available irinotecan hydrochloride (CPT-11) for injection.

1. Experiment Design

TABLE 39

Experiment Design for Antitumor Effects of Test Agents in Hep3B Human Liver Cancer Model

| Group | Treatment | Number of Animals | Dose (mg/kg) | Administration Route | Dose Volume (mL/kg) | Dosage Regimen |
|---|---|---|---|---|---|---|
| 1 | Blank | 7 | — | iv | 10 | QW × 4 |
| 2 | CPT-11 | 7 | 60 | iv | 10 | QW × 4 |
| 3 | CPT-11 | 7 | 80 | iv | 10 | QW × 4 |
| 4 | A01S | 7 | 420 | iv | 10 | QW × 4 |
| 5 | HSA-SN-38 | 7 | 30 | iv | 10 | QW × 4 |
| 6 | HSA-SN-38 | 7 | 10 | iv | 10 | QW × 4 |
| 7 | HSA-SN-38 | 7 | 3.3 | iv | 10 | QW × 4 |

2. Experimental Method

Hep3B tumor masses were subcutaneously inoculated to 75 BALB/c nude mice. 49 tumor-bearing mice were selected on day 13 (D13) after the inoculation, and averagely divided into 7 groups, with 7 mice in each group. By tail intravenous injection, the mice were administered once a week, for a total of 4 weeks. The therapeutic effect was evaluated based on relative tumor inhibition rate (TGI), and the safety was evaluated based on the body weight change and death of the animals.

3. Statistical Analysis

The average values of the tumor of different groups were compared using one-way ANOVA in the experiment. Analysis of homogeneity of variance showed a significant difference in the F value, and multiple comparison was performed using Dunnet's T3 (heterogeneous variance) method after the ANOVA analysis. Analysis on all data was performed using SPSS 17.0. $p<0.05$ was considered to indicate a significant difference.

Figure 19:
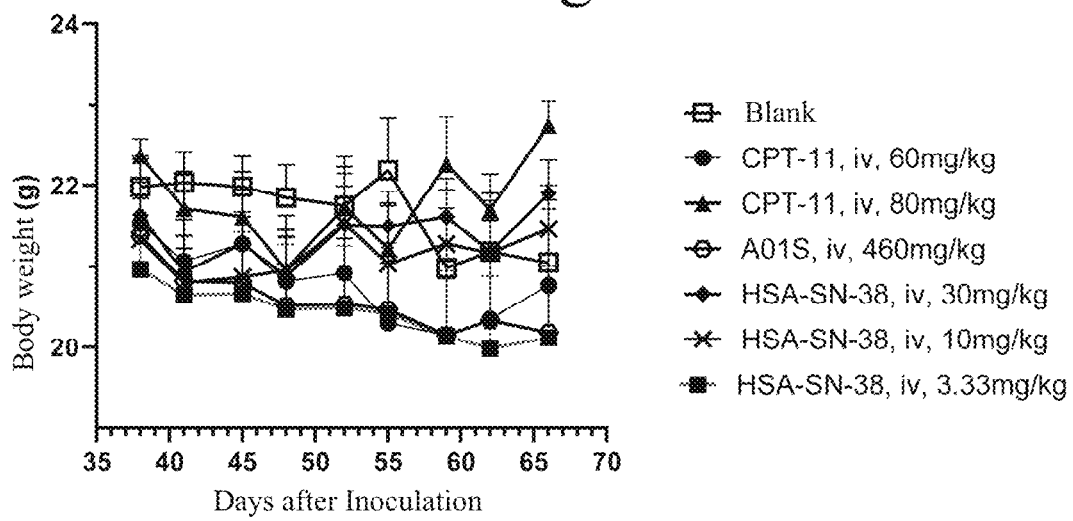
FIG. 19 shows body weight changes of test animals in Example 28.
Figure 20:
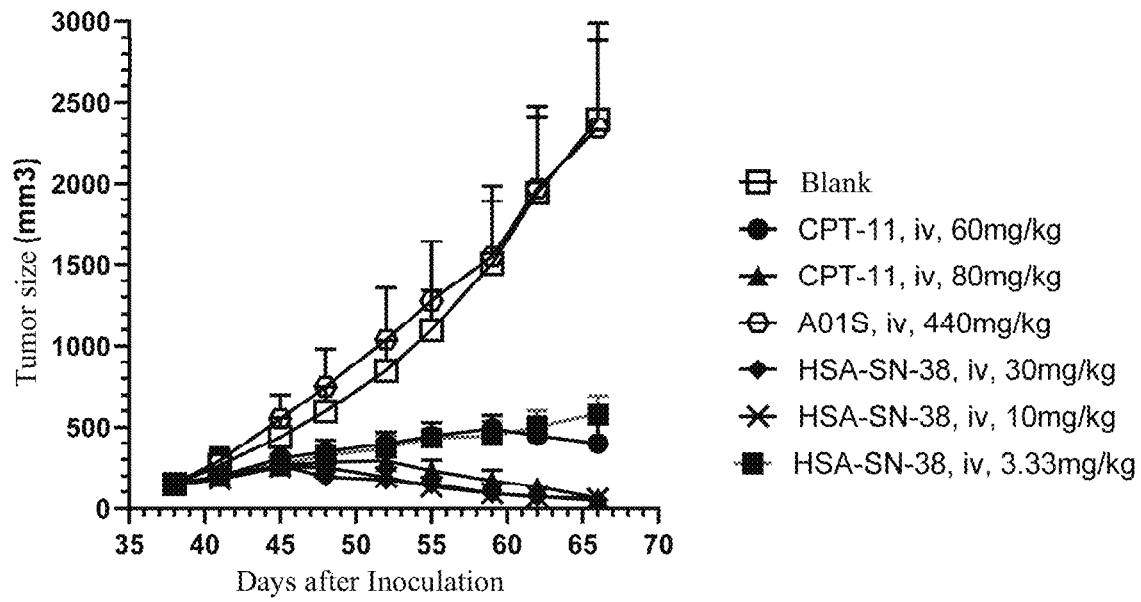
FIG. 20 shows tumor volume changes of test animals in Example 28.

4. Experimental Results
4.1 Body Weight Change: as shown in FIG. 19.
4.2 Tumor Volume Change: as shown in FIG. 20.

Conclusion

The test product rHA-SN-38 at doses of 30 mg/kg and 10 mg/kg had the effect of significantly inhibiting tumor growth in the Hep3B human liver cancer model which was similar to the antitumor level of CPT-11 at a dose of 80 mg/kg. CPT-11 at a dose of 60 mg/kg had antitumor activity which was similar to the tumor inhibition effect of HSA-SN-38 at a dose of 3.33 mg/mL. rHA-SN-38 had good tolerance, without animal death or other toxic reaction observed during the experiment.

Example 29: Influence of Addition of Different Surfactants on SN-38 Formulation Preparation Process:

1) A mixed solvent of EtOH/CHCl$_3$ in a volume ratio of 3/7 was prepared;
2) 300 mg of SN-38, 300 mg of cholesterol, and a surfactant in an amount as shown in the following Table 40 were taken, added with 30 mL of the mixed solvent in step 1), and completely dissolved under heating to obtain a drug solution;
3) An aqueous solution of HSA with a total volume of 370 mL was prepared with deionized water as an aqueous phase such that the total content of HSA in the aqueous phase was 3 g;
4) Shearing dispersion: the drug solution in step 2) was mixed with the aqueous phase in step 3), and shearing dispersion was performed for 10 min to obtain a crude emulsion;
5) The crude emulsion was transferred to a high pressure homogenizer and homogenized under a pressure of 1300-1500 bar for 3-8 times;
6) The homogenized product was transferred to a flask;
7) Rotary evaporation was performed at 40° C.-45° C. for 4-6 min to remove chloroform in the system;
8) EtOH in the system was removed through liquid exchange by a tangential flow ultra-filtration (TFF) system (Millipore);
9) Filtration was performed through a 0.2 µm PES syringe filter membrane.
10) The obtained product was stored in refrigerator at 4° C.

During preparation, the particle size of the sample was detected separately after the shearing dispersion, after the high pressure homogenization, and before and after filtration.

TABLE 40

Parameters of Compositions with Different Surfactants

| Surfactant and Amount (mg) | | Particle Size After Dispersion/PDI (nm/—) | Particle Size After High Pressure Homogenization/PDI (nm/—) | Particle Size Before Filtration/PDI (nm/—) | Particle Size After Filtration/PDI (nm/—) |
|---|---|---|---|---|---|
| Tween 80 | 100 | 278.5 nm/0.406 | 133.7 nm/0.215 (3 times under 1400 bar) | 2466 nm/0.483 | 129.4 nm/0.480 |

TABLE 40-continued

Parameters of Compositions with Different Surfactants

| Surfactant and Amount (mg) | | Particle Size After Dispersion/PDI (nm/—) | Particle Size After High Pressure Homogenization/PDI (nm/—) | Particle Size Before Filtration/PDI (nm/—) | Particle Size After Filtration/PDI (nm/—) |
|---|---|---|---|---|---|
| Span 20 | 18 | 313.2 nm/0.608 | 121.3 nm/0.174 (3 times under 1400 bar) | 134.8 nm/0.201 | 116.2 nm/0.177 |
| Kolliphor HS15 | 100 | 309.4 nm/0.480 | 193.5 nm/0.167 (8 times under 1400 bar) | 6134 nm/0.800 | 28.87 nm/1.000 |
| Poloxamer 188 | 100 | After the addition, there was insoluble particles precipitated out in the organic phase, NA. | | | |
| No surfactant added | — | 419.2 nm/0.781 | 140.5 nm/0.185 (5 times under 1400 bar) | 178.2 nm/0.183 | 153.6 nm/0.080 |

The results indicate that the addition of different amounts of surfactants to the organic phase affected the times of homogenization and the particle size during the preparation process, and Span 20 was superior in reducing the times of homogenization and reducing the particle size of nanoparticles to other surfactants or no addition of a surfactant.

Example 30: Influence of Addition of Span 20 on Filtration Flux of SN-38 Formulation To further study the influence of Span 20 on the preparation process, the particles size and the filtration flux in the steps of preparing the SN-38 formulation with or without adding Span 20 were compared. The preparation process and the addition amount of Span 20 were the same with Example 29. The results are shown in Table 41.

TABLE 41

Influence of Addition of Span 20 or No Span 20 on Particle Size and Filtration Flux

| Span 20 | Particle Size After High Pressure Homogenization/PDI (nm/—) | Particle Size After TFF/PDI (nm/—) | Particle Size After Filtration/PDI (nm/—) |
|---|---|---|---|
| Not added | 139.9 nm/0.222 | 157.6 nm/0.208 | 131.2 nm/0.192 (the filtration flux was 6.5 mL) |
| Added | 132.9 nm/0.264 | 148.9 nm/0.222 | 119.5 nm/0.194 (the filtration flux was 10 mL) |

The results indicate that compared with the formulation prepared without Span 20, the product prepared by the preparation process with adding Span 20 had a smaller particle size and an increased filtration flux through the PES syringe filter.

Moreover, the disintegration experiments of the above two samples were conducted in accordance with the method described in item 9 of the preamble of Examples. Specifically, the sample was diluted with 1×PBS at pH 7.4. The particle size of the sample at different dilution factors was measured to study at what dilution factor disintegration of the nanoparticles will occur precipitate out the SN-38 raw material. A higher dilution factor indicates better stability of the nanoparticles.

Figure 21:
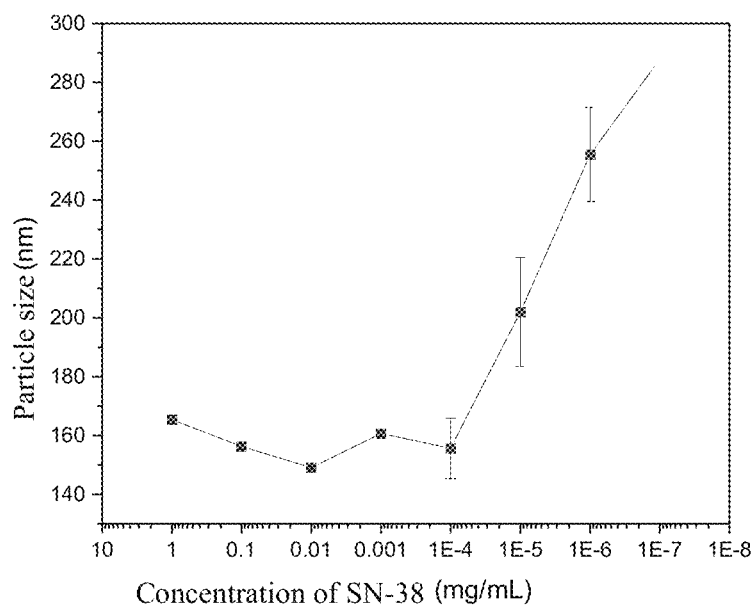
FIG. 21 shows the results of a formulation comprising Span 20 prepared in Example 30 in a disintegration experiment conducted under gradient dilution.
Figure 22:
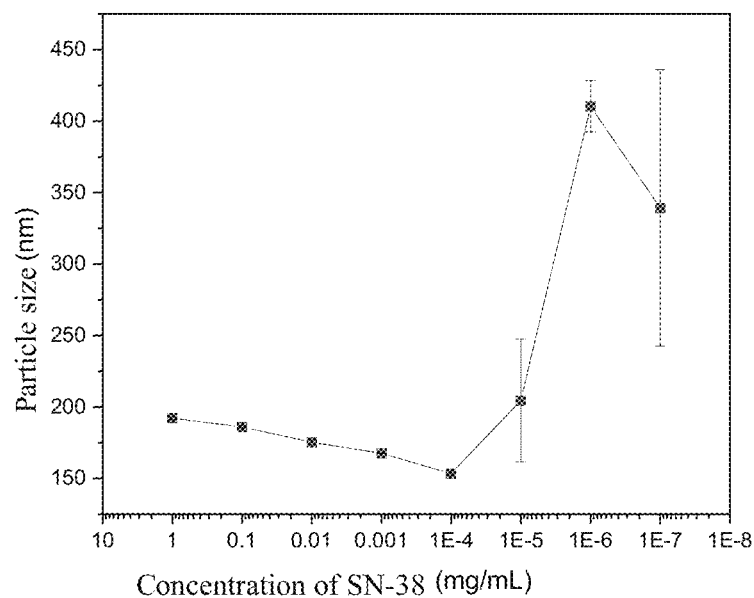
FIG. 22 shows the results of a formulation comprising no Span 20 prepared in Example 30 in a disintegration experiment conducted under gradient dilution.

The results of the disintegration experiment were as shown in FIG. 21 and FIG. 22. The results indicate that whether Span 20 was added or not, when diluted to 0.1 ug/mL, the two samples were still in a stable state; and when continuously diluted to 10 ng/mL, the particle size of the two samples increased obviously and the nanoparticles underwent disintegration. After Span 20 was added, the particle size change after disintegration had a smaller amplitude and was more stable.

Figure 23:
FIG. 23 shows the results of the formulation comprising Span 20 prepared in Example 30 observed by cryogenic transmission electron microscope.
Figure 24:
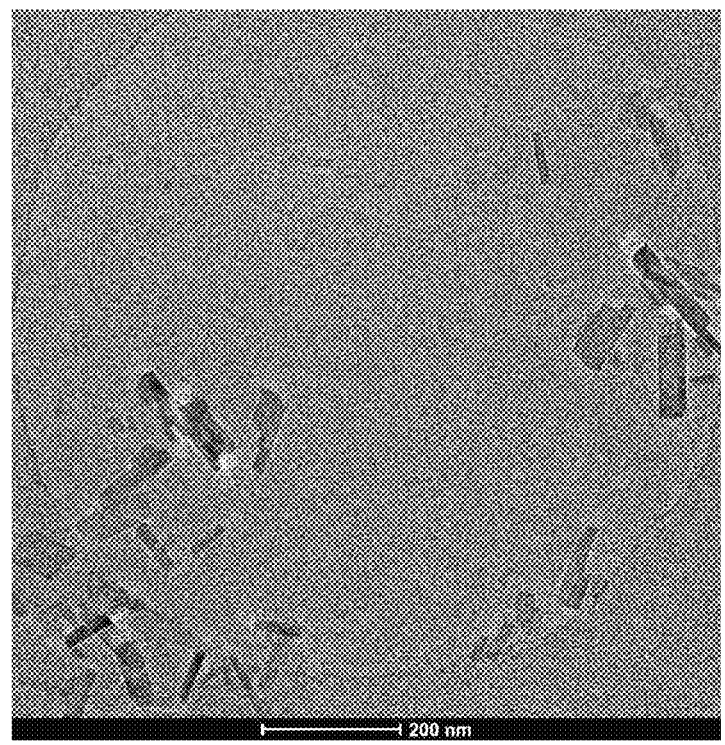
FIG. 24 shows the results of the formulation comprising no Span 20 prepared in Example 30 observed by cryogenic transmission electron microscope.

In addition, in accordance with the method described in item 11 of the preamble of Examples, the morphology of the above two samples was observed using a cryogenic transmission electron microscope, and the observation results of the electron microscope are as shown in FIG. 23 and FIG. 24. From the results, it was found that in the two samples, API had two different states, namely nanocrystals and vesicles, and the sample comprising Span 20 had more vesicles and fewer nanocrystals. Since SN-38 in the form of vesicles was fast-action API after entering the human body, it was indicated that the addition of Span 20 was helpful in enabling the formulation to exert its efficacy in the body as fast as possible, while better maintaining the particle size of the nanoparticles.

Example 31: Influence of Addition of Different Amounts of Span 20 on SN-38 Formulation Preparation Process:

1) An organic solvent system was prepared as shown in the following Table 42;
2) SN-38, cholesterol, and Span 20 were weighed as shown in Table 42, added with 30 mL of the organic solvent in step 1), and dissolved completely to obtain a drug solution;
3) An aqueous solution of HSA with a total volume of 370 mL was prepared with deionized water as an aqueous phase such that the total content of HSA in the aqueous phase was 3 g;
4) Shearing dispersion: the drug solution in step 2) was mixed with the aqueous phase in step 3), and shearing dispersion was performed for 10 min to obtain a crude emulsion;
5) The crude emulsion was transferred to a high pressure homogenizer and homogenized under a pressure of 1300-1500 bar for 3-5 times;
6) The homogenized product was transferred to a flask;
7) Rotary evaporation was performed at 40° C.-45° C. for 4-6 min to remove chloroform in the system;
8) DMSO or EtOH in the system was removed through liquid exchange by TFF;
9) Filtration was performed through a 0.2 μm PES syringe filter membrane, and the parameters such as the particle size, the API filtration recovery, and the loading of drug of the sample were detected before and after filtration;
10) The sample was stored in refrigerator at 4° C.
The results are shown in Table 42.

or strong light for 5 days or 10 days for use as samples to be measured.
2) The contents of the human serum albumin multimer in the SN-38 formulations produced by different prepara-

TABLE 42

Influence of Addition of Different Amounts of Span 20 on SN-38 Formulation Size

| Formulation | Organic Solvent System (v/v) | Formula of the Formulation (mg) | Particle Size Before Passing Through Membrane/ PDI (nm/—) | Particle Size After Passing Through Membrane/ PDI (nm/—) | Loading of drug (%) | API Filtration Recovery (%) |
|---|---|---|---|---|---|---|
| 1 | DMSO/CHCl$_3$ = 1:1 | SN-38 180 mg; Cholesterol 300 mg; Span 20 9 mg | 147.6/0.140 | 129.6/0.130 | 4.140% | 77.37% |
| 2 | DMSO/CHCl$_3$ = 1:1 | SN-38 120 mg; Cholesterol 450 mg; Span 20 9 mg | 156.5/0.139 | 137.0/0.135 | 2.766% | 72.38% |
| 3 | DMSO/CHCl$_3$ = 1:1 | SN-38 180 mg; Cholesterol 450 mg; Span 20 9 mg | 131.2/0.161 | 118.4/0.133 | 4.265% | 81.74% |
| 4 | DMSO/CHCl$_3$ = 1:1 | SN-38 240 mg; Cholesterol 450 mg; Span 20 9 mg | 163.9/0.125 | 142.9/0.103 | 4.358% | 62.36% |
| 5 | DMSO/CHCl$_3$ = 1:1 | SN-38 180 mg; Cholesterol 450 mg; Span 20 18 mg | 137.6/0.152 | 123.3/0.138 | 4.060% | 76.86% |
| 6 | DMSO/CHCl$_3$ = 1:1 | SN-38 180 mg; Cholesterol 600 mg; Span 20 9 mg | 139.0/0.130 | 124.8/0.0062 | 4.164% | 75.04% |
| 7 | DMSO/CHCl$_3$ = 1:1 | SN-38 120 mg; Cholesterol 600 mg; Span 20 18 mg | 117.4/0.164 | 108.1/0.126 | 3.319% | 84.46% |
| 8 | DMSO/CHCl$_3$ = 1:1 | SN-38 240 mg; Cholesterol 600 mg; Span 20 18 mg | 137.8/0.158 | 122.2/0.123 | 5.553% | 79.82% |
| 9 | EtOH/CHCl$_3$ = 3:7 | SN-38 120 mg; Cholesterol 300 mg; Span 20 18 mg | 109.4/0.234 | 98.43/0.211 | 3.173% | 90.49% |
| 10 | EtOH/CHCl$_3$ = 3:7 | SN-38 240 mg; Cholesterol 300 mg; Span 20 18 mg | 125.2/0.228 | 107.5/0.272 | 6.040% | 87.56% |
| 11 | EtOH/CHCl$_3$ = 3:7 | SN-38 300 mg; Cholesterol 300 mg; Span 20 18 mg | 138.8/0.214 | 116.5/0.163 | 7.298% | 81.47% |
| 12 | EtOH/CHCl$_3$ = 3:7 | SN-38 300 mg; Cholesterol 300 mg | 152.3/0.267 | 134.9/0.183 | 4.146% | 75.24% |

The results indicate that for different content ratios of SN-38 and cholesterol, by adding Span 20 in the preparation process, the particle size of the nanoparticles can be reduced, the filtration efficiency and flux can be improved, and the filtration recovery can be increased. Single-factor comparison indicates that Span 20 can increase the loading of drug and the API recovery.

Example 32: Influence of Addition of Span 20 on Stability of SN-38 Formulation

The influence of Span 20 on the production of albumin multimer in the solution was observed by measuring the content of the human serum albumin multimer in the SN-38 formulation.

Experimental Method:
1) Formulations 11 and 12 from Example 31 were filled in vials and lyophilized in vacuum to obtain lyophilized formulations of HSA-SN-38 nanoparticles. After storage for 14 days, they were diluted with deionized water such that the concentrations of SN-38 were the same as the concentrations before lyophilization, and stored under the condition of high temperature, high humidity, tion methods were measured using SEC-HPLC. 5 μl of the prepared sample was taken for detection, and chromatographic conditions were as shown in Table 43.

TABLE 43

Chromatographic Conditions of SEC-HPLC for Measuring Albumin Aggregate in Sample

| | |
|---|---|
| Chromatographic column model | TSKgel G3000Swxl 7.8 × 300 mm, 5 μm Guard SWXL 6.0 * 40 |
| Chromatographic column No. | QCCA-RP-007 |
| Detector wavelength | 228 nm |
| Column temperature | 30° C. |
| Sample tray temperature | 5° C. |
| Flow rate | 0.4 mL/min |
| Mobile phases | A: 0.1 mol/L K$_2$HPO$_4$ B: ACN |

TABLE 43-continued

Chromatographic Conditions of SEC-HPLC for Measuring Albumin Aggregate in Sample

|  | Time (min) | Flow rate (mL/min) |
|---|---|---|
| Running time and flow rate | 0 | 0.4 |
|  | 25 | 0.4 |
|  | 28 | 0.9 |
|  | 55 | 0.9 |
|  | 56 | 0.4 |
|  | 60 | 0.4 |
| Elution mode | Isocratic elution: A(98%) + B(2%) | |
| Sample injection volume | 5 μL | |
| Running time | 30 min | |

The results are shown in the Table 44 below:

TABLE 44

Influence of Addition of Span 20 on Stability of Albumin

| | Detection results | | | | | |
|---|---|---|---|---|---|---|
| | High temperature (40° C.) | | High humidity (75% RH) | | Strong light (5000LX) | |
| Day Sample | 5 d | 10 d | 5 d | 10 d | 5 d | 10 d |
| Formulation 12 0.4% | / | 3.1% | 1.7% | 2.3% | 2.1% | 2.4% |
| Formulation 11 0.5% | 0.4% | 0.5% | 0.5% | 0.4% | 0.4% | 0.4% |

Notes:
the percentage content in the table represents the percentage content of the multimer in the sample. The smaller the value, the less the multimer.

The results indicate that compared with Formulation 12 without addition of Span 20, Formulation 11 added with Span 20 had no obvious change in albumin multimer content, indicating that Span 20 is capable of inhibiting albumin aggregation. Therefore, Span 20 is capable of effectively preventing the aggregation of albumin in the solution and prolonging the shelf life of the drug, and will not have immunogenicity caused by the albumin multimer.

Example 33: Influence of Contents of Albumin on SN-38 Formulations

According to the formulas shown in Table 45, SN-38 formulations were prepared by the method of Example 29 except that no Span 20 was added in Formulation 13 and 6 g and 12 g of HSA were contained in Formulations 15 and 16, respectively. The particle sizes in the steps of preparing the SN-38 formulations were measured, and the API filtration recovery was also measured to investigate the influence of HSA contents on the formulations. The results are shown in Table 46.

TABLE 45

Compositions of Formulations

| Formulation | HSA (g) | SN-38 (mg) | Cholesterol (mg) | Span 20 (mg) |
|---|---|---|---|---|
| 13 | 3 | 300 | 300 | 0 |
| 14 | 3 | 300 | 300 | 18 |
| 15 | 6 | 300 | 300 | 18 |
| 16 | 12 | 300 | 300 | 18 |

TABLE 46

Influence of Contents of Albumin on SN-38 Formulations

| Sample | Particle size After Dispersion/ PDI (nm/—) | Particle size After High Pressure Homogenization/ PDI (nm/—) | Particle size After Evaporation/ PDI (nm/—) | Particle size After TFF/PDI (nm/—) | Particle size After Filtration/ PDI (nm/—) | API Filtration Recovery (%) |
|---|---|---|---|---|---|---|
| 13 | 312.3/0.284 | 228.2/0.277 | 267.3/0.267 | 151.17/0.198 | 134.9/0.183 | 73.24% |
| 14 | 216.4/0.251 | 133.4/0.245 | 138.8/0.214 | 127.8/0.188 | 116.5/0.163 | 83.46% |
| 15 | 298.6/0.198 | 190.7/0.186 | 160.13/0.134 | 136.77/0.175 | 121.9/0.141 | 70.56% |
| 16 | 456.8/0.489 | 242.1/0.213 | 264.5/0.200 | 216.8/0.210 | 173.5/0.147 | 61.39% |

The results indicate that increase in the amount of albumin in the formula will lead to increased particle size of the sample, obviously reduced filtration flux, and reduced API filtration recovery. It is appropriate that the amount ratio of HSA:API is controlled to 20:1 or below. A ratio above this ratio, especially up to 40:1 or more, leads to not only nanoparticles which are excessively large in particle size, unstable, and prone to aggregation to produce immunogenicity, but also difficulty in filtration, low API recovery, and a failure of large-scale production.

Example 34: In Vivo Pharmacodynamic Study in SW620 Human Colon Cancer Model

Objective: the antitumor activity and safety of SN-38 formulations with different amounts of Span 20 and HSA prepared in Example 31 in the subcutaneous xenograft model of human colon cancer cell line SW620 (ATCC: CCL-227) in BALB/c nude mice were verified, and compared with that of the commercially available irinotecan hydrochloride (CPT-11) for injection.

TABLE 47

Experiment Design

| Control/Test Product | Number of Mice | Dose (mg/kg) | Dose Volume (μl/g) | Administration Route | Dosage Regimen |
|---|---|---|---|---|---|
| Blank | 6 | — | 10 | iv | QW × 4 |
| CPT-11 | 6 | 60 | 10 | iv | QW × 4 |
| Formulation 9 | 6 | 10 | 10 | iv | QW × 4 |

TABLE 47-continued

Experiment Design

| Control/Test Product | Number of Mice | Dose (mg/kg) | Dose Volume (μl/g) | Administration Route | Dosage Regimen |
|---|---|---|---|---|---|
| Formulation 10 | 6 | 10 | 10 | iv | QW × 4 |
| Formulation 11 | 6 | 10 | 10 | iv | QW × 4 |
| Formulation 12 | 6 | 10 | 10 | iv | QW × 4 |

Notes:
QW × 4 represents administration once a week, for a total of 4 weeks.

Cell Culture

In vitro monolayer culture of SW620 cells was carried out in 1640 medium added with 10% heat-inactivated fetal bovine serum and agar in 5% $CO_2$ containing air in an incubator at 37° C., and were digested twice a week with 0.25% pancreatin for passage. At the exponential growth phase of cells, cells were harvested, counted, and inoculated.

Tumor Cell Inoculation and Tumor Mass Passage $5.0 \times 10^6$ SW620 tumor cells were suspended in 0.1 mL of PBS and inoculated to the right scapulas of 5 nude mice (P1 generation). After the tumor grew to 500-800 mm³, the tumor-bearing mice were anesthetized with $CO_2$ and euthanized. The tumor masses were obtained and the surrounding necrotic tissues were removed. The tumor masses in a good state were cut into small tumor masses of 20-30 mm³ and inoculated to the right scapulas of a new batch of nude mice (P2 generation). A total of 40 mice were inoculated.

Tumor Mass Inoculation, Grouping and Dosing

The antitumor activity of the test products were evaluated using the tumor tissues of the P2 generation in the experiment. When the average tumor volume reached about 159 mm³ 7 days after the inoculation of the tumor masses, the mice with excessively small or large tumor volumes were screened out, and the remaining 36 mice were randomly grouped by tumor volume, and administration began.

Figure 25:
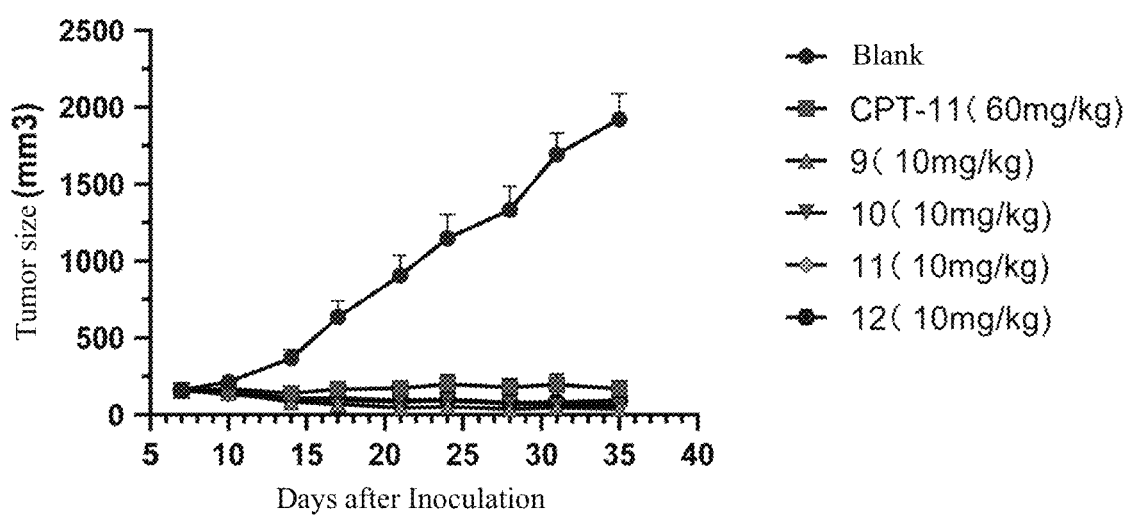
FIG. 25 shows tumor volume changes of test animals in Example 34.
Figure 26:
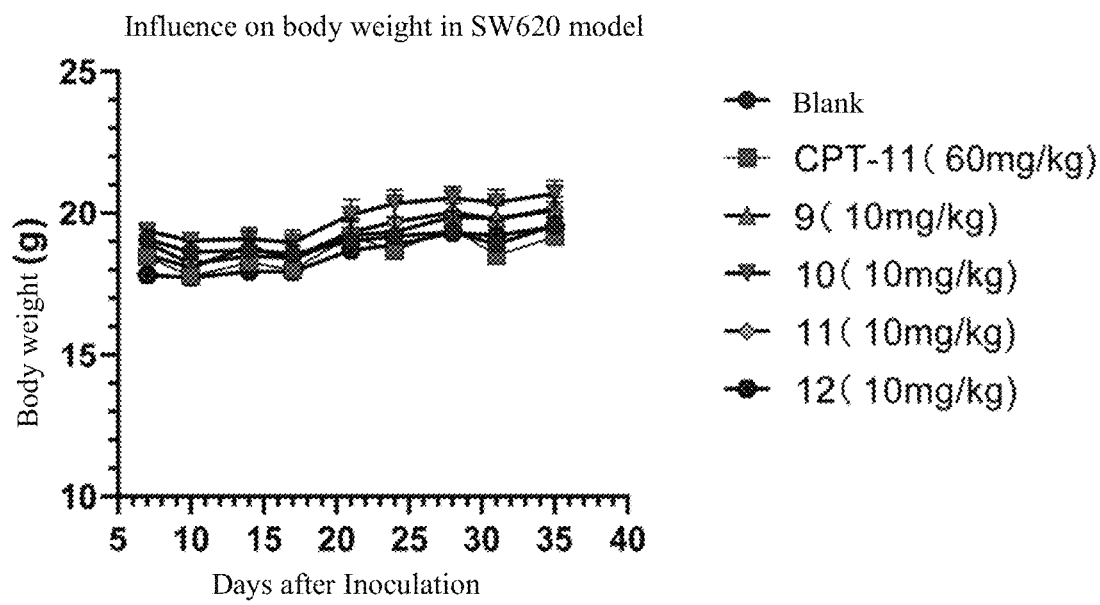
FIG. 26 shows body weight changes of test animals in Example 34.
Figure 27:
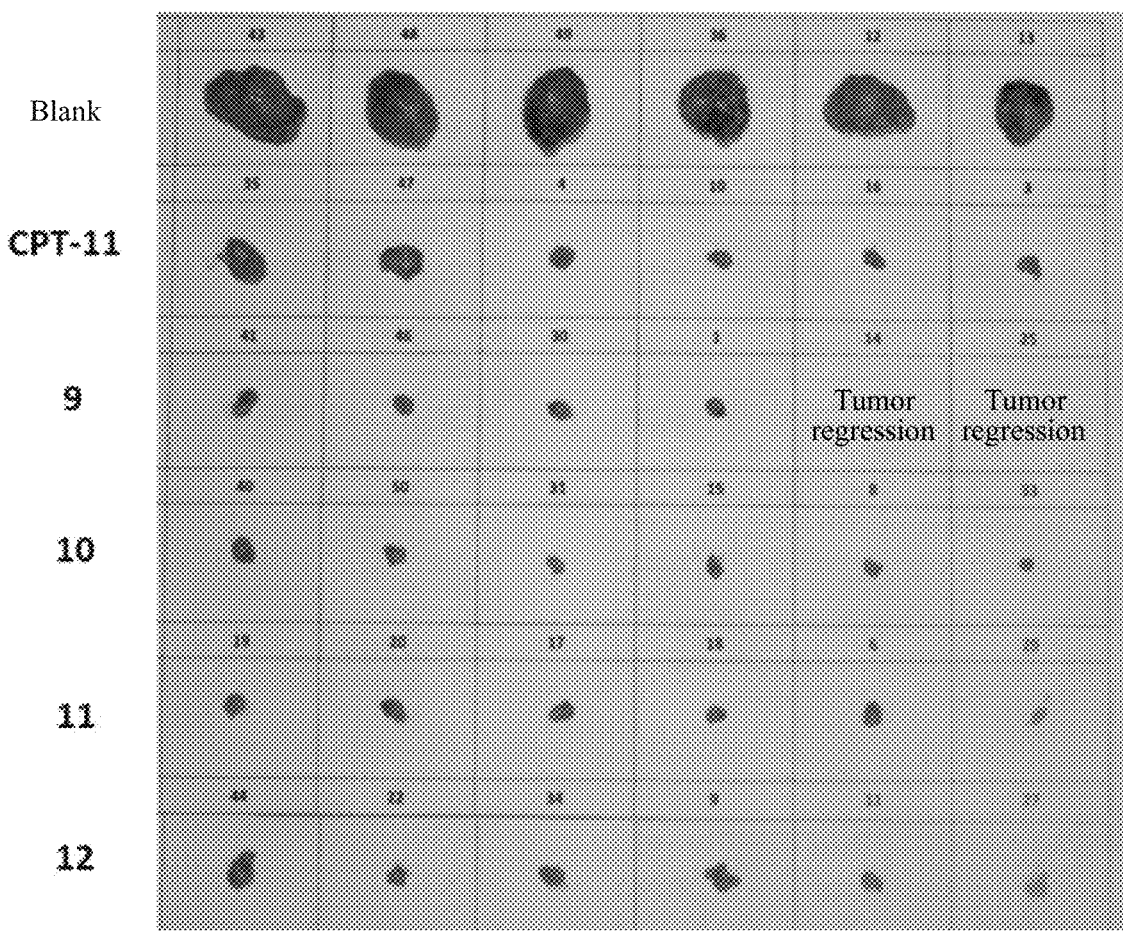
FIG. 27 shows tumor mass sizes of test animals in Example 34.

The results are shown in FIG. 25 to FIG. 27 and Table 48.

Notes: T/C (%) means a percentage of TV or TW of the treatment group (T) relative to the blank control group (C), and the smaller the value thereof, the better the tumor inhibition effect.

The results indicate that the formulations with different amounts of Span 20 and the formulation with no Span 20 had better antitumor activities than CPT-11.

Example 35: Influence of Replacement of EtOH/CHCl₃ Mixed Solvent with EtOH/CH₂Cl₂/CHCl₃ Mixed Solvent on Formulations 1. Preparation Process:
   1) EtOH/CH₂Cl₂/CHCl₃ mixed solvent was prepared according to the volume ratio shown in the Table 49 below;
   2) 300 mg of SN-38, 300 mg of cholesterol, and 18 mg of Span 20 were taken, added with 30 mL of the mixed solvent in step 1), and completely dissolved under heating to obtain a drug solution;
   3) An aqueous solution of HSA with a total volume of 370 mL was prepared with deionized water as an aqueous phase such that the total content of HSA in the aqueous phase was 3 g; Shearing dispersion: the drug solution in step 2) was mixed with the aqueous phase in step 3), and shearing dispersion was performed for 10-15 min to obtain a crude emulsion;
   4) The crude emulsion was transferred to a high pressure homogenizer and homogenized under a pressure of 1300-1500 bar for 5 times, and the homogenized sample was transferred to a flask; 5) Rotary evaporation was performed at 40° C.-45° C. for 4-6 min;
   6) EtOH in the system was removed through liquid exchange by TFF;
   7) Filtration was performed through a 0.2 μm PES syringe filter membrane, and the parameters such as particle size, API filtration recovery, and loading of drug of the sample were detected before and after the filtration;
   8) The sample was stored in refrigerator at 4° C.

TABLE 48

| | | | Body Weight (g, mean ± SEM) | | | Tumor Volume (TV)/Weight (TW) (mean ± SEM) | | | | | | |
|---|---|---|---|---|---|---|---|---|---|---|---|---|
| | | | | | | TV (mm³) | | TW | T/C (%) | | p Value | |
| Drug | n | Dose (mg/kg) | Day 11 | Day 39 | Change (%) | Day 11 | Day 39 | (mg) | TV | TW | TV | TW |
| Blank | 6 | — | 19.1 ± 0.3 | 19.6 ± 0.8 | +2.5 | 158 ± 21 | 1921 ± 168 | 1466 ± 170 | 100 | 100 | 1.000 | 1.000 |
| CPT-11 | 6 | 60 | 18.5 ± 0.6 | 19.2 ± 0.7 | +3.8 | 157 ± 18 | 154 ± 57 | 99 ± 43 | 8 | 7 | 0.001 | 0.005 |
| Formulation 9 | 6 | 10 | 18.5 ± 0.6 | 20.1 ± 0.5 | +8.7 | 163 ± 17 | 38 ± 15 | 20 ± 7 | 2 | 1 | 0.001 | 0.005 |
| Formulation 10 | 6 | 10 | 19.4 ± 0.2 | 20.7 ± 0.4 | +6.9 | 158 ± 17 | 59 ± 12 | 24 ± 5 | 3 | 2 | 0.001 | 0.005 |
| Formulation 11 | 6 | 10 | 19.0 ± 0.6 | 20.2 ± 0.7 | +6.4 | 158 ± 17 | 60 ± 7 | 29 ± 5 | 3 | 2 | 0.001 | 0.005 |
| Formulation 12 | 6 | 10 | 17.8 ± 0.6 | 19.5 ± 0.5 | +9.7 | 158 ± 17 | 91 ± 17 | 39 ± 9 | 5 | 3 | 0.001 | 0.005 |

TABLE 49

Influence of Different Organic Solvent Systems on Encapsulation Result

| Organic Solvent System (v/v) | Particle Size Before Passing Through Membrane/PDI (nm/—) | Particle Size After Passing Through Membrane/PDI (nm/—) | API Filtration Recovery (%) | Loading of drug (%) | $CHCl_3$/API in Liquid After Passing Through Membrane |
|---|---|---|---|---|---|
| EtOH/$CHCl_3$ = 7/13 | 133.4/0.206 | 112.9/0.171 | 85.735% | 7.411% | 7.668 ug/mg API |
| EtOH/$CH_2Cl_2$/$CHCl_3$ = 6/7/7 | 144.6/0.203 | 121.6/0.121 | 80.069% | 6.875% | 3.335 ug/mg API |
| EtOH/$CH_2Cl_2$/$CHCl_3$ = 6/4/10 | 136.1/0.213 | 113.5/0.161 | 84.168% | 7.515% | 4.841 ug/mg API |

2. Results:

After the organic solvent system was adjusted to EtOH/$CH_2Cl_2$/$CHCl_3$=6/7/7, the amount of residual $CHCl_3$ decreased obviously, and meanwhile, the roughly quantified level of residual $CH_2Cl_2$ was also low (2 ug/mg of API). By calculating based on the amount of residual $CHCl_3$ in the liquid after filtration and the daily maximum exposure (600 ug) of $CHCl_3$, the maximum clinical dose was >100 mg/m$^2$. The dose limitation caused by $CHCl_3$ residue was greatly reduced. However, due to lower solubility of SN-38 in $CH_2Cl_2$ and faster crystal precipitation upon dispersion of the organic phase in the aqueous phase, the crude product prepared using the EtOH/$CH_2Cl_2$/$CHCl_3$ mixed solvent had a larger particle size, lower API filtration recovery, and lower loading of drug.

After the amount of $CH_2Cl_2$ was adjusted to reach EtOH/$CH_2Cl_2$/$CHCl_3$=6/4/10, the particle size of the crude product decreased, and the parameters such as API filtration recovery were consistent with those of the product prepared using the EtOH/$CHCl_3$ mixed solvent. However, the level of $CHCl_3$ residue still decreased obviously.

Example 36: Large-Scale Preparation of HSA-SN-38 Products Added with SP20

Preparation Process:
1) 300 mL of a mixed organic solvent was prepared as shown in Table 50 below;
2) 3 g of SN-38, 3 g of cholesterol, and 0.18 g of Span 20 were taken, added with 30 mL of the mixed organic solvent in step 1), and dissolved completely under heating to obtain a drug solution;
3) 150 mL of a 20% HSA solution was taken and diluted with 3550 mL of deionized water to obtain an aqueous phase;
4) Shearing dispersion and homogenization: an inline shearer (Fluke FDHS3/60) was connected in series to a high pressure homogenizer (ATS, AH12-150) in a continuous production mode, and the rotating speed of the inline shearer was set to 8000-10000 rpm. The aqueous phase in step 3) and the organic phase in step 2) were pumped in a certain ratio into the inline shearer, and then the drug solution was fed to the high pressure homogenizer and homogenized under a pressure of 1300-1500 bar for 5 times;
5) Evaporation: chloroform and dichloromethane in the system were removed by evaporation in a falling film evaporator (evaporation tube temperature was 40° C.-45° C.);
6) Residual EtOH in the system was removed through liquid exchange by TFF;
7) Sucrose was added at a concentration of 80 mg/ml;
8) Filtration was performed through a 0.2 μm bag filter, and the parameters such as particle size, API filtration recovery, and loading of drug of the sample were detected before and after filtration;
9) The sample was filled in vials, 15 mL for each vial, and then lyophilized. The residual solvent in the lyophilized sample was detected.

TABLE 50

Influence of 10 Times Scaled-up Preparation Process on Encapsulation Result

| Sample | Organic Solvent System (v/v) | Batch size | Particle Size Before Passing Through Membrane/ PDI (nm/—) | Particle Size After Passing Through Membrane/ PDI (nm/—) | API Filtration Recovery (%) | Loading of drug (%) | $CHCl_3$/API in the Liquid After Passing Through Membrane | Chloroform Residue in Lyophilizled Powder (ppm) |
|---|---|---|---|---|---|---|---|---|
| Formulation 17 | EtOH/$CHCl_3$ = 7/13 | 4 L | 137.3/0.190 | 132.5/0.182 | 85.961% | 7.440% | 6.463 ug/mg API | 55 |
| Formulation 18 | EtOH/$CH_2Cl_2$/ $CHCl_3$ = 6/4/10 | 4 L | 131.4/0.205 | 127.0/0.166 | 86.808% | 7.653% | 4.448 ug/mg API | 33 |

The results show that the chloroform residue level of the product prepared using EtOH/CH$_2$Cl$_2$/CHCl$_3$=6/4/10 as the mixed organic solvent decreased obviously, and the properties of the product prepared in scaled-up production were consistent with those prepared by the small-scale batch.

Example 37: Influence of Addition of Span 20 on Stability of HSA-SN-38 Formulation at Different Time The influence of Span 20 on the stability (multimer, particle size, and the like) of the albumin in the solution was studied by measuring the content of the human serum albumin multimer in the SN-38 formulation.

Experimental Method:
1) Formulation 12 from Example 31 and Formulation 18 from Example 36 were filled in vials and lyophilized in vacuum to obtain lyophilized HSA-SN-38 formulations. Before the start of the stability experiment, the involved samples were each stored in refrigerator (at 2° C.-8° C.) for 0 day, 3 months, and 6 months, and then diluted with deionized water such that the concentrations of SN-38 were the same as the concentrations before lyophilization, and then the moisture, the pH value, the osmotic pressure, the particle size and the particle size distribution, the contents of multimer and cholesterol were detected. The results are as shown in Table 50 (Formulation 18) and Table 51 (Formulation 12).

2) The contents of the human serum albumin multimer in the SN-38 formulations prepared by different methods were measured using SEC-HPLC. 5 l of the prepared samples were directly taken for detection, and chromatographic conditions were as shown in Table 43.

TABLE 51

Results of Stability Parameters of Formulation 18

| | Time point | | | |
|---|---|---|---|---|
| | Day 0 | 3 Months | 6 Months | |
| Item | 1 mg/ml | 1 mg/ml | 1 mg/ml | 0.83 mg/ml |
| pH | 6.6 | 6.8 | 6.7 | 6.6 |
| Moisture | 1.4% | 1.6% | 1.9% | |
| Osmotic pressure | 352 mOsmol/kg | 346 mOsmol/kg | 346 mOsmol/kg | 287 mOsmol/kg |
| Particle size and particle size distribution | 168 nm<br>d(0.9): 336 nm<br>d(0.5): 192 nm<br>d(0.1): 108 nm | 169 nm<br>d90: 338 nm<br>d50: 194 nm<br>d10: 111 nm | 172 nm<br>d90: 352 nm<br>d50: 197 nm<br>d10: 107 nm | 170 nm<br>d90: 332 nm<br>d50: 193 nm<br>d10: 110 nm |
| Human serum albumin multimer | 0.8% | 1.0% | 1.1% | |
| Content of cholesterol | 12.5 mg/vial | 12.6 mg/vial | 12.3 mg/vial | |
| Content of Span 20 | <1 mg/vial | <1 mg/vial | <1 mg/vial | |

TABLE 52

Results of Stability Parameters of Formulation 12

| | Time point | | | |
|---|---|---|---|---|
| | Day 0 | 3 Months | 6 Months | |
| Item | 1 mg/ml | 1 mg/ml | 1 mg/ml | 0.83 mg/ml |
| pH | 6.8 | 6.7 | 6.6 | 6.8 |
| Moisture | 2.5% | 2.7% | 2.0% | |
| Osmotic pressure | 312 mOsm/kg | 331 mOsm/kg | 322 mOsm/kg | 329 mOsm/kg |
| Particle size and particle size distribution | 195 nm<br>d90: 455 nm<br>d50: 254 nm<br>d10: 97.5 nm | 252 nm<br>d90: 758 nm<br>d50: 336 nm<br>d10: 90.3 nm | 181 nm<br>d90: 376 nm<br>d50: 227 nm<br>d10: 121 nm | 180 nm<br>d90: 400 nm<br>d50: 225 nm<br>d10: 116 nm |
| Human serum albumin multimer | 1.7% | 1.0% | 1.5% | |
| Content of Cholesterol | 15.0 mg/vial | 15.8 mg/vial | 15.8 mg/vial | |

The above results indicate that as time passed, the HSA-SN-38 formulation added with Span 20 has smaller particle size change and albumin multimer change, and was more stable.

Example 38: In Vivo Pharmacodynamic Study in SKOV-3 Human Ovarian Cancer Model 1. Experimental Objective: the antitumor activity and safety of Formulation 12 prepared in Example 31 and Formulation 18 prepared in Example 36 in a subcutaneous xenograft model of human ovarian cancer cell line SKOV-3 (ATCC HTB 77) in BALB/c nude mice were verified.

2. Experimental Method

SKOV-3 tumor masses were subcutaneously inoculated to 40 BALB/c nude mice. 18 tumor-bearing mice were selected on day 13 (D13) after the inoculation, and averagely divided into 3 groups, with 6 mice in each group. By tail intravenous injection, the mice were administered once a week, for a total of 4 weeks, and the specific dosage regimen was shown in Table 53. The therapeutic effect was evaluated based on relative tumor inhibition rate (TGI), and the safety was evaluated based on the body weight change and death of the animals.

TABLE 53

Antitumor Effects of Test Formulations in SKOV-3 Human Ovarian Cancer Model

| Control/Test Product | Number of Mice | Dose (mg/kg) | Dose Volume (μl/g) | Administration Route | Dosage Regimen |
|---|---|---|---|---|---|
| Blank | 6 | — | 10 | iv | QW × 4 |
| Formulation 12 | 6 | 30 | 10 | iv | QW × 4 |
| Formulation 18 | 6 | 30 | 10 | iv | QW × 4 |

Notes:
QW × 4 represents administration once a week, for a total of 4 weeks.

3. Statistical Analysis

The average values of the tumor of different groups were compared using one-way ANOVA in the experiment. Analysis of homogeneity of variance showed a significant difference in the F value, and multiple comparison was performed using Dunnet's T3 (heterogeneous variance) method after the ANOVA analysis. Analysis on all data was performed using SPSS 17.0. $p < 0.05$ was considered to indicate a significant difference.

Figure 28:
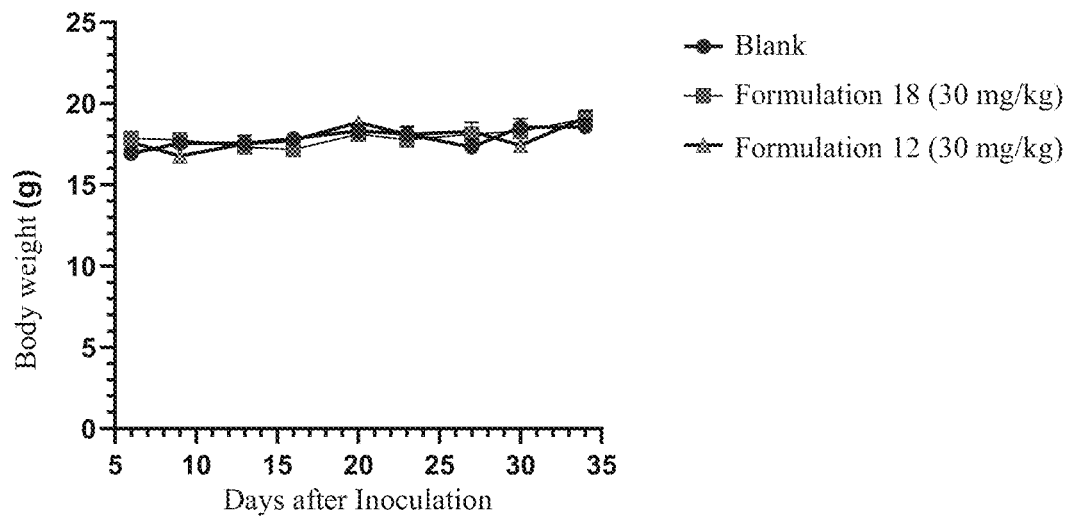
FIG. 28 shows body weight changes of test animals in Example 38.

4. Experimental Results 4.1 Body Weight Change: as shown in FIG. 28.

Figure 29:
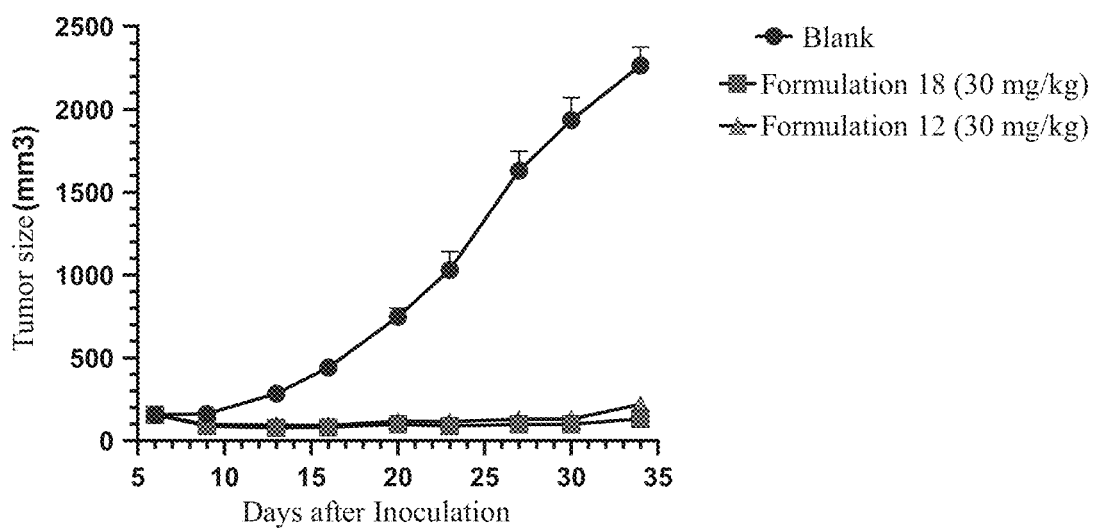
FIG. 29 and FIG. 30 show tumor volume changes of test animals in Example 38.
Figure 30:
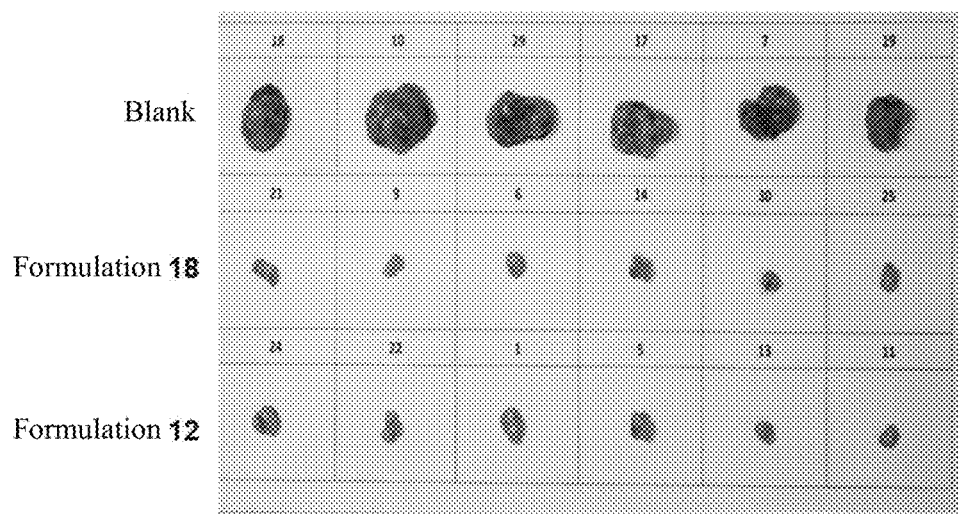

4.2 Tumor Volume Change: as shown in FIG. 29 and FIG. 30.

4.3 Table 54 shows the evaluation indicators for the antitumor efficacy of the HSA-SN-38 Formulation 12 and Formulation 18 in the SKOV-3 xenograft model.

TABLE 54

Efficacy of Test Formulations in SKOV-3 Human Ovarian Cancer Model

| Drug | n | Dose (mg/kg) | Body Weight (g, mean ± SEM) | | Change (%) | Tumor Volume (TV)/Weight (TW) (mean ± SEM) | | | T/C (%) | | p Value | |
|---|---|---|---|---|---|---|---|---|---|---|---|---|
| | | | Day 6 | Day 34 | | TV (mm³) Day 6 | TV (mm³) Day 34 | TW (mg) | TV | TW | TV | TW |
| Blank | 6 | — | 16.9 ± 0.2 | 18.6 ± 0.5 | +9.6 | 158 ± 11 | 2264 ± 112 | 1244 ± 200 | 100 | 100 | 1.000 | 1.000 |
| Formulation 18 | 6 | 30 | 17.9 ± 0.4 | 19.1 ± 0.4 | +6.9 | 157 ± 9 | 134 ± 6 | 65 ± 7 | 6 | 5 | .000 | .005 |
| Formulation 12 | 6 | 30 | 17.6 ± 0.4 | 19.1 ± 0.4 | +8.8 | 157 ± 8 | 221 ± 34 | 88 ± 16 | 10 | 7 | .000 | .006 |

Notes:
T/C (%) means a percentage of TV or TW of the treatment group (T) relative to the blank control group (C), and the smaller the value thereof, the better the tumor inhibition effect.

Conclusion:

Formulation 12 and Formulation 18 at a dose of 30 mg/kg had the effect of significantly inhibiting the tumor growth in the SKOV-3 human ovarian cancer model, and the tumor was substantially eliminated in the end. Moreover, during the experiment, no animal died and there was also no other toxic reaction observed. The results indicate that the formulation containing Span 20 (Formulation 18) and the formulation containing no Span 20 (Formulation 12) had equivalent antitumor activity.

Example 39: In Vivo Pharmacodynamic Study in HCT116 Human Colon Cancer Model

1. Experimental Objective: the antitumor activity and safety of Formulation 12 prepared in Example 31 and Formulation 18 prepared in Example 36 in the subcutaneous xenograft model of human colon cancer cell line HCT116 (ATCC CCL-247) in BALB/c nude mice were verified.

2. Experimental Method

The HCT116 tumor mass in a good state was cut into small tumor masses of 20-30 mm³ which were inoculated to the right scapulas of 40 mice. When the average tumor volume reached about 121 mm³ 15 days after the inoculation of the tumor masses, the mice with excessively small or large tumor volumes were screened out, and the remaining 18 mice were randomly grouped (3 groups, with 6 mice in each group) by tumor volume and administered with drugs (by tail intravenous injection) once a week, for a total of 4 weeks. The therapeutic effect was evaluated based on relative tumor inhibition rate (TGI), and the safety was evaluated based on the body weight change and death of the animals. One week after the last dose, tumors were taken from all the mice, weighed, and photographed.

TABLE 55

Antitumor Effects of Test Formulations in HCT116 Human Colon Cancer Model

| Control/Test Product | Number of Mice | Dose (mg/kg) | Does Volume (μl/g) | Administration Route | Dosage Regimen |
|---|---|---|---|---|---|
| Blank | 6 | — | 10 | iv | QW × 4 |
| Formulation 12 | 6 | 10 | 10 | iv | QW × 4 |
| Formulation 18 | 6 | 10 | 10 | iv | QW × 4 |

Notes:
QW × 4 represents administration once a week, for a total of 4 weeks.

3. Statistical Analysis

The average values of the tumor of different groups were compared using one-way ANOVA in the experiment. Analysis of homogeneity of variance showed a significant difference in the F value, and multiple comparison was performed using Dunnet's T3 (heterogeneous variance) method after the ANOVA analysis. Analysis on all data was performed using SPSS 17.0. $p<0.05$ was considered to indicate a significant difference.

Figure 31:
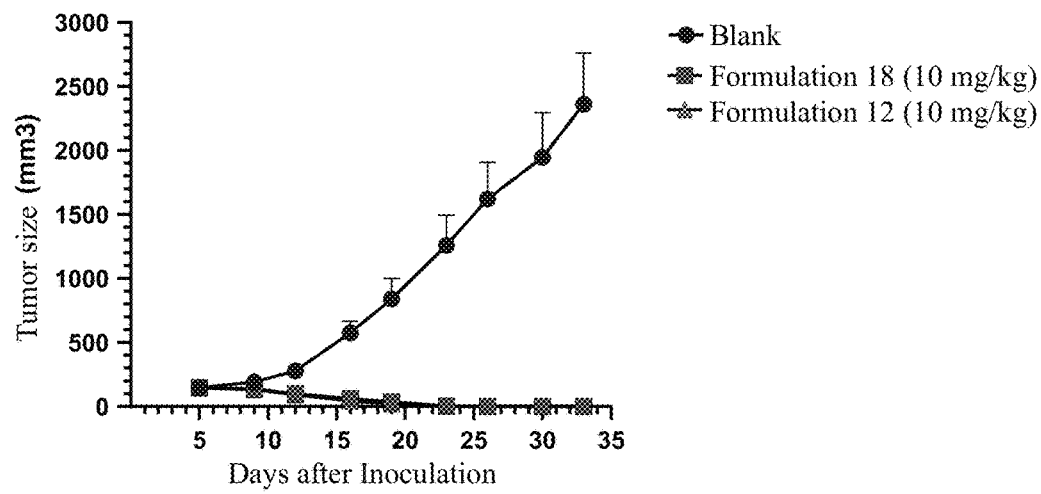
FIG. 31 shows body weight changes of test animals in Example 39.

4. Experimental Results 4.1 Body Weight Change: as shown in FIG. 31.

Figure 32:
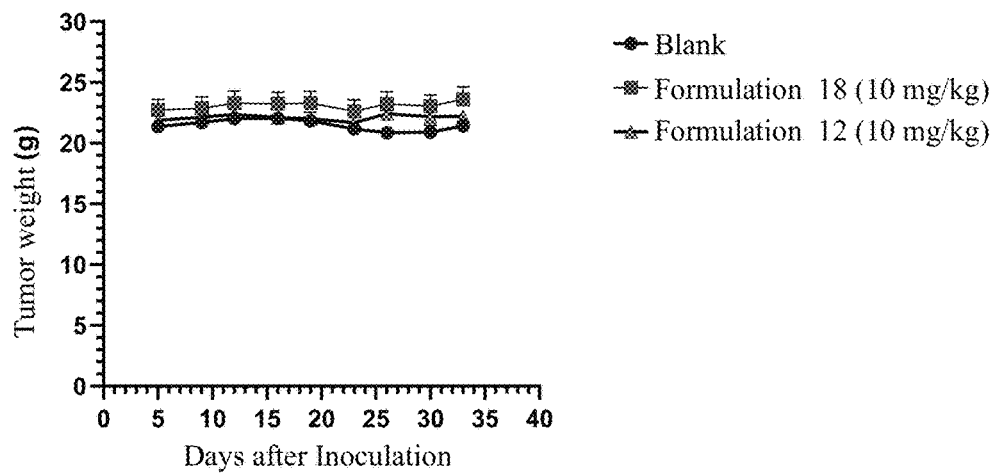
FIG. 32 and FIG. 33 show tumor volume changes of test animals in Example 39.
Figure 33:
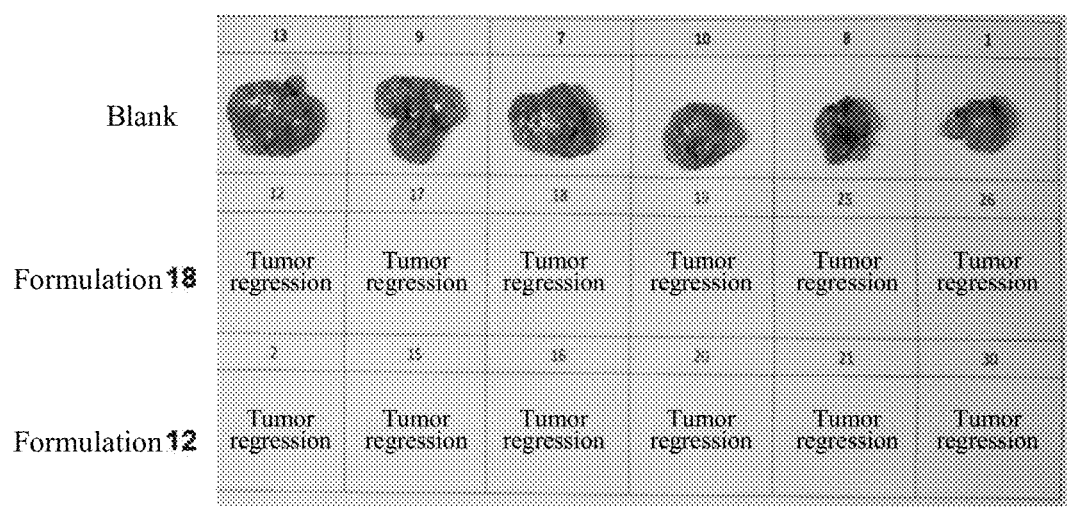

4.2 Tumor Volume Change: as shown in FIG. 32 and FIG. 33.

Conclusion:

Formulation 12 and Formulation 18 at a dose of 10 mg/kg had the effect of significantly inhibiting the tumor growth in the HCT116 human colon cancer model, and the tumor was substantially eliminated. Moreover, during the experiment, no animal died and there was also no other toxic reaction observed.

EQUIVALENTS AND INCORPORATION BY REFERENCE

The compositions, methods, and uses of the present application have been described herein with reference to some preferred embodiments. However, since particular variations are obvious to those skilled in the art based on the disclosure described herein, the present application should not be deemed to be limited thereto.

Unless otherwise defined, all technical and scientific terms used herein have the same meanings as commonly understood by those of ordinary skill in the art. In the specification and the claims, unless the context clearly indicates otherwise, the singular forms include the plural forms as well.

Moreover, to a certain extent, the methods of the present application are independent of particular orders of the steps described herein, and the particular order of the steps set forth in a claim should not be construed as a limitation to the claim.

All patent documents, patent applications, references, and publications cited herein are incorporated herein by reference in their entirety.

What is claimed is:

1. A pharmaceutical composition, comprising SN-38, a lipid, an albumin, sucrose, and sorbitan monolaurate,
   wherein the composition is in a solid form that can be reconstituted, and forms nanoparticles upon being reconstituted to form an aqueous composition, and wherein in the nanoparticles, the albumin encapsulates at least part of the SN-38 and optionally at least part of the lipid;
   wherein a ratio of lipid: SN-38 is about (0.5-8:1) (w:w);
   wherein a ratio of albumin: SN-38 is about (5-30): 1 (w:w);
   wherein a ratio of albumin: lipid is about (2-21): 1 (w:w); and
   wherein a ratio of sorbitan monolaurate: SN-38 is about (3-30): 100 (w:w); and
   wherein the lipid is selected from cholesterol and cholesteryl palmitate; and
   wherein the composition is optionally in the form of a solid powder, wherein the solid powder was optionally generated by lyophilization.

2. The pharmaceutical composition of claim 1, characterized in that a ratio of albumin: lipid is about (2-20): 1 (w:w), about (3-15): 1 (w:w), about (5-10): 1 (w:w), about 7:1 (w:w), or about 10:1 (w:w).

3. The pharmaceutical composition of claim 1, characterized in that, based on the total amount of the SN-38, the lipid, and the albumin in the composition,
the content of the SN-38 is about 3 w/w % to about 20 w/w %; and/or
based on the total amount of the SN-38, the lipid, and the albumin in the composition, the content of the lipid is about 3 w/w % to about 30 w/w %; and/or
based on the total amount of the SN-38, the lipid, and the albumin in the composition, the content of the albumin is about 60 w/w % to about 95 w/w %;
or,
based on the total amount of the SN-38, the lipid, and the albumin in the composition, the content of the SN-38 is about 3 w/w % to about 15 w/w %, about 4 w/w %, about 5 w/w %, about 6 w/w %, about 6.5 w/w %, about 7 w/w %, about 7.5 w/w %, about 8 w/w %, about 8.5 w/w %, about 9 w/w %, about 10 w/w %, about 11 w/w %, about 12 w/w %, about 13 w/w %, or about 14 w/w %; and/or
based on the total amount of the SN-38, the lipid, and the albumin in the composition, the content of the lipid is about 4 w/w % to about 30 w/w %, about 5 w/w %, about 6 w/w %, about 7 w/w %, about 8 w/w %, about 8.5 w/w %, about 9 w/w %, about 9.5 w/w %, about 10 w/w %, about 10.5 w/w %, about 11 w/w %, about 11.5 w/w %, about 12 w/w %, about 12.5 w/w %, about 13 w/w %, about 13.5 w/w %, about 14 w/w %, about 15 w/w %, about 16 w/w %, about 17 w/w %, about 18 w/w %, about 19 w/w %, about 20 w/w %, about 21 w/w %, about 24 w/w %, about 26 w/w %, or about 28 w/w %; and/or
based on the total amount of the SN-38, the lipid, and the albumin in the composition, the content of the albumin is about 60 w/w % to about 94 w/w %, about 64 w/w % to about 93 w/w %, about 66 w/w % to about 92 w/w %, about 68 w/w % to about 91 w/w %, about 70 w/w % to about 90 w/w %, about 75 w/w % to about 90 w/w %, about 76 w/w %, about 77 w/w %, about 78 w/w %, about 79 w/w %, about 80 w/w %, about 81 w/w %, about 82 w/w %, about 83 w/w %, about 84 w/w %, about 85 w/w %, about 86 w/w %, about 87 w/w %, about 88 w/w %, or about 89 w/w %; and/or
the sorbitan monolaurate has a content of about 0.1 w/w % to about 1.0 w/w %, about 0.2 w/w %, about 0.4 w/w %, about 0.6 w/w %, or about 0.8 w/w %, based on the total amount of the SN-38, the lipid, the albumin, and the sorbitan monolaurate in the composition.

4. The pharmaceutical composition of claim 1, characterized in that:
the ratio of lipid: SN-38 is about (0.5-6): 1 (w:w), about (0.5-5): 1 (w:w), about (0.5-3): 1 (w:w), about (1-8): 1 (w:w), about (1-6): 1 (w:w), about (1-5): 1 (w:w), about (1-4.5): 1 (w:w), about (1-4): 1 (w:w), about (1.2-4): 1 (w:w), about (1.2-3.8): 1 (w:w), about (1.4-3.6): 1 (w:w), about (1.4-2): 1 (w:w), about (1.5-2.5): 1 (w:w), about (1.6-3.4): 1 (w:w), about (1.8-3.2): 1 (w:w), about (2-3): 1 (w:w), about (2.2-2.8): 1 (w:w), about (2.4-2.6): 1 (w:w), about 1:1 (w:w), about 2.5:1 (w:w), about (0.8-1.8): 1 (w:w), about (0.9-1.7): 1 (w:w), about (1-1.4): 1; or about 1:1; and/or
the ratio of albumin: SN-38 is about (5-25): 1 (w:w), about (5-20): 1 (w:w), about (5-18): 1 (w:w), about (6-15): 1 (w:w), about (6-12): 1 (w:w), about (7-15): 1 (w:w), about (7-12): 1 (w:w), about (8-25): 1 (w:w), about (9-11): 1 (w:w), about (10-22.5): 1 (w:w), about (12.5-20): 1 (w:w), about (15-17.5): 1 (w:w), about (16-18): 1 (w:w), about 10:1 (w:w), about (9-21): 1 (w:w), about (9-20): 1 (w:w), about (11-18): 1 (w:w), about (11.1-17.3): 1 (w:w), or about 10:1 (w:w); and/or
the ratio of sorbitan monolaurate: SN-38 is about (4-30): 100 (w:w), about (5-30): 100 (w:w), about (6-30): 100 (w:w), about (7-30): 100 (w:w), about (8-30): 100 (w:w), about (10-30): 100 (w:w), about (12-30): 100 (w:w), about (14-30): 100 (w:w), about (15-30): 100 (w:w), about (16-25): 100 (w:w), about (18-20): 100 (w:w), about (5-10): 100 (w:w), about (5-9): 100 (w:w), about (6-8.6): 100 (w:w), about (6-8): 100 (w:w), or about (6.5-7): 100 (w:w); and/or
the ratio of albumin: lipid is about (3-15): 1 (w:w), about (5-10): 1 (w:w), about (6-8): 1 (w:w), about 7:1 (w:w), about (6-21): 1 (w:w), about (6.7-13): 1 (w:w), about (7-13): 1 (w:w), or about (11-12.7): 1 (w:w).

5. The pharmaceutical composition of claim 1, characterized in that, based on the total amount of the SN-38, the lipid, and the albumin in the composition,
the content of the SN-38 is about 3 w/w % to about 16 w/w %, about 3 w/w % to about 15 w/w %, about 4 w/w % to about 10 w/w %, about 4.5 w/w % to about 9.5 w/w %, about 5 w/w % to about 9 w/w %, or about 7.5 w/w % to about 8 w/w %; and/or
based on the total amount of the SN-38, the lipid, and the albumin in the composition, the content of the lipid in the composition is about 4 w/w % to about 12.5 w/w %, about 4.5 w/w % to about 12 w/w %, about 7 w/w % to about 10 w/w %, or about 7.5 w/w % to about 8 w/w %; and/or
based on the total amount of the SN-38, the lipid, and the albumin in the composition, the content of the albumin in the composition is about 75 w/w % to about 96 w/w %, about 76 w/w % to about 95 w/w %, about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %;
or,
based on the total amount of the SN-38, the lipid, and the albumin in the composition, the content of the SN-38 is about 3 w/w % to about 14 w/w %, about 3.5 w/w % to about 12 w/w %, about 4 w/w %, about 4.2 w/w %, about 4.5 w/w %, about 4.6 w/w %, about 4.8 w/w %, about 5 w/w %, about 5.5 w/w %, about 6 w/w %, about 6.5 w/w %, about 7 w/w %, about 7.5 w/w %, about 7.6 w/w %, about 7.8 w/w %, about 8 w/w %, about 8.5 w/w %, about 9 w/w %, about 9.2 w/w %, about 9.5 w/w %, about 9.6 w/w %, about 9.8 w/w %, about 10 w/w %, about 10.5 w/w %, about 11 w/w %, or about 11.5 w/w %; and/or
based on the total amount of the SN-38, the lipid, and the albumin in the composition, the content of the lipid is about 4 w/w % to about 25 w/w %, about 4.5 w/w % to about 20 w/w %, about 4.3 w/w %, about 4.5 w/w %, about 4.7 w/w %, about 5 w/w %, about 5.5 w/w %, about 6 w/w %, about 6.5 w/w %, about 6.7 w/w %, about 6.9 w/w %, about 7 w/w %, about 7.5 w/w %, about 7.6 w/w %, about 7.8 w/w %, about 8 w/w %, about 8.5 w/w %, about 9 w/w %, about 9.5 w/w %, about 10 w/w %, about 10.5 w/w %, about 11 w/w %, about 11.5 w/w %, about 12 w/w %, about 12.1 w/w %, about 12.3 w/w %, about 12.5 w/w %, about 13 w/w %, about 13.5 w/w %, about 14 w/w %, about 14.5 w/w %, about 15 w/w %, about 15.5 w/w %, about 16 w/w %, about 16.5 w/w %, about 17 w/w %, about 17.5 w/w %, about 18 w/w %, about 18.5 w/w %, about 19 w/w %, or about 19.5 w/w %; and/or based on the total amount of the SN-38, the lipid, and the albumin in the composition, the content of the albumin is about 78 w/w % to about 92 w/w %, about 79 w/w %, about 79.2 w/w %, about 79.4 w/w %, about 79.6 w/w %, about 79.8 w/w %, about 80 w/w %, about 81 w/w %, about 82 w/w %, about 83 w/w %, about 84 w/w %, about 84.3 w/w %, about 84.5 w/w %, about 84.7 w/w %, about 84.9 w/w %, about 85 w/w %, about 86 w/w %, about 87 w/w %, about 87.3 w/w %, about 87.5 w/w %, about 87.7 w/w %, about 87.9 w/w %, about 88 w/w %, about 89 w/w %, about 90 w/w %, about 91 w/w %, about 91.3 w/w %, or about 91.5 w/w %; and/or based on the total amount of the SN-38, the lipid, the albumin, and the sorbitan monolaurate in the composition, the content of the sorbitan monolaurate is about 0.14 w/w % to about 1.0 w/w %, about 0.2 w/w % to about 1.0 w/w %, about 0.22 w/w % to about 1.0 w/w %, about 0.24 w/w % to about 1.0 w/w %, about 0.26 w/w % to about 1.0 w/w %, about 0.28 w/w % to about 1.0 w/w %, about 0.3 w/w % to about 0.9 w/w %, about 0.32 w/w % to about 0.8 w/w %, about 0.34 w/w % to about 0.7 w/w %, about 0.36 w/w % to about 0.6 w/w %, about 0.38 w/w % to about 0.58 w/w %, about 0.4 w/w % to about 0.56 w/w %, about 0.42 w/w % to about 0.54 w/w %, about 0.44 w/w % to about 0.52 w/w %, about 0.46 w/w %, about 0.48 w/w %, about 0.5 w/w %, about 0.2 w/w % to about 0.8 w/w %, about 0.24 w/w % to about 0.7 w/w %, about 0.26 w/w % to about 0.7 w/w %, about 0.3 w/w % to about 0.65 w/w %, about 0.36 w/w % to about 0.6 w/w %, about 0.4 w/w % to about 0.58 w/w %, about 0.44 w/w % to about 0.56 w/w %, about 0.48 w/w % to about 0.54 w/w %, or about 0.5 w/w % to about 0.52 w/w %.

6. The pharmaceutical composition of claim 1, characterized in that the lipid is cholesteryl palmitate.

7. The pharmaceutical composition of claim 1, characterized in that the lipid is cholesterol.

8. The pharmaceutical composition of claim 7, characterized in that:

the ratio of cholesterol: SN-38 is about (1-6): 1 (w:w), about (1.2-5): 1 (w:w), about (1.4-4): 1 (w:w), about 3:1 (w:w), about 2:1 (w:w), about 1:1 (w:w), about (0.8-1.8): 1 (w:w), about (0.9-1.7): 1 (w:w), or about (1-1.4): 1; and/or the ratio of albumin: SN-38 is about (5-25): 1 (w:w), about (5-20): 1 (w:w), about (5-15): 1 (w:w), about (6-12): 1 (w:w), about (7-12): 1 (w:w), about (9-11): 1 (w:w), about 10:1 (w:w), about (9-21): 1 (w:w), about (9-20): 1 (w:w), about (11-18): 1 (w:w), or about (11.1-17.3): 1 (w:w); and/or the ratio of albumin: cholesterol is about (2-20): 1 (w:w), about (3-15): 1 (w:w), about (5-10): 1 (w:w), about 7:1 (w:w), about (6-21): 1 (w:w), about (6.7-13): 1 (w:w), about (7-13): 1 (w:w), or about (11-12.7): 1 (w:w); and/or based on the total amount of the SN-38, the cholesterol, and the albumin in the composition, the content of the SN-38 is about 3 w/w % to about 15 w/w %, about 4 w/w % to about 15 w/w %, about 6 w/w % to about 10 w/w %, about 8 w/w % to about 12 w/w %, about 4 w/w % to about 10 w/w %, about 4.5 w/w % to about 9.5 w/w %, about 5 w/w % to about 9 w/w %, or about 7.5 w/w % to about 8 w/w %; and/or based on the total amount of the SN-38, the cholesterol, and the albumin in the composition, the content of the cholesterol is about 5 w/w % to about 25 w/w %, about 6 w/w % to about 22 w/w %, about 15 w/w % to about 20 w/w %, about 4 w/w % to about 12.5 w/w %, about 4.5 w/w % to about 12 w/w %, about 7 w/w % to about 10 w/w %, or about 7.5 w/w % to about 8 w/w %; and/or based on the total amount of the SN-38, the cholesterol, and the albumin in the composition, the content of the albumin is about 64 w/w % to about 90 w/w %, about 70 w/w % to about 90 w/w %, about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %; and/or wherein, upon being reconstituted to form an aqueous composition comprising nanoparticles, the SN-38 existing in the nanoparticles accounts for at least about 3 w/w %, about 3 w/w % to about 13 w/w %, about 4 w/w % to about 12 w/w %, about 4 w/w %, about 5 w/w %, about 6 w/w %, about 7 w/w %, about 8 w/w %, about 9 w/w %, about 10 w/w %, or about 11 w/w %, of the total amount of the SN-38, the cholesterol, and the albumin in the composition.

9. The pharmaceutical composition of claim 7, wherein:

the ratio of cholesterol: SN-38 is about (1-3): 1 (w:w), about (1.2-2.5): 1 (w:w), about (1.4-2): 1 (w:w), about (1.5-2): 1 (w:w), about (1.3-1.8): 1 (w:w), about (1.4-1.6): 1 (w:w), about (1.5-1.7): 1 (w:w), about (1.2-1.5): 1 (w:w), about 1:1 (w:w), about (1.4-1.5): 1 (w:w), or about (0.8-1.8): 1 (w:w), about (0.9-1.7): 1 (w:w), or about (1-1.4): 1;

the ratio of albumin: SN-38 is about (5-15): 1 (w:w), about (5-12): 1 (w:w), about (6-12): 1 (w:w), about (7-12): 1 (w:w), about (9-11): 1 (w:w), about (10-12): 1 (w:w), about 11:1 (w:w), about (9-21): 1 (w:w), about (9-20): 1 (w:w), about (11-18): 1 (w:w), or about (11.1-17.3): 1 (w:w); and the ratio of albumin: cholesterol is about (3-10): 1 (w:w), about (4-8): 1 (w:w), about (5-7): 1 (w:w), about (6-21): 1 (w:w), about (6.7-13): 1 (w:w), about (7-13): 1 (w:w), or about (11-12.7): 1 (w:w).

10. The pharmaceutical composition of claim 7, characterized in that:

the ratio of cholesterol: SN-38 is about (1-5): 1 (w:w), about (1-4.5): 1 (w:w), about (1-4): 1 (w:w), about (1.2-3.8): 1 (w:w), about (1.4-3.6): 1 (w:w), about (1.6-3.4): 1 (w:w), about (1.8-3.2): 1 (w:w), about (2-3): 1 (w:w), about (2.2-2.8): 1 (w:w), about (2.4-2.6): 1 (w:w), about 2.5:1 (w:w), about 1:1 (w:w), about (0.8-1.8): 1 (w:w), about (0.9-1.7): 1 (w:w), or about (1-1.4): 1; and/or the ratio of albumin: SN-38 is about (5-25): 1 (w:w), about (5-20): 1 (w:w), about (6-19): 1 (w:w), about (7-18): 1 (w:w), about (8-16): 1 (w:w), about (9-14): 1 (w:w), about (10-12): 1 (w:w), about (9-21): 1 (w:w), about (9-20): 1 (w:w), about (11-18): 1 (w:w), or about (11.1-17.3): 1 (w:w); and/or the ratio of albumin: cholesterol is about (5-20): 1 (w:w), about (6-20): 1 (w:w), about (7-18): 1 (w:w), about (8-16): 1 (w:w), about (9-14): 1 (w:w), about (10-12): 1 (w:w), about (6-21): 1 (w:w), about (6.7-13): 1 (w:w), about (7-13): 1 (w:w), or about (11-12.7): 1 (w:w); and/or a ratio of sorbitan monolaurate: SN-38 is about (5-30): 100 (w:w), about (6-30): 100 (w:w), about (7-25): 100 (w:w), about (8-20): 100 (w:w), about (9-15): 100 (w:w), about (10-12): 100 (w:w), about (5-10): 100 (w:w), about (5-9): 100 (w:w), about (6-8.6): 100 (w:w), about (6-8): 100 (w:w), or about (6.5-7): 100 (w:w); and/or based on the total amount of the SN-38, the cholesterol, and the albumin in the composition, the content of the SN-38 is about 3 w/w % to about 10 w/w %, about 3.5 w/w % to about 9.5 w/w %, about 4 w/w %, about 4.5 w/w %, about 5 w/w %, about 5.5 w/w %, about 6 w/w %, about 6.5 w/w %, about 7 w/w %, about 7.5 w/w %, about 8 w/w %, about 8.5 w/w %, about 9 w/w %, about 4 w/w % to about 10 w/w %, about 4.5 w/w % to about 9.5 w/w %, about 5 w/w % to about 9 w/w %, or about 7.5 w/w % to about 8 w/w %; and/or based on the total amount of the SN-38, the cholesterol, and the albumin in the composition, the content of the cholesterol is about 4 w/w % to about 18 w/w %, about 4.5 w/w % to about 17.5 w/w %, about 5 w/w %, about 5.5 w/w %, about 6 w/w %, about 6.5 w/w %, about 7 w/w %, about 7.5 w/w %, about 8 w/w %, 8.5 w/w %, about 9 w/w %, about 9.5 w/w %, about 10 w/w %, about 10.5 w/w %, about 11 w/w %, about 11.5 w/w %, about 12 w/w %, about 12.5 w/w %, about 13 w/w %, about 13.5 w/w %, about 14 w/w %, about 14.5 w/w %, about 15 w/w %, about 15.5 w/w %, about 16 w/w %, about 16.5 w/w %, about 17 w/w %, about 4 w/w % to about 12.5 w/w %, about 4.5 w/w % to about 12 w/w %, about 7 w/w % to about 10 w/w %, or about 7.5 w/w % to about 8 w/w %; and/or based on the total amount of the SN-38, the cholesterol, and the albumin in the composition, the content of the albumin is about 78 w/w % to about 92 w/w %, about 79 w/w %, about 80 w/w %, about 81 w/w %, about 82 w/w %, about 83 w/w %, about 84 w/w %, about 85 w/w %, about 86 w/w %, about 87 w/w %, about 88 w/w %, about 89 w/w %, about 90 w/w %, about 91 w/w %, about 78 w/w % to about 93 w/w %, about 79 w/w % to about 91.5 w/w %, about 80 w/w % to about 90 w/w %, about 82 w/w % to about 89 w/w %, about 84 w/w % to about 88 w/w %, or about 84.5 w/w % to about 87.5 w/w %.

11. The pharmaceutical composition of claim 9, characterized in that:

upon being reconstituted to form an aqueous composition comprising nanoparticles, the SN-38 existing in the nanoparticles accounts for at least about 6 w/w % to about 12 w/w %, about 7 w/w % to about 11 w/w %, about 8 w/w % to about 10 w/w %, about 8.3%, or about 9 w/w %, of the total amount of the SN-38, the cholesterol, and the albumin in the composition; and/or upon being reconstituted to form an aqueous composition comprising nanoparticles, the SN-38 existing in the nanoparticles accounts for about 95 w/w % to about 99 w/w %, about 96 w/w % to about 99 w/w %, about 97 w/w % to about 99 w/w %, about 98 w/w % to about 99 w/w %, about 99 w/w % or higher, of the total amount of the SN-38 in the composition.

12. The pharmaceutical composition of claim 1, that the composition comprises no additional stabilizer; or wherein the sucrose has a content of at least about 2 w/v %, at least about 3 w/v %, at least about 5 w/v %, about 5 w/v % to about 30 w/v %, about 10 w/v % to about 25 w/v %, or about 15 w/v % to about 20 w/v %; and/or based on the total amount of the composition, the sucrose has a content of about 60 w/w % to about 98 w/w %, about 65 w/w % to about 97 w/w %, about 68 w/w % to about 96 w/w %, about 69 w/w % to about 95 w/w %, about 70 w/w % to about 94 w/w %, about 71 w/w % to about 93 w/w %, about 72 w/w % to about 92 w/w %, about 73 w/w %, about 74 w/w %, about 75 w/w %, about 76 w/w %, about 77 w/w %, about 78 w/w %, about 79 w/w %, about 80 w/w %, about 81 w/w %, about 82 w/w %, about 83 w/w %, about 84 w/w %, about 85 w/w %, about 86 w/w %, about 87 w/w %, about 88 w/w %, about 89 w/w %, about 90 w/w %, about 91 w/w %, about 70 w/w % to about 96 w/w %, about 70 w/w % to about 90 w/w %, about 72 w/w % to about 89 w/w %, about 74 w/w % to about 88 w/w %, about 76 w/w % to about 87 w/w %, about 80 w/w % to about 96 w/w %, about 80 w/w % to about 86 w/w %, about 81 w/w % to about 86 w/w %, about 82 w/w % to about 85 w/w %, about 83 w/w % to about 84 w/w %, or about 84 w/w % to about 95 w/w %.

13. The pharmaceutical composition of claim 1, characterized in that the open-ring SN-38 in the composition accounts for about 2 w/w % or lower, or about 1.8 w/w % or lower, of the total amount of the SN-38; and/or an albumin multimer does not exist or substantially does not exist in the composition; or, the albumin in a monomer form in the composition accounts for at least about 95 w/w, at least about 96%, at least about 98%, at least about 99%, at least about 99.2%, at least about 99.4%, or at least about 99.5%, of the total amount of the albumin.

14. The pharmaceutical composition of claim 1, characterized in that the albumin is selected from human serum albumin (HSA), recombinant human albumin (rHA), bovine serum albumin, and porcine serum albumin.

15. The pharmaceutical composition of claim 14, characterized in that the albumin comprises an amino acid sequence shown in SEQ ID NO:1.

16. The pharmaceutical composition of claim 14, characterized in that the albumin is selected from human serum albumin (HSA), and recombinant human albumin (rHA).

17. An aqueous pharmaceutical composition formed by reconstituting the composition of claim 1, wherein the composition comprises nanoparticles and wherein in the nanoparticles, the albumin encapsulates at least part of the SN-38 and optionally at least part of the lipid.

18. The aqueous pharmaceutical composition of claim 17, wherein, the SN-38 existing in the nanoparticles accounts for at least about 3 w/w %, about 3 w/w % to about 13 w/w %, about 4 w/w % to about 12 w/w %, about 4 w/w %, about 5 w/w %, about 6 w/w %, about 7 w/w %, about 8 w/w %, about 9 w/w %, about 10 w/w %, or about 11 w/w %, of the total amount of the SN-38, the cholesterol, and the albumin in the composition; and/or the SN-38 existing in the nanoparticles accounts for about 95 w/w % to about 99 w/w %, about 96 w/w % to about 99 w/w %, about 97 w/w % to about 99 w/w %, about 98 w/w % to about 99 w/w %, about 99 w/w % or higher, of the total amount of the SN-38 in the composition.

19. A method for treating a subject having an SN-38 sensitive tumor, comprising administering a therapeutically effective amount of the composition of claim 17 to the subject.

20. The method of claim 19, wherein the tumor is selected from SN-38 sensitive colorectal cancer, SN-38 sensitive small cell lung cancer, SN-38 sensitive lymph cancer, SN-38 sensitive breast cancer, SN-38 sensitive triple-negative breast cancer, SN-38 sensitive esophageal cancer, SN-38 sensitive gastric cancer, SN-38 sensitive liver cancer, SN-38 sensitive renal cancer, SN-38 sensitive pancreatic cancer, SN-38 sensitive uterine cancer, and SN-38 sensitive ovarian cancer.

21. A method for preparing the pharmaceutical composition of claim 1, characterized in that the method includes the following steps:
  (1) dissolving the SN-38, the lipid, and the Span 20 using a mixed organic solvent comprising a first organic solvent selected from DMSO and ethanol and a second organic solvent selected from $CHCl_3$ and a mixture of $CH_2Cl_2$ and $CHCl_3$ to form an organic phase, wherein in the mixed organic solvent, a volume ratio of the second organic solvent to the DMSO or alcohol ethanol is about 1:1 (v/v) to about 20:1 (v/v), about 1:1 to about 5:1 (v/v), about 1:1 to about 4:1 (v/v), about 1:1 to about 4:1 (v/v), about 1.5:1 (v/v) to about 3:1 (v/v), or about 2:1 (v/v) to 7:3 (v/v); and preparing an aqueous solution of the albumin as an aqueous phase;
  (2) mixing the organic phase and the aqueous phase at a ratio of the organic phase: the aqueous phase of about 1:5 (v/v) to about 1:20 (v/v) to prepare an emulsion, wherein the emulsion comprises the nanoparticles, wherein in the nanoparticles, the albumin encapsulates at least part of the SN-38 and optionally at least part of the lipid;
  (3) removing the organic solvent; and
  (4) sterilizing the product obtained in step (3), optionally by filtering through a filter membrane of about 0.2 um; and
  (5) drying the product obtained in step (4), optionally by spray drying or lyophilizing, to provide the pharmaceutical composition of claim 1;
  wherein sucrose is added in step (2), and/or step (5) includes adding sucrose to the product obtained in step (4) before said drying; and
  wherein optionally, the second organic solvent is $CHCl_3$, or a mixture of $CH_2Cl_2$ and $CHCl_3$, wherein optionally, a volume ratio of $CH_2Cl_2$ to $CHCl_3$ in the mixture is about 2:5-1:1, preferably about 2:5.

22. The method of claim 21, characterized in that in step (2), the ratio of the organic phase: the aqueous phase is about 1:7 (v/v) to about 1:15 (v/v), about 1:10 (v/v) to about 1:12 (v/v), e.g., about 1:5 (v/v) to about 1:12 (v/v), about 1:5 (v/v) to about 1:12 (v/v), about 1:6 (v/v), about 1:7 (v/v), or about 1:10 (v/v).

* * * * *